(12) United States Patent
Sum et al.

(10) Patent No.: US 7,799,915 B2
(45) Date of Patent: Sep. 21, 2010

(54) ANILINO-PYRIMIDINE ANALOGS

(75) Inventors: Fuk-Wah Sum, Pomona, NY (US); Dennis William Powell, Cortlandt Manor, NY (US); Yixian Zhang, Pearl River, NY (US); Lijing Chen, Cupertino, CA (US); Scott Lee Kincaid, Middletown, NY (US); Lee Dalton Jennings, Chestnut Ridge, NY (US); Yongbo Hu, River Edge, NJ (US); Adam Matthew Gilbert, Congers, NY (US); Matthew Gregory Bursavich, Tuckahoe, NY (US)

(73) Assignee: Wyeth LLC, Madison, NJ (US)

( * ) Notice: Subject to any disclaimer, the term of this patent is extended or adjusted under 35 U.S.C. 154(b) by 925 days.

(21) Appl. No.: 11/248,495

(22) Filed: Oct. 13, 2005

(65) Prior Publication Data
US 2006/0079543 A1    Apr. 13, 2006

Related U.S. Application Data

(60) Provisional application No. 60/617,668, filed on Oct. 13, 2004.

(51) Int. Cl.
*C07D 239/02* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. ..................... 544/330; 544/331
(58) Field of Classification Search .................. None
See application file for complete search history.

(56) References Cited

U.S. PATENT DOCUMENTS

| | | | |
|---|---|---|---|
| 3,775,168 A | 11/1973 | Roth | |
| 4,788,195 A * | 11/1988 | Torley et al. | 514/252.18 |
| 4,876,252 A | 10/1989 | Torley et al. | |
| 5,786,354 A | 7/1998 | Warrellow et al. | |
| 5,849,770 A | 12/1998 | Head et al. | |
| 6,337,335 B1 | 1/2002 | Hutchings et al. | |
| 6,342,503 B1 | 1/2002 | Aldrich et al. | |
| 6,552,029 B1 | 4/2003 | Davis et al. | |
| 6,579,983 B1 | 6/2003 | Batchelor et al. | |
| 6,600,037 B1 | 7/2003 | Davis et al. | |
| 6,670,348 B1 | 12/2003 | Rosen et al. | |
| 6,693,108 B2 | 2/2004 | Green et al. | |
| 6,703,414 B2 | 3/2004 | Powis et al. | |
| 2002/0132823 A1* | 9/2002 | Han et al. | 514/275 |

FOREIGN PATENT DOCUMENTS

| | | |
|---|---|---|
| CH | 210 790 | 7/1940 |
| CH | 210 790 A | 7/1940 |
| FR | 829 926 | 7/1938 |
| FR | 829 926 A | 7/1938 |
| GB | 2 302 021 A | 8/1997 |
| WO | WO 01/12621 | 2/2001 |
| WO | WO 01/12621 A | 2/2001 |
| WO | WO 01/14375 | 3/2001 |
| WO | WO 01/14375 A | 3/2001 |
| WO | WO/0129009 | 4/2001 |
| WO | WO 01/64654 | 9/2001 |
| WO | WO 01/64654 A | 9/2001 |
| WO | WO 02/20512 | 3/2002 |
| WO | WO/0220512 | 3/2002 |
| WO | WO/0246171 | 6/2002 |
| WO | WO 02/066481 | 8/2002 |
| WO | WO 02/066481 A | 8/2002 |
| WO | WO02/079197 | * 10/2002 |
| WO | WO 02/083668 | 10/2002 |
| WO | WO 02/083668 A | 10/2002 |
| WO | WO 02/092573 | 11/2002 |
| WO | WO 02/092573 A | 11/2002 |
| WO | WO 02/096905 | 12/2002 |
| WO | WO 02/096905 A | 12/2002 |
| WO | WO02096888 | * 12/2002 |
| WO | WO 03/074515 | 9/2003 |
| WO | WO 03/074515 A | 9/2003 |
| WO | WO 03/076434 | 9/2003 |
| WO | WO 03/076434 A | 9/2003 |
| WO | WO 2004/024093 | 3/2004 |
| WO | WO 2004/043467 | 5/2004 |
| WO | WO 2004/043467 A | 5/2004 |

(Continued)

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray
(74) *Attorney, Agent, or Firm*—David Rubin; Jeffrey H. Tidwell

(57) ABSTRACT

The present invention relates to compounds of formula I:

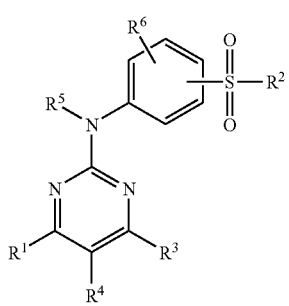

wherein $R^1$, $R^2$, $R^3$, $R^4$, $R^5$, and $R^6$ are defined herein.

59 Claims, 15 Drawing Sheets

FOREIGN PATENT DOCUMENTS

| | | |
|---|---|---|
| WO | WO 2004/043953 | 5/2004 |
| WO | WO 2004/043953 A | 5/2004 |

OTHER PUBLICATIONS

Vippagunta et. al. Advanced Drug Delivery Reviews 48 (2001) 3-26.*

Borisy, et. al., Proceedings of the National Academy of Sciences of the United States of America, 100(13) 7977-7982.*

Anderson, M. et al. "Imidazo[1,2a]pyridines: A potent and selective class of cyclin-dependent kinase inhibitors identified through structure-based hybridisation", Bioorganic & Medicinal Chemistry Letters, vol. 13, No. 18, Sep. 15, 2003, pp. 3021-3026.

Cross, P. et al., "Cerebrovasodilatation through selective inhibition of the enzyme carbonic anhydrase. 1. Substittued benzenedisulfonamides", Journal Med. Chem., vol. 21, No. 9, Sep. 1, 1978, pp. 845-849.

Anderson, Malcom et al., "Imidazo[1, 2a]pyridines: A potent and selective class of cyclin-dependent kinase inhibitors identified through structure-based hybridisation" Bioorganic & Medicinal Chemistry Letters, vol. 13, No. 18, pp. 3021-3026, Sep. 15, 2003.

Cross, Peter et al., "Cerebrovasodilatation through selective inhibition of the enzyme carbonic anhydrase. 1. Substituted benzenedisulfonamides" J. Med. Chem. vol. 21, No. 9, pp. 845-850, Sep. 1, 1978.

International Search Report from PCT/US05/36674.

Ihle, N.T., et al., "Molecular pharmacology and antitumor activity of PX-866, a novel inhibitor or phosphoinositide-3-kinase signaling" (1996) Mol. Cancer Therapeutics, vol. 3, No. 7,pp. 763-772 (2004).

Ihle, N.T., et al., "The phosphatidylinositol-3-kinase inhibitor PS-866 over comes resistance to the epidermal growth factor receptor inhibitor gefitinib in A-549 human non-small cell lung cancer xenografts" Mol. Cancer Therapeutics, vol. 4, No. 9, pp. 1349-1357, (2005).

Pasut, G., et al., "Protein, peptide andnon-peptide drug PEGylation for therapeutic application," Expert Opinion, vol. 14, No. 6, pp. 859-894 (2004).

von Walter Haefliger, et al., "Einiunrung der Corticoid-Seitenkette bei Wortmannin," Helvetica Chimica Acta, vol. 58, No. 6. pp. 1629-1633, (1975).

Wipf, P., et al., "Synthesis and biological evaluation of synthetic viridins derived from C(20) -heteroalkylation of the steroidal PI-3-kinase inhibitor," Org. Biomol. Chem., vol. 2, pp. 1911-1920, (2004).

* cited by examiner

Scheme 1: The Guanidine and Enaminone Reaction

Preparation of the Enaminone G-1:

Preparation of the Guanidine Derivative G-2:

Preparation of the Guanidine Derivative G-2:

ANILINO-PYRIMIDINE ANALOGS

This application claims the benefit of U.S. Provisional Patent Application Ser. No. 60/617,668 filed Oct. 13, 2004, which is herein incorporated by reference.

FIELD OF THE INVENTION

The present invention relates to anilino-pyrimidine analogs that are useful for inhibiting kinase activity.

BACKGROUND OF THE INVENTION

Nuclear factor-κB (NF-κB) is a transcriptional factor that regulates the expression of important genes related to cell survival. Activation of NF-κB is central to inflammatory response because it regulates the expression of pro-inflammatory cytokines such as tumor necrosis factor-α (TNF-α). TNF-α not only induces inflammation, but also acts as a survival factor for many cancers and can stimulate the production of angiogenic factors. TNF-α has been found in ovarian, breast, prostate, bladder, and colorectal cancer as well as in lymphomas and leukemias. The role of NF-κB in cancer has been further illuminated by research showing that NF-κB promotes tumorigenesis by suppressing apoptosis and stimulating cell proliferation. Haefner, B. (2002) "NF-κB: arresting a major culprit in cancer," *Drug Discovery Today*, 7, 653-663. Because of the role of NF-κB in tumorigenesis and inflammation, NF-κB inhibitors may prove useful as anticancer and anti-inflammation therapeutic agents.

The primary form of NF-κB is retained in the cytoplasm of resting cells by IκB, an inhibitor of NF-κB. NF-κB is activated by stimulation of a cellular kinase complex known as IκB kinase ("IKK") complex, comprising subunits IKKα, β, and γ. Upon stimulation by, for example, a toxin, a cytokine (such as TNF-α), or ionizing radiation, IKK phosphorylates IκB and triggers ubiquitination-dependent degradation through the proteasome pathway. With IκB destroyed, NF-κB is free to enter the nucleus and activate transcription. Hu, M. (2004) "IκB Kinase Promotes Tumorigenesis through Inhibition of Forkhead FOXO3a," *Cell*, 117, 225-237. Haefner, B. (2002) "NF-κB: arresting a major culprit in cancer," *Drug Discovery Today*, 7, 653-663.

Aberrant expression of IKK has been correlated with activation of NF-κB and, in turn, tumorigenesis and cell proliferation. High IKK levels may also promote tumorigenesis by negatively regulating other transcription factors, such as FOXO factors. Hu, M. (2004) "IκB Kinase Promotes Tumorigenesis through Inhibition of Forkhead FOXO3a," *Cell*, 117, 225-237. Thus, inhibiting IKK may inhibit cell proliferation and tumorigenesis. Other anilino-pyrimidine derivatives have been shown to inhibit inappropriately high kinase activity. See, e.g., U.S. Pat. No. 6,048,866. However, there remains a need for agents that selectively inhibit kinase activity, including IKK. The present invention fulfills this need.

SUMMARY OF THE INVENTION

In one embodiment, the present invention provides a compound of formula I:

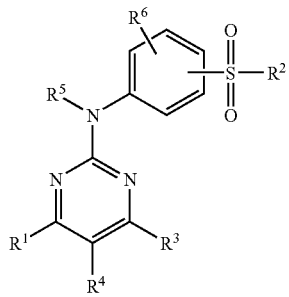

wherein:

$R^1$ is hydrogen;

$R^2$ is selected from the group consisting of $NR^7R^8$, guanidinyl, ureido, optionally substituted imidazolyl, optionally substituted alkyl, optionally substituted alkenyl, optionally substituted alkynyl, hydroxy, and alkoxy;

$R^3$ is selected from the group consisting of hydrogen; optionally substituted phenyl; an optionally substituted 5 or 6 membered heteroaryl ring with 1 to 4 heteroatoms, provided that the heteroaryl ring is not pyridine, furan, isoxazole, pyrazole, triazole, imidazole, or thiazole; a benzene ring fused to a 4 to 8 membered ring containing 0 to 4 heteroatoms, interrupted by 0 to 2 of the groups C=O, SO, or $SO_2$, and optionally substituted; an optionally substituted monocyclic or polycyclic ring containing 0 to 4 heteroatoms; optionally substituted alkenyl; optionally substituted alkynyl; —$NR^7R^8$; —$COOR^9$; —$CONR^7R^8$; and —$SO_2R^{10}$;

$R^4$ is hydrogen;

$R^5$ is selected from the group consisting of hydrogen, methyl, alkyl, alkylcarbonyl, alkoxycarbonyl, alkylsulfonyl, hydroxymethyl, and alkylaminomethyl;

$R^6$ is selected from the group consisting of hydrogen; halogen; optionally substituted phenyl; an optionally substituted 5 or 6 membered heteroaryl ring with 1 to 4 heteroatoms; a benzene ring fused to a 4 to 8 membered ring containing 0 to 4 heteroatoms, interrupted by 0 to 2 of the groups C=O, SO, or $SO_2$, and optionally substituted; an optionally substituted monocyclic or polycyclic ring containing 0 to 4 heteroatoms; —$NR^7R^8$; —$COOR^9$; —$CONR^7R^8$; —$SO_2R^{10}$; optionally substituted alkyl; optionally substituted alkenyl; optionally substituted alkynyl; hydroxy; alkoxy; $OR^7$; and $SR^7$;

$R^7$ and $R^8$ are independently selected from the group consisting of hydrogen; optionally substituted alkyl; optionally substituted alkenyl; optionally substituted alkynyl; optionally substituted aryl; optionally substituted heteroaryl; hydroxy; alkoxy; alkylamino; arylamino; heteroarylamino; —$NCOR^9$; —$COR^9$; —$CONR^7R^8$; $SO_2R^{10}$; optionally substituted 3 to 10 membered cyclic amines containing 0 to 3 heteroatoms;

optionally, $R^7$ and $R^8$ together form an optionally substituted 3 to 12 membered monocyclic or bicyclic ring containing 0 to 4 heteroatoms;

$R^9$ is selected from the group consisting of hydrogen, methyl, trifluoromethyl, optionally substituted alkyl, optionally substituted aryl, and optionally substituted heteroaryl;

$R^{10}$ is selected from the group consisting of methyl, trifluoromethyl, optionally substituted alkyl, optionally substituted aryl, optionally substituted heteroaryl, and $NR^7R^8$;

and the salts, solvates, and hydrates thereof.

In another embodiment, the present invention provides preferred substituents and specific compounds of formula I.

In another embodiment, the present invention also provides pharmaceutical compositions comprising a compound of the present invention and a pharmaceutically acceptable carrier. In another embodiment, the present invention provides a method of inhibiting kinase action, especially IKK, in a cell by providing a compound of the present invention. The present invention also provides a method of inhibiting kinase activity, especially IKK, in a mammal, especially a human, by administering a compound or pharmaceutical composition of the present invention. The present invention also provides a method of treating a kinase-dependent condition, especially inflammation or cancer, by administering a compound of the present invention.

In yet another embodiment, the present invention provides methods of treating diseases associated with NF-κB activation by administering a compound of the present invention.

In other embodiments, the present invention provides methods of treating cancer; inflammatory or autoimmune conditions; cardiovascular, metabolic, or ischemic conditions; infectious diseases, particularly viral infections; as well as pre- or post-menopausal conditions, particularly osteoporosis, by administering a compound of the present invention.

The present invention also provides methods further comprising administering an additional inhibitor of a protein kinase of the NF-κB pathway.

In another embodiment, the present invention provides processes for making a compound of formula I as defined above. The present invention also encompasses intermediates of these processes.

DETAILED DESCRIPTION

Figure 1:
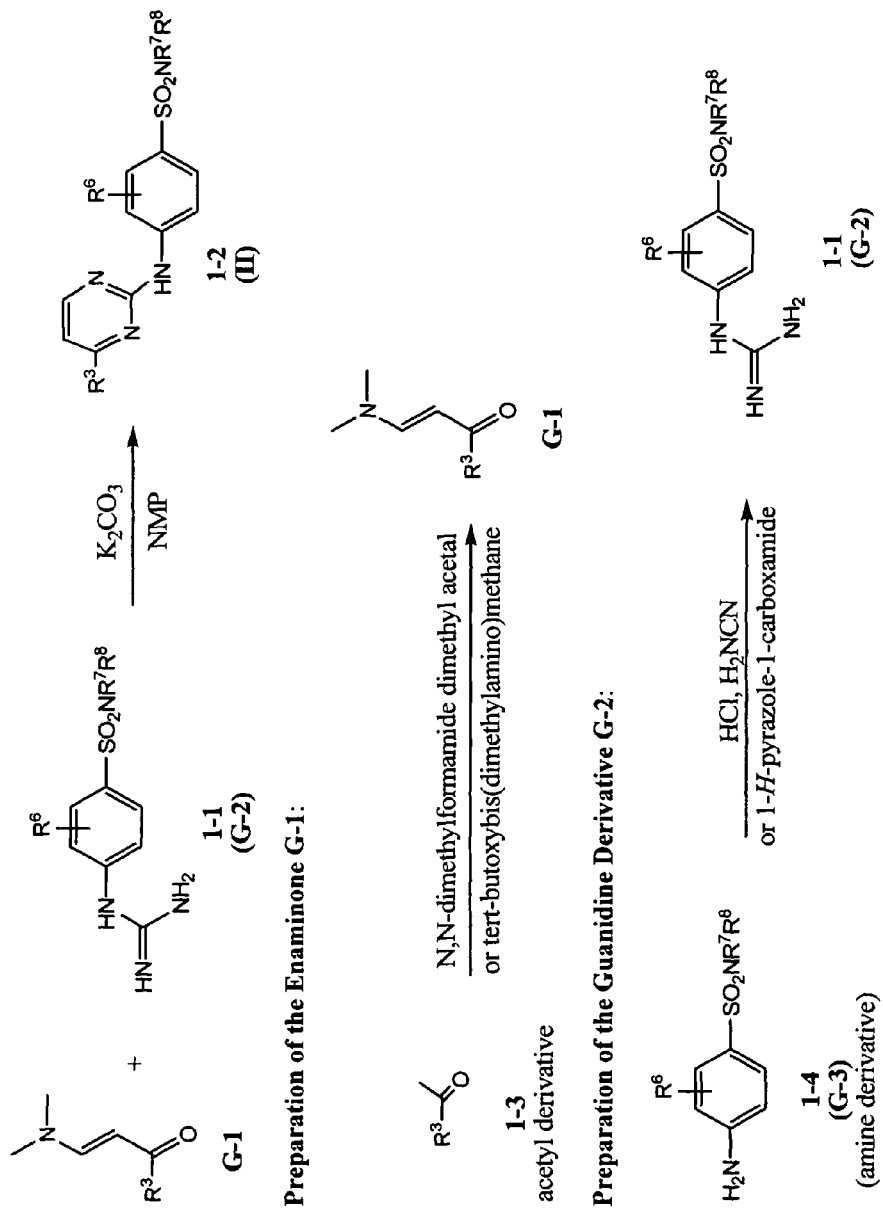
FIGS. 1-8 depict exemplary guanidine and enaminone reactions.

The present invention relates to anilino-pyrimidine analogs, pharmaceutical compositions, and methods using the same. In one embodiment, the present invention provides a compound of formula I:

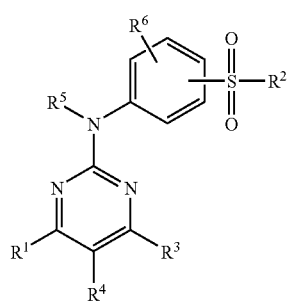

wherein:

$R^1$ is hydrogen;

$R^2$ is selected from the group consisting of $NR^7R^8$, guanidinyl, ureido, optionally substituted imidazolyl, optionally substituted alkyl, optionally substituted alkenyl, optionally substituted alkynyl, hydroxy, and alkoxy;

$R^3$ is selected from the group consisting of hydrogen; optionally substituted phenyl; an optionally substituted 5 or 6 membered heteroaryl ring with 1 to 4 heteroatoms, provided that the heteroaryl ring is not pyridine, furan, isoxazole, pyrazole, triazole, imidazole, or thiazole; a benzene ring fused to a 4 to 8 membered ring containing 0 to 4 heteroatoms, interrupted by 0 to 2 of the groups C=O, SO, or $SO_2$, and optionally substituted; an optionally substituted monocyclic or polycyclic ring containing 0 to 4 heteroatoms; optionally substituted alkenyl; optionally substituted alkynyl; $-NR^7R^8$; $-COOR^9$; $-CONR^7R^8$; and $-SO_2R^{10}$;

$R^4$ is hydrogen;

$R^5$ is selected from the group consisting of hydrogen, methyl, alkyl, alkylcarbonyl, alkoxycarbonyl, alkylsulfonyl, hydroxymethyl, and alkylaminomethyl;

$R^6$ is selected from the group consisting of hydrogen; halogen; optionally substituted phenyl; an optionally substituted 5 or 6 membered heteroaryl ring with 1 to 4 heteroatoms; a benzene ring fused to a 4 to 8 membered ring containing 0 to 4 heteroatoms, interrupted by 0 to 2 of the groups C=O, SO, or $SO_2$, and optionally substituted; an optionally substituted monocyclic or polycyclic ring containing 0 to 4 heteroatoms; $-NR^7R^8$; $-COOR^9$; $-CONR^7R^8$; $-SO_2R^{10}$; optionally substituted alkyl; optionally substituted alkenyl; optionally substituted alkynyl; hydroxy; alkoxy; $OR^7$; and $SR^7$;

$R^7$ and $R^8$ are independently selected from the group consisting of hydrogen; optionally substituted alkyl; optionally substituted alkenyl; optionally substituted alkynyl; optionally substituted aryl; optionally substituted heteroaryl; hydroxy; alkoxy; alkylamino; arylamino; heteroarylamino; $-NCOR^9$; $-COR^9$; $-CONR^7R^8$; $SO_2R^{10}$; optionally substituted 3 to 10 membered cyclic amines containing 0 to 3 heteroatoms;

optionally, $R^7$ and $R^8$ together form an optionally substituted 3 to 12 membered monocyclic or bicyclic ring containing 0 to 4 heteroatoms;

$R^9$ is selected from the group consisting of hydrogen, methyl, trifluoromethyl, optionally substituted alkyl, optionally substituted aryl, and optionally substituted heteroaryl;

$R^{10}$ is selected from the group consisting of methyl, trifluoromethyl, optionally substituted alkyl, optionally substituted aryl, optionally substituted heteroaryl, and $NR^7R^8$;

and the salts, solvates, and hydrates thereof.

In some embodiments, the R groups of the present invention are optionally substituted. Unless otherwise specified, optionally substituted means having zero, one, or more than one substituents. Unless otherwise specified, substituted means having one or more substituents. Substituents include hydrogen, halogen, cyano, nitro, alkylamino, hydroxy, alkoxy, alkanoyl, carbonyl, carbamoyl, trifluoromethyl, trifluoromethoxy, aryl, heteroaryl, aralkyl, aryloxy, alkylthio, arylthio, thioyl, $-COOR^9$, $-CONR^7R^8$, $NR^7R^8$ (including cyclic amines as described below), $SR^7$, and $-SO_2R^{10}$. When the substituted group is aryl or heteroaryl, the substituents further include methyl groups and optionally substituted $C_{2-10}$ straight, branched, or cyclic alkyl, alkenyl, or alkynyl groups. The substituents on the R groups can also be optionally substituted.

Exemplary halogens include, but are not limited to, fluorine, chlorine, bromine, and iodine.

Unless otherwise specified, alkyl, alkenyl, and alkynyl groups have 1 to 10 carbon atoms and may be straight, branched, or cyclic.

Alkyl means a straight chain or branched, cyclic or non-cyclic hydrocarbon.

Alkenyl means a straight chain or branched, cyclic or non-cyclic hydrocarbon having at least 2 carbon atoms and including at least one carbon-carbon double bond.

Alkynyl means a straight chain or branched hydrocarbon having at least 2 carbon atoms and including at least one carbon-carbon triple bond.

Heteroatom means an atom selected from nitrogen, which can be quaternized; oxygen; and sulfur, including sulfoxide and sulfone.

Alkoxy means a group —OR, wherein R is an alkyl, alkenyl, or alkynyl group which can optionally be substituted with one or more functional groups.

Hydroxy means —OH.

Carbonyl means carbon bonded to oxygen with a double bond, i.e., C=O.

Amino means the —NH$_2$ group.

Hydrates are solid compounds containing water molecules combined in a definite ratio as an integral part of the crystal.

Solvates are solid compounds containing solvent molecules combined in a definite ratio as an integral part of the crystal. Examples of aryl groups include, but are not limited to phenyl and naphthyl groups.

Heteroaryl means an aromatic heterocycle ring, including both mono- bi- and tricyclic ring systems, wherein at least one carbon atom of ring system is replaced with a heteroatom independently selected from nitrogen, oxygen and sulfur. Examples of heteroaryl groups include, but are not limited to pyridyl, pyrimidyl, thienyl, furanyl, imidazolyl, triazinyl, oxazolyl, isoxazolyl, pyrazolyl, triazolyl, tetrazolyl, pyrrole, pyrazinyl, and thiazolyl groups. Examples of heterocyclic groups include, but are not limited to saturated or partially saturated heteroaryls, including but not limited to pyrazoline, oxazolone, thiazolone, thiadiazolone, piperazine, pyrrolidine, piperidine, morpholine, benzoimidazolone, benzoxazolone, benzodioxazol, benzodioxazolone, benzo[1,4]oxazin-3-one, 3,4-dihydroquinoxaline-2-one, benzo[1,4]dioxene-2-one, and 1,2,3,4-tetrahydroquinoxaline. Examples of a benzene ring fused to a heterocyclic ring include, but are not limited to benzofuran, isobenzofuran, dihydrobenzofuran, dihydrobenzopyran, benzoxazolidinone, benzimidazolinone, benzooxazinone, indole, isoindole, benzothiophene, quinoline, and isoquinoline. Unless otherwise specified, the heteroaryl and heterocyclic groups contain one or more heteroatoms selected from the group consisting of sulfur, nitrogen, and oxygen.

In one embodiment, $R^2$ is selected from the group consisting of $NR^7R^8$, optionally substituted imidazolyl, and optionally substituted alkyl. In a preferred embodiment, $R^2$ is $NR^7R^8$, and $R^7$ and $R^8$ are independently selected from the group consisting of hydrogen, alkyl, amino and alkylamino (including cyclic amines), alkylhydroxy, alkanoyl, alkoxy, alkoxycarbonyl, carbonyl, carboxyl, aralkyl, optionally substituted phenyl, heteroaryl, and $COR^9$ where $R^9$ is alkyl or aralkyl. In a preferred embodiment, $R^2$ is $NH_2$, -(dimethylamino)ethyl, or -(dimethylamino)propyl.

In another embodiment, $R^7$ and $R^8$ together form an optionally substituted 3 to 12 membered monocyclic or bicyclic ring containing 0 to 4 heteroatoms. In one embodiment, $R^2$ is an optionally substituted 5 to 6 membered heterocyclic group containing at least one nitrogen atom and 0 to 1 additional heteroatoms. $R^2$ can be, for example, an optionally substituted morpholinyl group, an optionally substituted piperazinyl group, or an optionally substituted pyrrolidinyl group.

In one embodiment, $R^2$ is $NR^7R^8$, and $R^2$ is selected from the groups listed as Set 2a:

Set 2a:

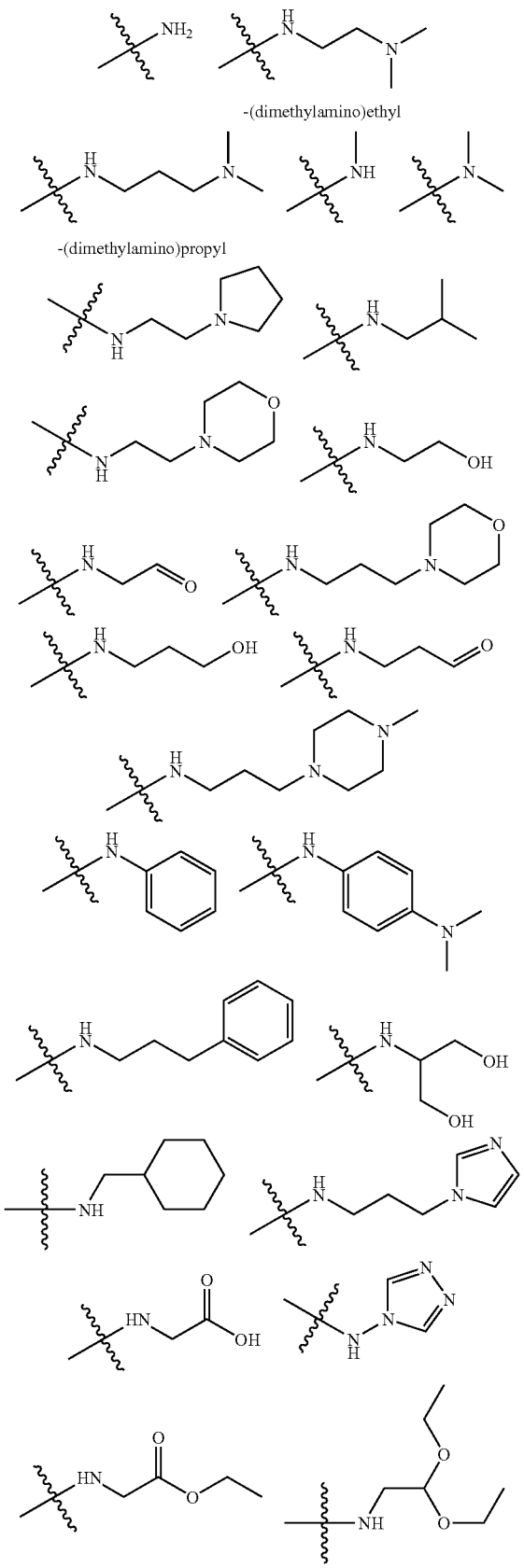

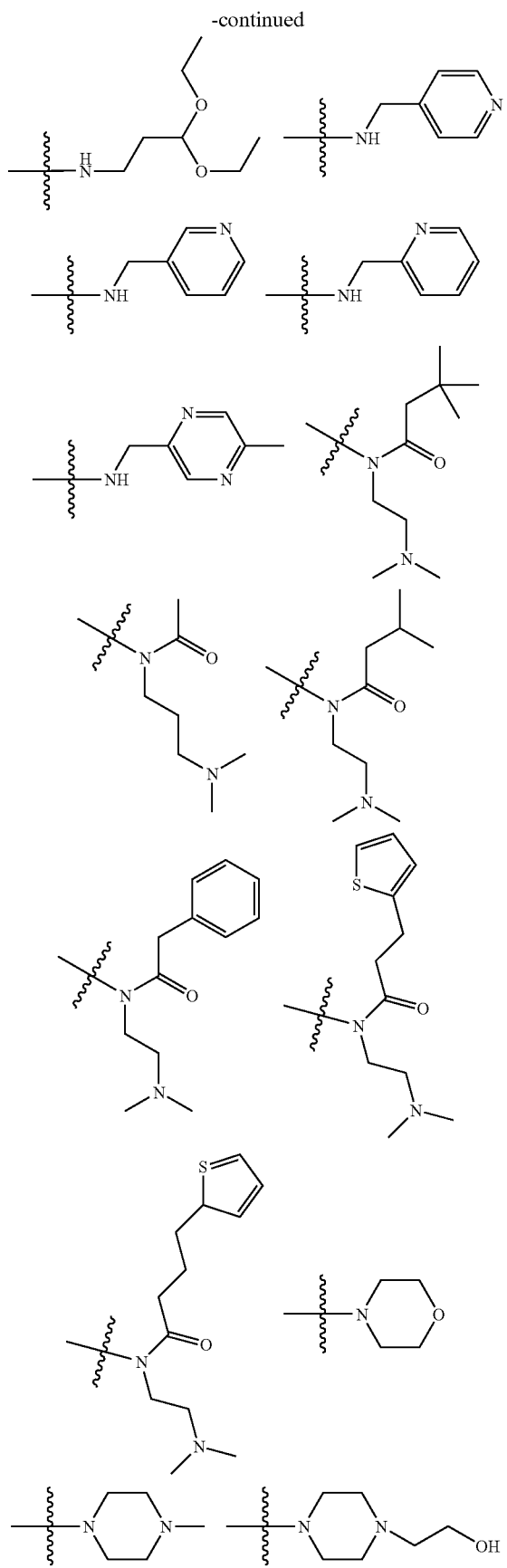
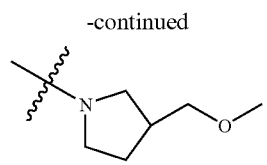

In another embodiment, $R^2$ is selected from the groups listed as Set 2b:

Set 2b:

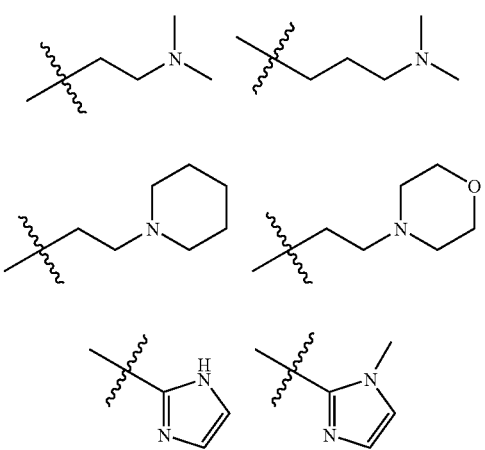

In one embodiment, the $SO_2R^2$ group is at position 3 of the phenyl ring. In another embodiment, the $SO_2R^2$ group is at position 4 of the phenyl ring such that the compound is a compound of formula II:

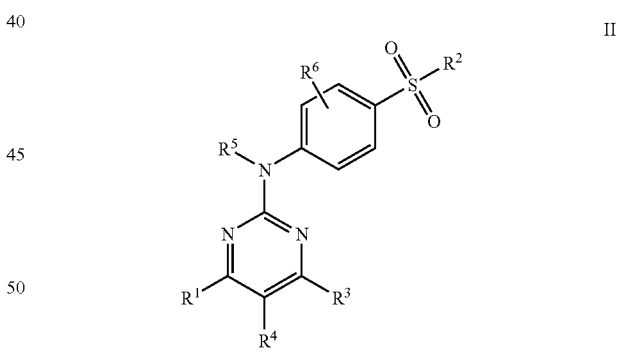

II

In one embodiment, $R^3$ is selected from the group consisting of an optionally substituted phenyl, an optionally substituted thienyl, an optionally substituted pyrazinyl, an optionally substituted pyrrolyl, a naphthyl group, bicyclo[2.2.1] heptene, and a benzene ring fused to a 5 to 7 membered ring containing 1 to 2 heteroatoms, optionally interrupted by a C=O group, and optionally substituted.

In one embodiment, $R^3$ is an optionally substituted phenyl group. Preferred substituents for this embodiment include alkoxy, trifluoromethyl, fluoro, hydroxy, and $NR^7R^8$ where $R^7$ is $COR^9$ and $R^8$ is hydrogen. In one embodiment, $R^3$ is selected from the groups listed as Set 3a:

Set 3a:
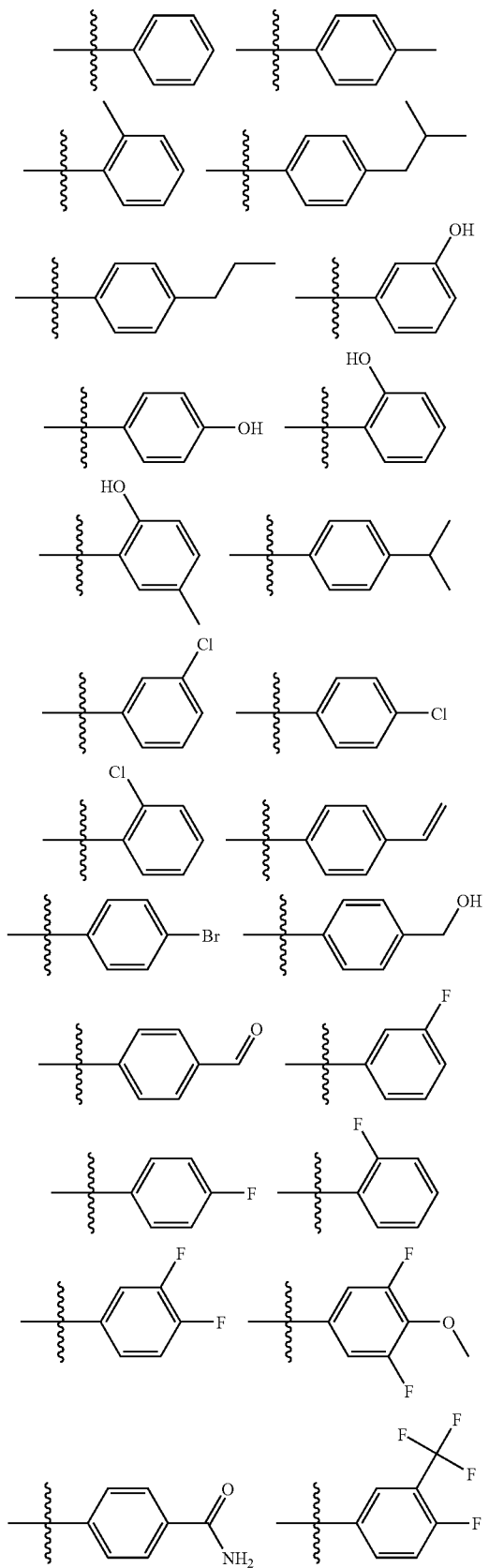
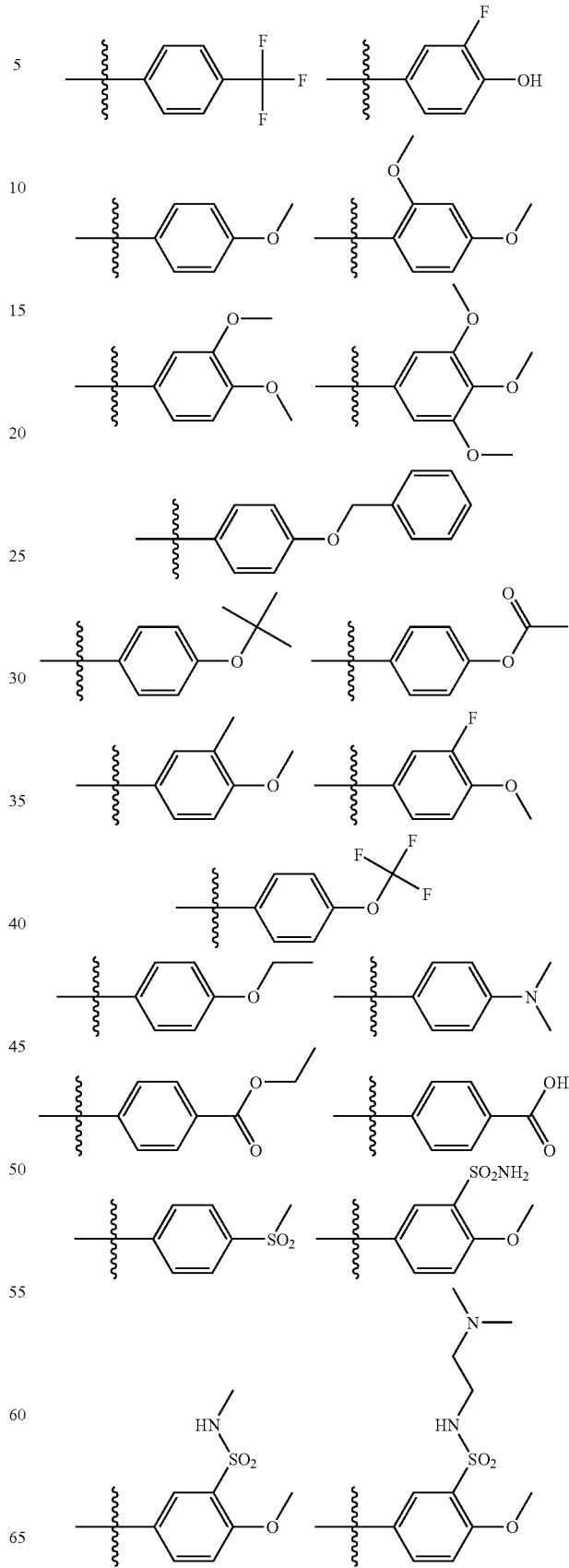

-continued
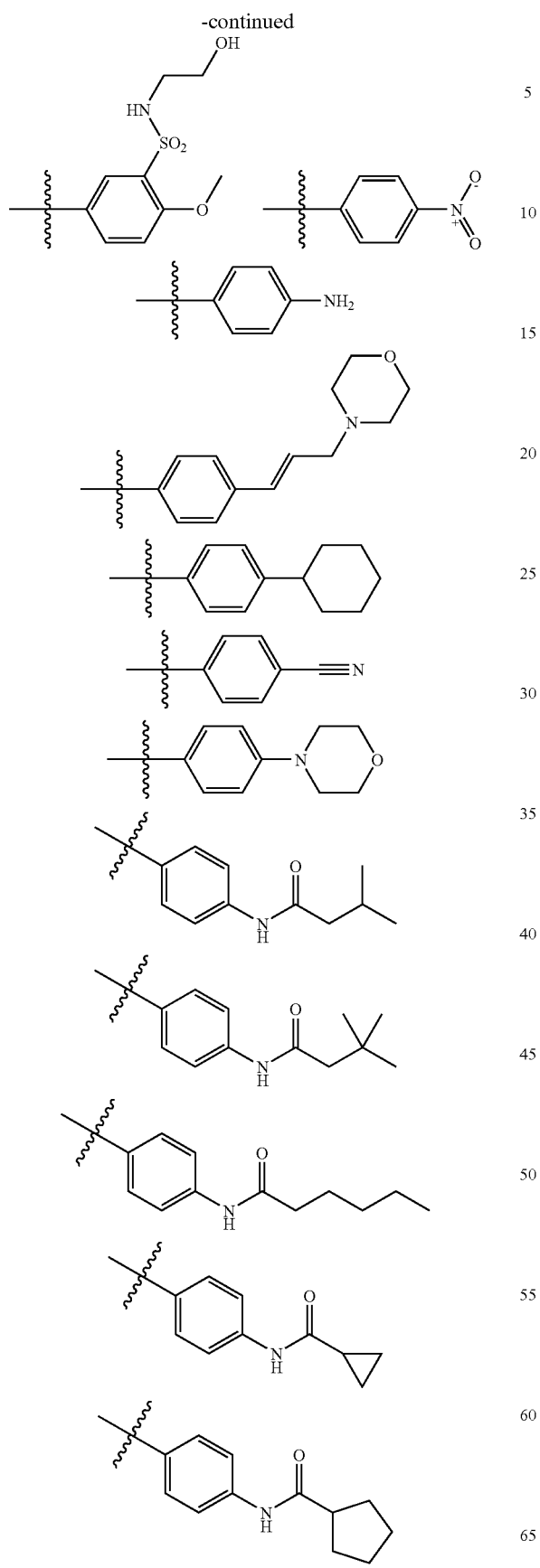
-continued
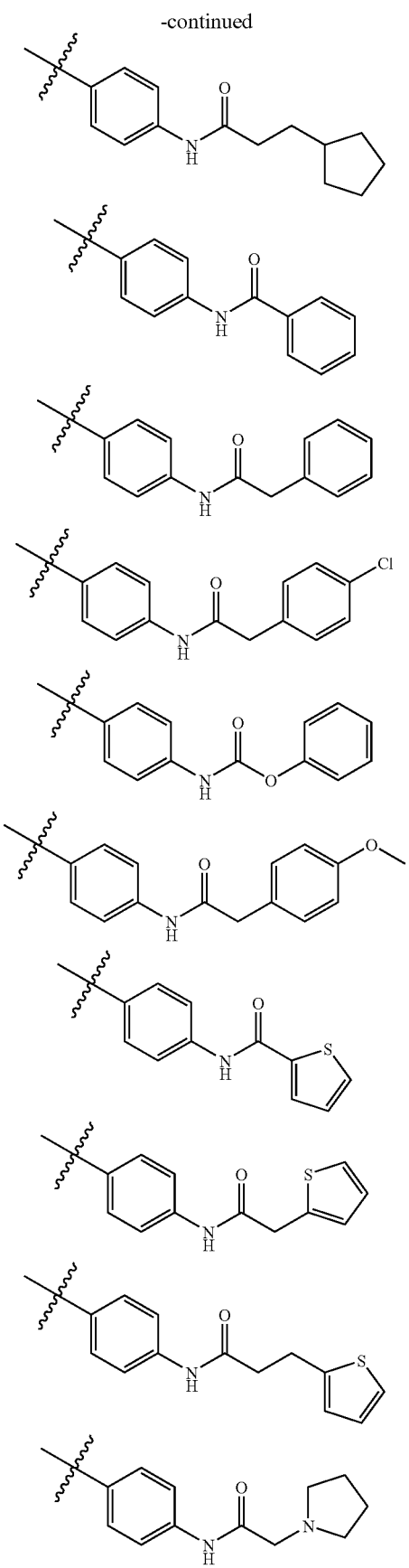

-continued
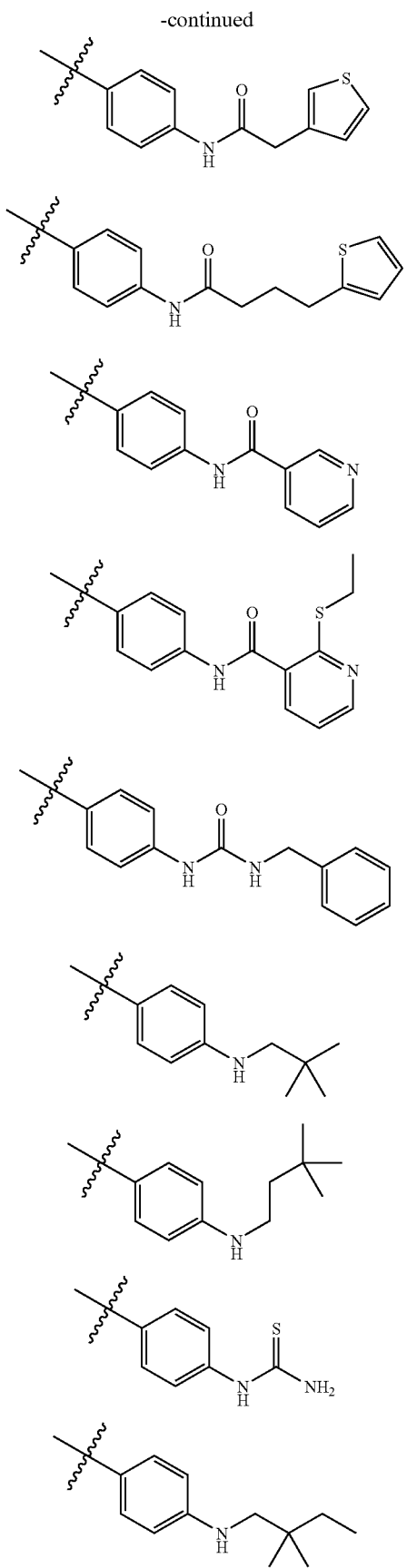
-continued
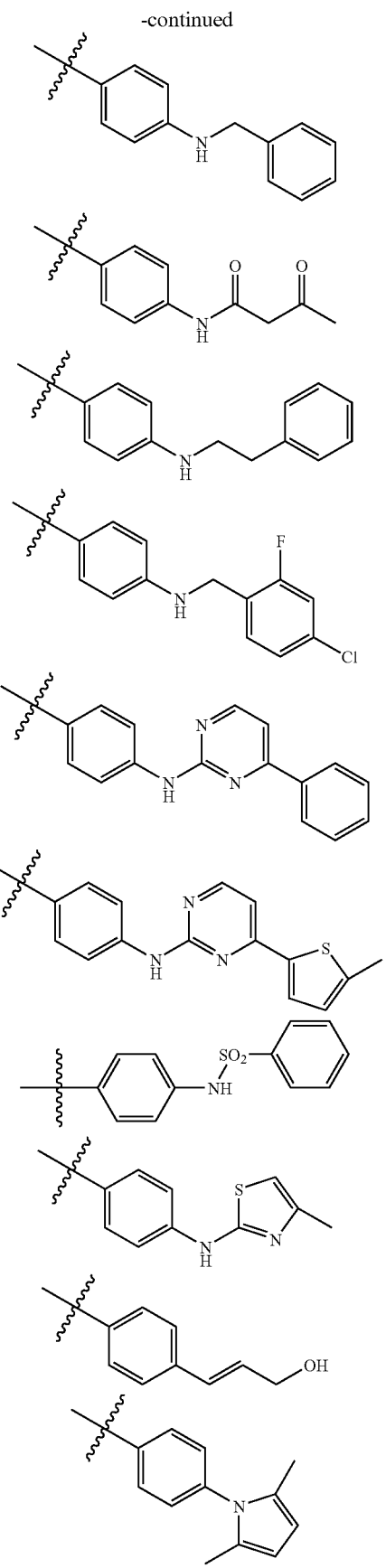

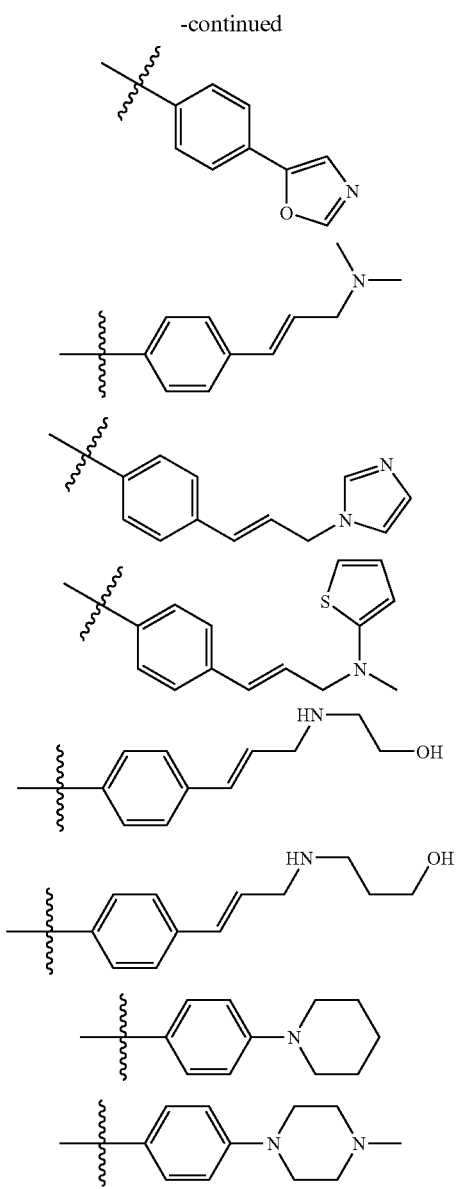
In one embodiment, $R^3$ is an optionally substituted thienyl group. Preferred substituents for this embodiment include hydrogen (i.e., an unsubstituted thienyl group), bromo, and methyl. In one embodiment, $R^3$ is selected from the groups listed as Set 3b:
Set 3b:
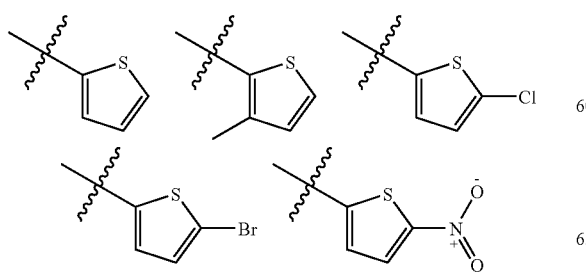
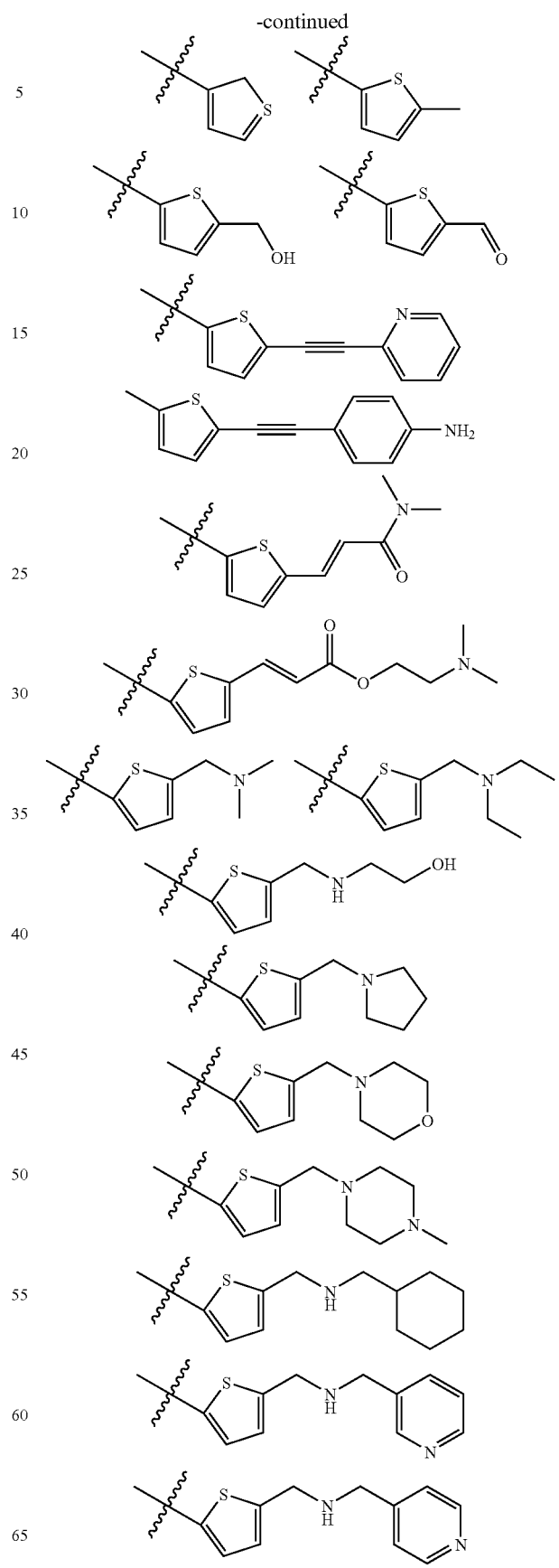

-continued

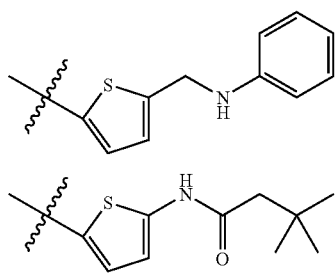

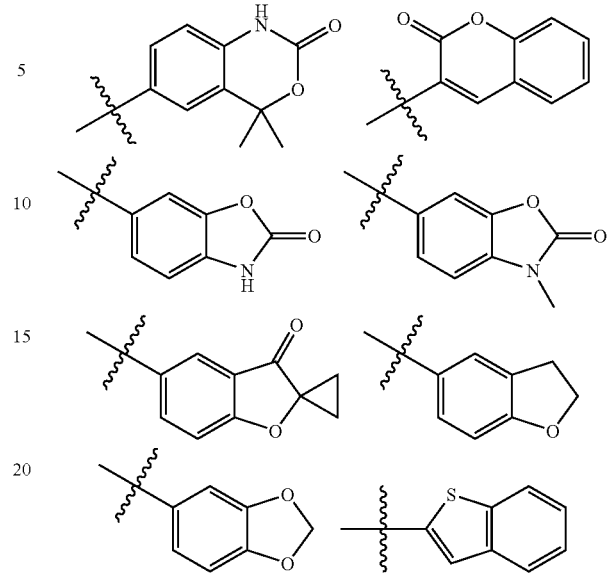

In another embodiment, $R^3$ is selected from the groups listed as Set 3c:

Set 3c:

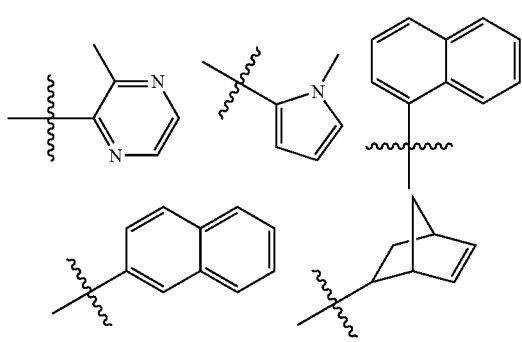

In one embodiment, $R^5$ is hydrogen or methyl. In a preferred embodiment, $R^5$ is hydrogen.

In one embodiment, $R^6$ is hydrogen, methyl, ethyl, chloro, methoxy, $NH_2$, or trifluoromethyl. In a preferred embodiment, $R^6$ is hydrogen.

Exemplary compounds of the present invention include the following compounds and salts, solvates, and hydrates thereof:

1. -[[4-(5-methyl-2-thienyl)-2-pyrim-idinyl]amino]-benzenesulfonamide
2. N-phenyl-4-[(4-thien-2-ylpyrimidin-2-yl)amino]benzenesulfonamide
3. N-methyl-4-[(4-thien-2-ylpyrimidin-2-yl)amino]benzenesulfonamide
4. 4-[4-(5-Chloro-thiophen-2-yl)-pyrimidin-2-ylamino]-benzenesulfonamide
5. 4-({4-[4-fluoro-3-(trifluoromethyl)phenyl]pyrimidin-2-yl}amino)benzenesulfonamide
6. 4-{[4-(4-methoxyphenyl)pyrimidin-2-yl]amino}-N,N-dimethylbenzenesulfonamide
7. 4-{[4-(3,4,5-trimethoxyphenyl)pyrimidin-2-yl]amino}benzenesulfonamide
8. 4-{[4-(3,4-difluorophenyl)pyrimidin-2-yl]amino}benzenesulfonamide
9. 4-[((4-thien-2-ylpyrimidin-2-yl)amino]benzenesulfonamide
10. 4-{[4-(5-nitrothien-2-yl)pyrimidin-2-yl]amino}benzenesulfonamide
11. 4-{[4-(4-methylphenyl)pyrimidin-2-yl]amino}benzenesulfonamide
12. 4-{[4-(2-methylphenyl)pyrimidin-2-yl]amino}benzenesulfonamide
13. 4-{[4-(3-methylthien-2-yl)pyrimidin-2-yl]amino}benzenesulfonamide
14. 4-{[4-(4-methoxy-3-methylphenyl)pyrimidin-2-yl]amino}benzenesulfonamide
15. 4-{[4-(2-hydroxyphenyl)pyrimidin-2-yl]amino}benzenesulfonamide
16. 4-{[4-(3-fluorophenyl)pyrimidin-2-yl]amino}benzenesulfonamide
17. 4-{[4-(2-hydroxy-5-methylphenyl)pyrimidin-2-yl]amino}benzenesulfonamide
18. 4-{[4-(3-hydroxyphenyl)pyrimidin-2-yl]amino}benzenesulfonamide
19. 4-{[4-(3-chlorophenyl)pyrimidin-2-yl]amino}benzenesulfonamide
20. 4-{[4-(2-chlorophenyl)pyrimidin-2-yl]amino}benzenesulfonamide
21. 4-{[4-(2-fluorophenyl)pyrimidin-2-yl]amino}benzenesulfonamide
22. 4-[(4-phenylpyrimidin-2-yl)amino]benzenesulfonamide
23. 4-{[4-(2,4-dimethoxyphenyl)pyrimidin-2-yl]amino}benzenesulfonamide
24. 4-[(4-bicyclo[2.2.1]hept-5-en-2-ylpyrimidin-2-yl)amino]benzenesulfonamide
25. 4-({4-[4-(trifluoromethyl)phenyl]pyrimidin-2-yl}amino)benzenesulfonamide
26. 4-{[4-(4-chlorophenyl)pyrimidin-2-yl]amino}benzenesulfonamide
27. 4-{[4-(4-cyclohexylphenyl)pyrimidin-2-yl]amino}benzenesulfonamide
28. 4-{[4-(4-cyanophenyl)pyrimidin-2-yl]amino}benzenesulfonamide
29. 4-{[4-(4-methoxyphenyl)pyrimidin-2-yl]amino}benzenesulfonamide
30. 4-{[4-(4-morpholin-4-ylphenyl)pyrimidin-2-yl]amino}benzenesulfonamide
31. 4-{[4-(4-isobutylphenyl)pyrimidin-2-yl]amino}benzenesulfonamide
32. 4-{[4-(4-propylphenyl)pyrimidin-2-yl]amino}benzenesulfonamide
33. 4-{[4-(4-isopropylphenyl)pyrimidin-2-yl]amino}benzenesulfonamide
34. 4-{[4-(4-vinylphenyl)pyrimidin-2-yl]amino}benzenesulfonamide
35. 4-[4-(5-Pyridin-2-ylethynyl-thiophen-2-yl)-pyrimidin-2-ylamino]-benzenesulfonamide
36. 4-[(4-{5-[(4-aminophenyl)ethynyl]thien-2-yl}pyrimidin-2-yl)amino]benzenesulfonamide -continued 37. (2E)-3-[5-(2-{[4-(aminosulfonyl)phenyl]amino}pyrimidin-4-yl)thien-2-yl]-N,N-dimethylacrylamide
38. 2-(dimethylamino)ethyl (2E)-3-[5-(2-{[4-(aminosulfonyl)phenyl]amino}pyrimidin-4-yl)thien-2-yl]acrylate
39. N-[4-(Morpholin-4-ylsulfonyl)phenyl]-4-[4-(trifluoromethyl)phenyl]pyrimidin-2-amine
40. N-(3-morpholin-4-ylpropyl)-4-({4-[4-(trifluoromethyl)phenyl]pyrimidin-2-yl}amino)benzenesulfonamide
41. 4-{[4-(4-methoxyphenyl)pyrimidin-2-yl]amino}-N-(3-morpholin-4-ylpropyl)benzenesulfonamide
42. 4-{[4-(4-methylphenyl)pyrimidin-2-yl]amino}-N-(3-morpholin-4-ylpropyl)benzenesulfonamide
43. 2-{4-[(4-{[4-(4-methoxyphenyl)pyrimidin-2-yl]amino}phenyl)sulfonyl]piperazin-1-yl}ethanol
44. 4-({4-[4-(methylsulfonyl)phenyl]pyrimidin-2-yl}amino)-N-(3-morpholin-4-ylpropyl)benzenesulfonamide
45. 4-{[4-(1,3-benzodioxol-5-yl)pyrimidin-2-yl]amino}-N-(3-morpholin-4-ylpropyl)benzenesulfonamide
46. N-(3-morpholin-4-ylpropyl)-4-({4-[4-(trifluoromethoxy)phenyl]pyrimidin-2-yl}amino)benzenesulfonamide
47. 4-{[4-(3,4-dimethoxyphenyl)pyrimidin-2-yl]amino}-N-(3-morpholin-4-ylpropyl)benzenesulfonamide
48. 4-{[4-(3-fluoro-4-methoxyphenyl)pyrimidin-2-yl]amino}-N-(3-morpholin-4-ylpropyl)benzenesulfonamide
49. 4-{[4-(3,4-dimethoxyphenyl)pyrimidin-2-yl]amino}-N-(2-morpholin-4-ylethyl)benzenesulfonamide
50. N-(2-morpholin-4-ylethyl)-4-({4-[4-(trifluoromethoxy)phenyl]pyrimidin-2-yl}amino)benzenesulfonamide
51. 4-({4-[4-(methylsulfonyl)phenyl]pyrimidin-2-yl}amino)-N-(2-morpholin-4-ylethyl)benzenesulfonamide
52. 4-{[4-(3-fluoro-4-methoxyphenyl)pyrimidin-2-yl]amino}-N-(2-morpholin-4-ylethyl)benzenesulfonamide
53. 4-{[4-(4-fluorophenyl)pyrimidin-2-yl]amino}-N-(2-morpholin-4-ylethyl)benzenesulfonamide
54. 4-{[4-(4-bromophenyl)pyrimidin-2-yl]amino}-N-(2-morpholin-4-ylethyl)benzenesulfonamide
55. 4-{[4-(4-methoxyphenyl)pyrimidin-2-yl]amino}-N-(2-morpholin-4-ylethyl)benzenesulfonamide
56. 4-{[4-(1,3-benzodioxol-5-yl)pyrimidin-2-yl]amino}-N-(2-morpholin-4-ylethyl)benzenesulfonamide
57. 4-{[4-(4-hydroxyphenyl)pyrimidin-2-yl]amino}-N-(2-morpholin-4-ylethyl)benzenesulfonamide
58. 4-{[4-(4-chlorophenyl)pyrimidin-2-yl]amino}-N-(2-morpholin-4-ylethyl)benzenesulfonamide
59. 4-{[4-(4-chlorophenyl)pyrimidin-2-yl]amino}-N-[3-(dimethylamino)propyl]benzenesulfonamide
60. N-[3-(dimethylamino)propyl]-4-({4-[4-(methylsulfonyl)phenyl]pyrimidin-2-yl}amino)benzenesulfonamide
61. N-[2-(dimethylamino)ethyl]-4-{[4-(4-methoxyphenyl)pyrimidin-2-yl]amino}benzenesulfonamide
62. N-[2-(dimethylamino)ethyl]-4-{[4-(3-fluoro-4-methoxyphenyl)pyrimidin-2-yl]amino}benzenesulfonamide
63. N-[2-(dimethylamino)ethyl]-4-({4-[4-(methylsulfonyl)phenyl]pyrimidin-2-yl}amino)benzenesulfonamide
64. 4-{[4-(4-chlorophenyl)pyrimidin-2-yl]amino}-N-[2-(dimethylamino)ethyl]benzenesulfonamide
65. N-[3-(dimethylamino)propyl]-4-{[4-(4-hydroxyphenyl)pyrimidin-2-yl]amino}benzenesulfonamide
66. N-[2-(dimethylamino)ethyl]-4-{[4-(4-hydroxyphenyl)pyrimidin-2-yl]amino}benzenesulfonamide
67. N-morpholin-4-yl-4-({4-[4-(trifluoromethyl)phenyl]pyrimidin-2-yl}amino)benzenesulfonamide
68. N-(3-hydroxypropyl)-4-({4-[4-(trifluoromethyl)phenyl]pyrimidin-2-yl}amino)-benzenesulfonamide
69. 3-{[4-(3-methylpyrazin-2-yl)pyrimidin-2-yl]amino}benzenesulfonamide
70. 3-({4-[4-(methylsulfonyl)phenyl]pyrimidin-2-yl)amino]benzenesulfonamide
71. N-isobutyl-4-[(4-thien-3-ylpyrimidin-2-yl)amino]benzenesulfonamide
72. 4-{[4-(1-methyl-1H-pyrrol-2-yl)pyrimidin-2-yl]amino}-N-phenylbenzenesulfonamide
73. N-methyl-4-{[4-(1-methyl-1H-pyrrol-2-yl)pyrimidin-2-yl]amino}benzenesulfonamide
74. N-isobutyl-4-{[4-(1-methyl1H-pyrrol-2-yl)pyrimidin-2-yl]amino}benzenesulfonamide
75. 4-{[4-(5-bromothien-2-yl)pyrimidin-2-yl]amino}-N-methylbenzenesulfonamide
76. N-[4-(dimethylamino)phenyl]-4-{[4-(1-naphthyl)pyrimidin-2-yl]amino}benzenesulfonamide
77. N-(4-{[2-(methoxymethyl)pyrrolidin-1-yl]sulfonyl}phenyl)-4-(1-naphthyl)pyrimidin-2-amine
78. N-methyl-4-{[4-(3-methylthien-2-yl)pyrimidin-2-yl]amino}benzenesulfonamide
79. N-isobutyl-4-{[4-(3-methylthien-2-yl)pyrimidin-2-yl]amino}benzenesulfonamide -continued 80. N-(4-{[(2S)-2-(methoxymethyl)pyrrolidin-1-yl]sulfonyl}phenyl)-N-methyl-4-(2-thienyl)pyrimidin-2-amine
81. 4-{methyl[4-(5-methyl-2-thienyl)pyrimidin-2-yl]amino}benzenesulfonamide
82. 4-[[4-(5-bromo-2-thienyl)pyrimidin-2-yl](methyl)amino]benzenesulfonamide
83. N-methyl-4-{methyl[4-(5-methyl-2-thienyl)pyrimidin-2-yl]amino}benzenesulfonamide
84. N-methyl-4-{methyl[4-(2-thienyl)pyrimidin-2-yl]amino}benzenesulfonamide
85. 4-[[4-(5-bromo-2-thienyl)pyrimidin-2-yl](methyl)amino]-N-methylbenzenesulfonamide
86. N-methyl-3-{[4-(2-naphthyl)pyrimidin-2-yl]amino}benzenesulfonamide
87. N-isobutyl-3-{[4-(2-naphthyl)pyrimidin-2-yl]amino}benzenesulfonamide
88. 4-{[4-(5-bromo-2-thienyl)pyrimidin-2-yl]amino}benzenesulfonamide
89. ethyl 4-(2-[(4-{[(3-morpholin-4-ylpropyl)amino]sulfonyl}phenyl)amino]pyrimidin-4-yl}benzoate
90. 4-{[4-(5-methylthien-2-yl)pyrimidin-2-yl]amino}-N-(3-morpholin-4-ylpropyl)benzenesulfonamide
91. 4-{[4-(4-ethoxyphenyl)pyrimidin-2-yl]amino}-N-(3-morpholin-4-ylpropyl)benzenesulfonamide
92. 4-({4-[4-(dimethylamino)phenyl]pyrimidin-2-yl}amino)-N-(3-morpholin-4-ylpropyl)benzenesulfonamide
93. 5-(2-{[4-(aminosulfonyl)phenyl]amino}pyrimidin-4-yl)-2-methoxybenzenesulfonamide
94. 4-{2-[(4-{[(3-morpholin-4-ylpropyl)amino]sulfonyl}phenyl)amino]pyrimidin-4-yl}benzoic acid
95. N-[2-(dimethylamino)ethyl]-5-(2-{[4-({[2-(dimethylamino)ethyl]amino}sulfonyl)phenyl]amino}pyrimidin-4-yl)-2-methoxybenzenesulfonamide
96. 2-methoxy-N-methyl-5-[2-({4-[(methylamino)sulfonyl]phenyl}amino)pyrimidin-4-yl]benzenesulfonamide
97. N-(2-hydroxyethyl)-5-{2-[(4-{[(2-hydroxyethyl)amino]sulfonyl}phenyl)amino]pyrimidin-4-yl}-2-methoxybenzenesulfonamide
98. 4-(4-methoxyphenyl)-N-{4-[(2-piperidin-1-ylethyl)sulfonyl]phenyl}pyrimidin-2-amine
99. 4-(4-methoxyphenyl)-N-{4-[(2-morpholin-4-ylethyl)sulfonyl]phenyl}pyrimidin-2-amine
100. 4-(3-fluoro-4-methoxyphenyl)-N-{4-[(2-morpholin-4-ylethyl)sulfonyl]phenyl}pyrimidin-2-amine
101. N-(4-{[3-(dimethylamino)propyl]sulfonyl}phenyl)-4-(4-methoxyphenyl)pyrimidin-2-amine
102. N-(4-{[3-(dimethylamino)propyl]sulfonyl}phenyl)-4-(3-fluoro-4-methoxyphenyl)pyrimidin-2-amine
103. 4-(3-fluoro-4-methoxyphenyl)-N-{4-[(2-piperidin-1-ylethyl)sulfonyl]phenyl}pyrimidin-2-amine
104. 4-{[4-(4-hydroxyphenyl)pyrimidin-2-yl]amino}benzenesulfonamide
105. 4-{[4-(5-bromo-2-thienyl)pyrimidin-2-yl]amino}-N-[2-(dimethylamino)ethyl]benzenesulfonamide
106. 4-{[4-(4,4-dimethyl-2-oxo-1,4-dihydro-2H-3,1-benzoxazin-6-yl)pyrimidin-2-yl]amino}benzenesulfonamide
107. 4-{[4-(3,5-difluoro-4-methoxyphenyl)pyrimidin-2-yl]amino}benzenesulfonamide
108. 4-{[4-(2-oxo-2H-chromen-3-yl)pyrimidin-2-yl]amino}benzenesulfonamide
109. 4-{[4-(3-methyl-2-oxo-2,3-dihydro-1,3-benzoxazol-6-yl)pyrimidin-2-yl]amino}benzenesulfonamide
110. 4-{[4-(2-oxo-2,3-dihydro-1,3-benzoxazol-6-yl)pyrimidin-2-yl]amino}benzenesulfonamide
111. N-[2-(dimethylamino)ethyl]-4-({4-[4-(trifluoromethyl)phenyl]pyrimidin-2-yl}amino)benzenesulfonamide
112. N-[3-(dimethylamino)propyl]-4-({4-[4-(trifluoromethyl)phenyl]pyrimidin-2-yl}amino)benzenesulfonamide
113. N-[3-(1H-imidazol-1-yl)propyl]-4-({4-[4-(trifluoromethyl)phenyl]pyrimidin-2-yl}amino)benzenesulfonamide
114. N-4H-1,2,4-triazol-4-yl-4-({4-[4-(trifluoromethyl)phenyl]pyrimidin-2-yl}amino)benzenesulfonamide
115. N-[3-(dimethylamino)propyl]-3-{[4-(3-fluoro-4-methoxyphenyl)pyrimidin-2-yl]amino}benzenesulfonamide
116. N-[3-(dimethylamino)propyl]-3-{[4-(4-methoxyphenyl)pyrimidin-2-yl]amino}benzenesulfonamide
117. N-[2-(dimethylamino)ethyl]-3-{[4-(3-fluoro-4-methoxyphenyl)pyrimidin-2-yl]amino}benzenesulfonamide
118. N-[2-(dimethylamino)ethyl]-3-{[4-(4-methoxyphenyl)pyrimidin-2-yl]amino}benzenesulfonamide
119. N-(2-morpholin-4-ylethyl)-4-({4-[4-(trifluoromethyl)phenyl]pyrimidin-2-yl}amino)benzenesulfonamide
120. N-[2-hydroxy-1-(hydroxymethyl)ethyl]-4-({4-[4-(trifluoromethyl)phenyl]pyrimidin-2-yl}amino)benzenesulfonamide
121. N-(2-hydroxyethyl)-4-({4-[4-(trifluoromethyl)phenyl]pyrimidin-2-yl}amino)benzenesulfonamide
122. ethyl N-{[4-({4-[4-(trifluoromethyl)phenyl]pyrimidin-2-yl}amino)phenyl]sulfonyl}glycinate -continued 123. N-[3-(dimethylamino)propyl]-3-{[4-(4-hydroxyphenyl)pyrimidin-2-yl]amino}benzenesulfonamide
124. N-{[4-({4-[4-(trifluoromethyl)phenyl]pyrimidin-2-yl}amino)phenyl]sulfonyl}glycine
125. 3-{[4-(3-fluoro-4-methoxyphenyl)pyrimidin-2-yl]amino}benzenesulfonamide
126. N-[3-(dimethylamino)propyl]-4-{[4-(3-fluoro-4-methoxyphenyl)pyrimidin-2-yl]amino}benzenesulfonamide
127. 3-{[4-(3-fluoro-4-methoxyphenyl)pyrimidin-2-yl]amino}-N-(3-phenylpropyl)benzenesulfonamide
128. N-(cyclohexylmethyl)-3-{[4-(3-fluoro-4-methoxyphenyl)pyrimidin-2-yl]amino}benzenesulfonamide
129. 3-{[4-(3-fluoro-4-hydroxyphenyl)pyrimidin-2-yl]amino}benzenesulfonamide
130. N-[2-(dimethylamino)ethyl]-4-{[4-(3-fluoro-4-hydroxyphenyl)pyrimidin-2-yl]amino}benzenesulfonamide
131. N-[3-(dimethylamino)propyl]-4-{[4-(3-fluoro-4-hydroxyphenyl)pyrimidin-2-yl]amino}benzenesulfonamide
132. 4-({4-[5-(hydroxymethyl)-2-thienyl]pyrimidin-2-yl}amino)benzenesulfonamide
133. 4-{[4-(5-formyl-2-thienyl)pyrimidin-2-yl]amino}benzenesulfonamide
134. 4-({4-[5-(morpholin-4-ylmethyl)-2-thienyl]pyrimidin-2-yl}amino)benzenesulfonamide
135. N-[(5-methylpyrazin-2-yl)methyl]-4-({4-[4-(trifluoromethyl)phenyl]pyrimidin-2-yl}amino)benzenesulfonamide
136. N-(pyridin-2-ylmethyl)-4-({4-[4-(trifluoromethyl)phenyl]pyrimidin-2-yl}amino)benzenesulfonamide
137. N-(pyridin-3-ylmethyl)-4-({4-[4-(trifluoromethyl)phenyl]pyrimidin-2-yl}amino)benzenesulfonamide
138. N-(pyridin-4-ylmethyl)-4-({4-[4-(trifluoromethyl)phenyl]pyrimidin-2-yl}amino)benzenesulfonamide
139. 4-{[4-(3-fluoro-4-methoxyphenyl)pyrimidin-2-yl]amino}-N-(3-hydroxypropyl)benzenesulfonamide
140. 4-(4-methoxyphenyl)-N-{4-[(1-methyl-1H-imidazol-2-yl)sulfonyl]phenyl}pyrimidin-2-amine
141. 4-({4-[5-(pyrrolidin-1-ylmethyl)-2-thienyl]pyrimidin-2-yl}amino)benzenesulfonamide
142. 4-[(4-{5-[(dimethylamino)methyl]-2-thienyl}pyrimidin-2-yl)amino]benzenesulfonamide
143. 4-[(4-{5-[(diethylamino)methyl]-2-thienyl}pyrimidin-2-yl)amino]benzenesulfonamide
144. 4-{[4-(5-{[(2-hydroxyethyl)amino]methyl}-2-thienyl)pyrimidin-2-yl]amino}benzenesulfonamide
145. 4-[(4-{5-[(4-methylpiperazin-1-yl)methyl]-2-thienyl}pyrimidin-2-yl)amino]benzenesulfonamide
146. 4-{[4-(5-{[(pyridin-3-ylmethyl)amino]methyl}-2-thienyl)pyrimidin-2-yl]amino}benzenesulfonamide
147. 4-{[4-(5-{[(pyridin-4-ylmethyl)amino]methyl}-2-thienyl)pyrimidin-2-yl]amino}benzenesulfonamide
148. 4-{[4-(5-{[(cyclohexylmethyl)amino]methyl}-2-thienyl)pyrimidin-2-yl]amino}benzenesulfonamide
149. 4-({4-[5-(anilinomethyl)-2-thienyl]pyrimidin-2-yl}amino)benzenesulfonamide
150. 4-[2-({4-[(1-methyl-1H-imidazol-2-yl)sulfonyl]phenyl}amino)pyrimidin-4-yl]phenol
151. N-[4-(2-{[4-(aminosulfonyl)phenyl]amino}pyrimidin-4-yl)phenyl]-3-cyclopentylpropanamide
152. N-[4-(2-{[4-(aminosulfonyl)phenyl]amino}pyrimidin-4-yl)phenyl]-2-phenylacetamide
153. N-[4-(2-{[4-(aminosulfonyl)phenyl]amino}pyrimidin-4-yl)phenyl]-2-(2-thienyl)acetamide
154. N-[4-(2-{[4-(aminosulfonyl)phenyl]amino}pyrimidin-4-yl)phenyl]nicotinamide
155. N-[4-(2-{[4-(aminosulfonyl)phenyl]amino}pyrimidin-4-yl)phenyl]-2-(ethylthio)nicotinamide
156. N-[4-(2-{[4-(aminosulfonyl)phenyl]amino}pyrimidin-4-yl)phenyl]hexanamide
157. N-[4-(2-{[4-(aminosulfonyl)phenyl]amino}pyrimidin-4-yl)phenyl]cyclopropanecarboxamide
158. N-[4-(2-{[4-(aminosulfonyl)phenyl]amino}pyrimidin-4-yl)phenyl]cyclopentanecarboxamide
159. 4-(2-{[4-(1H-imidazol-2-ylsulfonyl)phenyl]amino}pyrimidin-4-yl)phenol
160. 2-chloro-5-{[4-(3-fluoro-4-methoxyphenyl)pyrimidin-2-yl]amino}benzenesulfonamide
161. N-[2-(dimethylamino)ethyl]-2-ethyl-4-{[4-(3-fluoro-4-methoxyphenyl)pyrimidin-2-yl]amino}benzenesulfonamide
162. N-[2-(dimethylamino)ethyl]-2-ethyl-4-{[4-(4-methoxyphenyl)pyrimidin-2-yl]amino}benzenesulfonamide
163. N-[3-(dimethylamino)propyl]-2-ethyl-4-{[4-(3-fluoro-4-methoxyphenyl)pyrimidin-2-yl]amino}benzenesulfonamide
164. N-[3-(dimethylamino)propyl]-2-ethyl-4-{[4-(4-methoxyphenyl)pyrimidin-2-yl]amino}benzenesulfonamide
165. 2-chloro-5-{[4-(4,4-dimethyl-2-oxo-1,4-dihydro-2H-3,1-benzoxazin-6-yl)pyrimidin-2-yl]amino}benzenesulfonamide
166. N-[3-(dimethylamino)propyl]-4-{[4-(3-fluoro-4-methoxyphenyl) pyrimidin-2-yl]amino}-2-(trifluoromethyl)benzenesulfonamide-
167. N-[2-(dimethylamino)ethyl]-4-{[4-(3-fluoro-4-methoxyphenyl) pyrimidin-2-yl]amino}-2-(trifluoromethyl)benzenesulfonamide
168. N-[3-(dimethylamino)propyl]-4-{[4-(4-methoxyphenyl)pyrimidin-2-yl]amino}-2-(trifluoromethyl)benzenesulfonamide -continued 169. N-[2-(dimethylamino)ethyl]-4-{[4-(4-methoxyphenyl)pyrimidin-2-yl]amino}-2-(trifluoromethyl)benzenesulfonamide
170. 4-(3-fluoro-4-methoxyphenyl)-N-{4-[(1-methyl-1H-imidazol-2-yl)sulfonyl]phenyl}pyrimidin-2-amine
171. 2-chloro-N-[2-(dimethylamino)ethyl]-4-{[4-(3-fluoro-4-methoxyphenyl)pyrimidin-2-yl]amino}benzenesulfonamide
172. 2-chloro-N-[2-(dimethylamino)ethyl]-4-{[4-(4-methoxyphenyl)pyrimidin-2-yl]amino}benzenesulfonamide
173. 2-chloro-N-[3-(dimethyiamino)propyl]-4-{[4-(3-fluoro-4-methoxyphenyl)pyrimidin-2-yl]amino}benzenesulfonamide
174. 2-chloro-N-[3-(dimethylamino)propyl]-4-{[4-(4-methoxyphenyl)pyrimidin-2-yl]amino}benzenesulfonamide
175. 3-{[4-(4,4-dimethyl-2-oxo-1,4-dihydro-2H-3,1-benzoxazin-6-yl)pyrimidin-2-yl]amino}benzenesulfonamide
176. 5-{[4-(3-fluoro-4-methoxyphenyl)pyrimidin-2-yl]amino}-2-methylbenzenesulfonamide
177. N-{4-[(1-methyl-1H-imidazol-2-yl)sulfonyl]phenyl}-4-[5-(pyrrolidin-1-ylmethyl)-2-thienyl]pyrimidin-2-amine
178. N-{4-[(1-methyl-1H-imidazol-2-yl)sulfonyl]phenyl}-4-{5-[(4-methylpiperazin-1-yl)methyl]-2-thienyl}pyrimidin-2-amine
179. 4-[4-(benzyloxy)phenyl]-N-{4-[(1-methyl-1H-imidazol-2-yl)sulfonyl]phenyl}pyrimidin-2-amine
180. N-{4-[(4-methylpiperazin-1-yl)sulfonyl]phenyl}-4-(4-nitrophenyl)pyrimidin-2-amine
181. 4-(4-aminophenyl)-N-{4-[(4-methylpiperazin-1-yl)sulfonyl]phenyl}pyrimidin-2-amine
182. N-[3-(dimethylamino)propyl]-4-{[4-(4-nitrophenyl)pyrimidin-2-yl]amino}benzenesulfonamide
183. 4-{[4-(4-aminophenyl)pyrimidin-2-yl]amino}-N-[3-(dimethylamino)propyl]benzenesulfonamide
184. N-[2-(dimethylamino)ethyl]-4-{[4-(3-fluoro-4-methoxyphenyl) pyrimidin-2-yl]amino}-2-methoxybenzenesulfonamide
185. N-[4-(2-{[4-({[3-(dimethylamino)propyl]amino}sulfonyl)phenyl]amino}pyrimidin-4-yl)phenyl]-2-(2-thienyl)acetamide
186. N-[2-(dimethylamino)ethyl]-4-{[4-(4-nitrophenyl)pyrimidin-2-yl]amino}benzenesulfonamide
187. phenyl [4-(2-{[4-({[3-(dimethylamino)propyl]amino} sulfonyl)phenyl]amino}pyrimidin-4-yl)phenyl]carbamate
188. N-{4-[2-({4-[(4-methylpiperazin-1-yl)sulfonyl]phenyl}amino) pyrimidin-4-yl]phenyl}-2-(2-thienyl)acetamide
189. 4-{[4-(4-aminophenyl)pyrimidin-2-yl]amino}-N-[2-(dimethylamino)ethyl]benzenesulfonamide
190. N-[4-(2-{[4-({[2-(dimethylamino)ethyl]amino}sulfonyl) phenyl]amino}pyrimidin-4-yl)phenyl]-2-(2-thienyl)acetamide
191. N-[2-(dimethylamino)ethyl]-4-{[4-(3-thienyl)pyrimidin-2-yl]amino}benzenesulfonamide
192. N-[3-(dimethylamino)propyl]-4-{[4-(3-thienyl)pyrimidin-2-yl]amino}benzenesulfonamide
193. N-(2-hydroxyethyl)-4-{[4-(3-thienyl)pyrimidin-2-yl]amino}benzenesulfonamide
194. N-[4-(2-{[4-({[3-(dimethylamino)propyl]amino}sulfonyl) phenyl]amino}pyrimidin-4-yl)phenyl]-3-methylbutanamide
195. N-[4-(2-{[4-({[3-(dimethylamino)propyl]amino}sulfonyl)phenyl]amino}pyrimidin-4-yl)phenyl]-2-phenylacetamide
196. N-[4-(2-{[4-({[3-(dimethylamino)propyl]amino}sulfonyl)phenyl]amino}pyrimidin-4-yl)phenyl]-2-(4-methoxyphenyl)acetamide
197. N-[4-(2-{[4-({[3-(dimethylamino)propyl]amino}sulfonyl) phenyl]amino}pyrimidin-4-yl)phenyl]-3-(2-thienyl)propanamide
198. N-[4-(2-{[4-({[3-(dimethylamino)propyl]amino}sulfonyl)phenyl]amino}pyrimidin-4-yl)phenyl]-3,3-dimethylbutanamide
199. N-[4-(2-{[4-({[3-(dimethylamino)propyl]amino}sulfonyl)phenyl]amino}pyrimidin-4-yl)phenyl]thiophene-2-carboxamide
200. N-[4-(2-{[4-({[3-(dimethylamino)propyl]amino}sulfonyl)phenyl]amino}pyrimidin-4-yl)phenyl]-4-(2-thienyl)butanamide
201. 3,3-dimethyl-N-{4-[2-({4-[(4-methylpiperazin-1-yl)sulfonyl]phenyl}amino)pyrimidin-4-yl]phenyl}butanamide
202. N-[4-(2-{[4-({[3-(dimethylamino)propyl]amino}sulfonyl)phenyl]amino}pyrimidin-4-yl)phenyl]-2-(3-thienyl)acetamide
203. N-[4-(2-{[4-({[2-(dimethylamino)ethyl]amino}sulfonyl)phenyl]amino}pyrimidin-4-yl)phenyl]-3,3-dimethylbutanamide
204. N-[4-(2-{[4-({[2-(dimethylamino)ethyl]amino}sulfonyl)phenyl]amino}pyrimidin-4-yl)phenyl]-2-phenylacetamide
205. N-[2-(dimethylamino)ethyl]-N-({4-[(4-{4-[(3,3-dimethylbutanoyl)amino]phenyl}pyrimidin-2-yl)amino]phenyl}sulfonyl)-3,3-dimethylbutanamide
206. N-[4-(2-{[4-({[2-(dimethylamino)ethyl]amino}sulfonyl)phenyl]amino}pyrimidin-4-yl)phenyl]thiophene-2-carboxamide
207. N-[3-(dimethylamino)propyl]-4-[(4-{4-[(phenylsulfonyl)amino]phenyl}pyrimidin-2-yl)amino]benzenesulfonamide
208. N-[4-(2-{[4-({[2-(dimethylamino)ethyl]amino}sulfonyl)phenyl]amino}pyrimidin-4-yl)phenyl]-2-(4-methoxyphenyl)acetamide
209. N-[4-(2-{[4-({[2-(dimethylamino)ethyl]amino}sulfonyl)phenyl]amino}pyrimidin-4-yl)phenyl]-2-(3-thienyl)acetamide -continued 210. N-[4-(2-{[4-({[2-(dimethylamino)ethyl]amino}sulfonyl)phenyl]amino}pyrimidin-4-yl)phenyl]-4-(2-thienyl)butanamide
211. N-{4-[2-({4-[(4-methylpiperazin-1-yl)sulfonyl]phenyl}amino) pyrimidin-4-yl]phenyl}thiophene-2-carboxamide
212. N-{4-[2-({4-[(4-methylpiperazin-1-yl)sulfonyl]phenyl}amino) pyrimidin-4-yl]phenyl}-2-(3-thienyl)acetamide
213. N-{4-[2-({4-[(4-methylpiperazin-1-yl)sulfonyl]phenyl}amino) pyrimidin-4-yl]phenyl}-2-phenylacetamide
214. N-[2-(dimethylamino)ethyl]-4-(2-thienyl)-N-[(4-{[4-(4-{[4-(2-thienyl)butanoyl]amino}phenyl)pyrimidin-2-yl]amino}phenyl)sulfonyl]butanamide
215. N-[2-(dimethylamino)ethyl]-2-phenyl-N-({4-[(4-{4-[(phenylacetyl)amino]phenyl}pyrimidin-2-yl)amino]phenyl}sulfonyl)acetamide
216. N-[4-(2-{[4-({[2-(dimethylamino)ethyl]amino}sulfonyl)phenyl]amino}pyrimidin-4-yl)phenyl]-3-methylbutanamide
217. N-[2-(dimethylamino)ethyl]-3-methyl-N-({4-[(4-{4-[(3-methylbutanoyl)amino]phenyl}pyrimidin-2-yl)amino]phenyl}sulfonyl)butanamide
218. N-[2-(dimethylamino)ethyl]-3-(2-thienyl)-N-[(4-{[4-(4-{[3-(2-thienyl)propanoyl]amino}phenyl)pyrimidin-2-yl]amino}phenyl)sulfonyl]propanamide
219. N-[4-(2-{[4-(aminosulfonyl)phenyl]amino}pyrimidin-4-yl)phenyl]-3-oxobutanamide
220. N-[2-(dimethylamino)ethyl]-4-[(4-{4-[(phenylsulfonyl)amino]phenyl}pyrimidin-2-yl)amino]benzenesulfonamide
221. N-[4-(2-{[3-(aminosulfonyl)phenyl]amino}pyrimidin-4-yl)phenyl]-2-(2-thienyl)acetamide
222. N-[4-(2-{[3-(aminosulfonyl)phenyl]amino}pyrimidin-4-yl)phenyl]-2-phenylacetamide
223. N-[4-(2-{[3-(aminosulfonyl)phenyl]amino}pyrimidin-4-yl)phenyl]-3,3-dimethylbutanamide
224. N-[4-(2-{[3-(aminosulfonyl)phenyl]amino}pyrimidin-4-yl)phenyl]-2-(3-thienyl)acetamide
225. N-[4-(2-{[3-(aminosulfonyl)phenyl]amino}pyrimidin-4-yl)phenyl]thiophene-2-carboxamide
226. 4-[4-(benzylamino)phenyl]-N-{4-[(4-methylpiperazin-1-yl)sulfonyl]phenyl}pyrimidin-2-amine
227. 4-{4-[(4-chloro-2-fluorobenzyl)amino]phenyl}-N-{4-[(4-methylpiperazin-1-yl)sulfonyl]phenyl}pyrimidin-2-amine
228. 4-{4-[(2,2-dimethylpropyl)amino]phenyl}-N-{4-[(4-methylpiperazin-1-yl)sulfonyl]phenyl}pyrimidin-2-amine
229. N-[5-(2-{[4-(aminosulfonyl)phenyl]amino}pyrimidin-4-yl)-2-thienyl]-3,3-dimethylbutanamide
230. 4-({4-[4-(benzylamino)phenyl]pyrimidin-2-yl}amino)-N-[3-(dimethylamino)propyl]benzenesulfonamide
231. N-(4-{[2-(dimethylamino)ethyl]sulfonyl}phenyl)-4-(4-nitrophenyl)pyrimidin-2-amine
232. N-[2-(dimethylamino)ethyl]-4-[(4-{4- [(2,2-dimethylpropyl)amino] phenyl}pyrimidin-2-yl)amino]benzenesulfonamide
233. N-(2-hydroxyethyl)-4-{[4-(4-nitrophenyl)pyrimidin-2-yl]amino}benzenesulfonamide
234. N-[2-(dimethylamino)ethyl]-4-[(4-{4-[(3,3-dimethylbutyl)amino] phenyl}pyrimidin-2-yl)amino]benzenesulfonamide
235. N-[3-(dimethylamino)propyl]-4-[(4-{4-[(2,2-dimethylpropyl)amino] phenyl}pyrimidin-2-yl)amino]benzenesulfonamide
236. N-[3-(dimethylamino)propyl]-4-[(4-{4-[(3,3-dimethylbutyl)amino] phenyl}pyrimidin-2-yl)amino]benzenesulfonamide
237. 2-amino-5-{[4-(3-fluoro-4-methoxyphenyl)pyrimidin-2-yl]amino}benzenesulfonamide
238. 4-{[4-(4-aminophenyl)pyrimidin-2-yl]amino}-N-(2-hydroxyethyl)benzenesulfonamide
239. N-(4-{2-[(4-{[(2-hydroxyethyl)amino]sulfonyl}phenyl) amino]pyrimidin-4-yl}phenyl)-3,3-dimethylbutanamide
240. N-(4-{2-[(4-{[(2-hydroxyethyl)amino]sulfonyl}phenyl)amino]pyrimidin-4-yl}phenyl)-2-(2-thienyl)acetamide
241. 2-(4-chlorophenyl)-N-(4-{2-[(4-{[(2-hydroxyethyl)amino]sulfonyl} phenyl)amino]pyrimidin-4-yl}phenyl)acetamide
242. 4-[(4-{4-[(4-phenylpyrimidin-2-yl)amino]phenyl}pyrimidin-2-yl)amino]benzenesulfonamide
243. 4-{[4-(4-{[4-(5-methyl-2-thienyl)pyrimidin-2-yl]amino}phenyl)pyrimidin-2-yl]amino}benzene sulfonamide
244. 4-{[4-(3-oxo-3H-spiro[1-benzofuran-2,1'-cyclopropan]-5-yl)pyrimidin-2-yl]amino}benzenesulfonamide
245. 4-(4-aminophenyl)-N-(4-{[2-(dimethylamino)ethyl]sulfonyl}phenyl)pyrimidin-2-amine
246. N-{4-[(4-methylpiperazin-1-yl)sulfonyl]phenyl}-4-{4-[(2-phenylethyl)amino]phenyl}pyrimidin-2-amine
247. 4-{4-[(2,2-dimethylbutyl)amino]phenyl}-N-{4-[(4-methylpiperazin-1-yl)sulfonyl]phenyl}pyrimidin-2-amine
248. N-(4-{2-[(4-{[2-(dimethylamino)ethyl]sulfonyl}phenyl) amino]pyrimidin-4-yl}phenyl)-2-phenylacetamide
249. N-(4-{2-[(4-{[2-(dimethylamino)ethyl]sulfonyl}phenyl) amino]pyrimidin-4-yl}phenyl)-2-(2-thienyl)acetamide
250. N-(4-{2-[(4-{[2-(dimethylamino)ethyl]sulfonyl}phenyl) amino]pyrimidin-4-yl}phenyl)-3,3-dimethylbutanamide
251. N-(4-{2-[(4-{[2-(dimethylamino)ethyl]sulfonyl}phenyl) amino]pyrimidin-4-yl}phenyl)-2-(4-methoxyphenyl)acetamide -continued 252. N-(4-{2-[(4-{[2-(dimethylamino)ethyl]sulfonyl}phenyl) amino]pyrimidin-4-yl}phenyl)-3-methylbutanamide
253. N-[4-(2-{[4-(aminosulfonyl)phenyl]amino}pyrimidin-4-yl)phenyl]-2-pyrrolidin-1-ylacetamide
254. N-(2,2-diethoxyethyl)-4-{[4-(2,3-dihydro-1-benzofuran-5-yl)pyrimidin-2-yl]amino}benzenesulfonamide
255. 4-{[4-(4-nitrophenyl)pyrimidin-2-yl]amino}-N-(2-pyrrolidin-1-ylethyl)benzenesulfonamide
256. 4-{[4-(2,3-dihydro-1-benzofuran-5-yl)pyrimidin-2-yl]amino}-N-(2-oxoethyl)benzenesulfonamide
257. 4-{[4-(4-{[(benzylamino)carbonothioyl]amino}phenyl)pyrimidin-2-yl]amino}-N-[2-(dimethylamino)ethyl]benzenesulfonamide
258. 4-(2-{[4-({[3-(dimethylamino)propyl]amino}sulfonyl)phenyl] amino}pyrimidin-4-yl)phenyl acetate
259. 4-{[4-(4-aminophenyl)pyrimidin-2-yl]amino}-N-(2-pyrrolidin-1-ylethyl)benzenesulfonamide
260. 4-{[4-(3-fluoro-4-methoxyphenyl)pyrimidin-2-yl]amino}-N-(2-pyrrolidin-1-ylethyl)benzenesulfonamide
261. 4-{[4-(4-bromophenyl)pyrimidin-2-yl]amino}benzenesulfonamide
262. 4-{[4-(4-bromophenyl)pyrimidin-2-yl]amino}-N-[3-(dimethylamino)propyl]benzenesulfonamide
263. 3,3-dimethyl-N-(4-{2-[(4-{[(2-pyrrolidin-1-ylethyl)amino]sulfonyl} phenyl)amino]pyrimidin-4-yl}phenyl)butanamide
264. 2-phenyl-N-(4-{2-[(4-{[(2-pyrrolidin-1-ylethyl)amino]sulfonyl} phenyl)amino]pyrimidin-4-yl}phenyl)acetamide
265. 4-(2-{[4-({acetyl[3-(dimethylamino)propyl]amino}sulfonyl) phenyl]amino}pyrimidin-4-yl)phenyl acetate
266. N-(4-{2-[(4-{[(2-pyrrolidin-1-ylethyl)amino]sulfonyl}phenyl) amino]pyrimidin-4-yl}phenyl)thiophene-2-carboxamide
267. 4-[(4-{4-[(aminocarbonothioyl)amino]phenyl}pyrimidin-2-yl)amino]-N- [3-(dimethylamino)propyl]benzenesulfonamide
268. N-[3-(dimethylamino)propyl]-4-[(4-{4-[(4-methyl-1,3-thiazol-2-yl)amino]phenyl}pyrimidin-2-yl)amino]benzenesulfonamide
269. 4-[(4-{4-[(1E)-3-(dimethylamino)prop-1-en-1-yl]phenyl}pyrimidin-2-yl)amino]benzenesulfonamide
270. N-[3-(dimethylamino)propyl]-4-[(4-{4-[(1E)-3-hydroxyprop-1-en-1-yl]phenyl}pyrimidin-2-yl)amino]benzenesulfonamide
271. 4-({4-[4-(2,5-dimethyl-1H-pyrrol-1-yl)phenyl]pyrimidin-2-yl}amino)benzenesulfonamide
272. 4-[(4-{4-[(1E)-3-hydroxyprop-1-en-1-yl]phenyl}pyrimidin-2-yl)amino]benzenesulfonamide
273. 4-{[4-(4-tert-butoxyphenyl)pyrimidin-2-yl]amino}-N-[2-(dimethylamino)ethyl]benzenesulfonamide
274. N-[2-(dimethylamino)ethyl]-4-{[4-(4-formylphenyl)pyrimidin-2-yl]amino}benzenesulfonamide
275. N-[2-(dimethylamino)ethyl]-4-{[4-(4-fluorophenyl)pyrimidin-2-yl]amino}benzene sulfonamide
276. N-(3,3-diethoxypropyl)-4-{[4-(2,3-dihydro-1-benzofuran-5-yl)pyrimidin-2-yl]amino}benzenesulfonamide
277. 4-{[4-(2,3-dihydro-1-benzofuran-5-yl)pyrimidin-2-yl]amino}-N-(3-oxopropyl)benzenesulfonamide
278. N-[2-(dimethylamino)ethyl]-4-((4-[4-(1,3-oxazol-5-yl)phenyl]pyrimidin-2-yl}amino)benzenesulfonamide
279. 4-(2-{[4-({[2-(dimethyiamino)ethyl]amino}sulfonyl)phenyl]amino}pyrimidin-4-yl)benzamide
280. N-[3-(dimethylamino)propyl]-4-[(4-{4-[(1E)-3-(1H-imidazol-1-yl) prop-1-en-1-yl]phenyl}pyrimidin-2-yl)amino]benzenesulfonamide
281. N-[3-(dimethylamino)propyl]-4-{[4-(4-{(1E)-3-[methyl(2-thienyl)amino]prop-1-en-1-yl}phenyl)pyrimidin-2-yl]amino}benzenesulfonamide
282. 4-{[4-(4-{(1E)-3-[(2-hydroxyethyl)amino]prop-1-en-1-yl}phenyl)pyrimidin-2-yl]amino}benzenesulfonamide
283. 4-{[4-(4-{(1E)-3-[(3-hydroxypropyl)amino]prop-1-en-1-yl}phenyl)pyrimidin-2-yl]amino}benzenesulfonamide
284. N-[3-(dimethylamino)propyl]-4-[(4-{4-[(1E)-3-morpholin-4-ylprop-1-en-1-yl]phenyl}pyrimidin-2-yl)amino]benzenesulfonamide
285. 4-[(4-{4-[(1E)-3-(dimethylamino)prop-1-en-1-yl]phenyl}pyrimidin-2-yl)amino]-N-[3-(dimethylamino)propyl]benzenesulfonamide
286. N-[3-(dimethylamino)propyl]-4-{[4-(4-formylphenyl)pyrimidin-2-yl]amino}benzene sulfonamide
287. 4-{[4-(2,3-dihydro-1-benzofuran-5-yl)pyrimidin-2-yl]amino}-N-[3-(dimethylamino)propyl]benzenesulfonamide
288. N-[3-(dimethylamino)propyl]-4-{[4-(4-fluorophenyl)pyrimidin-2-yl]amino}benzenesulfonamide
289. 4-{[4-(2,3-dihydro-1-benzofuran-5-yl)pyrimidin-2-yl]amino}-N-[3-(4-methylpiperazin-1-yl)propyl]benzenesulfonamide
290. 4-{[4-(4-piperidin-1-ylphenyl)pyrimidin-2-yl]amino}benzenesulfonamide
291. 4-({4-[4-(4-methylpiperazin-1-yl)phenyl]pyrimidin-2-yl}amino)benzenesulfonamide
292. N-[3-(dimethylamino)propyl]-4-({4-[4-(hydroxymethyl)phenyl]pyrimidin-2-yl}amino)benzenesulfonamide -continued 293. 4-{[4-(1-benzothien-2-yl)pyrimidin-2-yl]amino}-N-[2-(dimethylamino)ethyl]benzenesulfonamide
294. 4-[(9-methoxy-5,6-dihydrobenzo[h]quinazolin-2-yl)amino]benzenesulfonamide
295. 4-[(8,9-dimethoxy-5,6-dihydrobenzo[h]quinazolin-2-yl)amino]benzenesulfonamide
296. 4-(5,6-dihydrobenzo[h]quinazolin-2-ylamino)benzenesulfonamide
297. 4-{[4-(5,6-dihydro-4H-pyrrolo[1,2-b]pyrazol-2-yl)pyrimidin-2-yl]amino}benzenesulfonamide
298. N-[3-(dimethylamino)propyl-4-[(4-{4-[(1E)-3-methoxyprop-1-en-1-yl]phenyl}pyrimidin-2-yl)amino]benzenesulfonamide
299. 3-[2-(4-{[4-(3-fluoro-4-methoxyphenyl)pyrimidin-2-yl]amino}phenyl)-1H-imidazol-1-yl]propan-1-ol The presence of certain substituents in the compounds of formula I may enable salts of the compounds to be formed. Suitable salts include pharmaceutically acceptable salts, for example acid addition salts derived from inorganic or organic acids, and salts derived from inorganic and organic bases. The phrase "pharmaceutically acceptable salt," as used herein, is a salt formed from an acid and a basic nitrogen group of a pharmaceutically active agent. Illustrative salts include, but are not limited to, sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts. The phrase "pharmaceutically acceptable salt" also refers to a salt prepared from a pharmaceutically active agent having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In another embodiment, the present invention provides processes for making a compound of formula I as defined above. The present invention also encompasses intermediates of these processes. Throughout the description of the processes, the numbered R groups are defined above with respect to formula I, and generic (not numbered) R groups represent independent substituents as described above. The compounds shown in the Figures are numbered by figure number and, where appropriate, a parenthetical note designating the corresponding general structure is also included. The term "reacting" includes, but is not limited to, adding, stirring, heating, heating to reflux, dissolving, titurating, and any combination thereof. One skilled in the art would appreciate the meaning of reacting given the reaction components and given the examples provided herein. The processes preferably include a step of isolating the compound of formula I.

In one embodiment, the present invention provides methods for preparing a compound of formula I by reacting an enaminone and a guanidine (Scheme 1). In one embodiment, an enaminone of formula G-1 is reacted with a guanidine of formula G-2 in the presence of 1-methyl-2-pyrrolidinone (NMP).

Scheme 1:

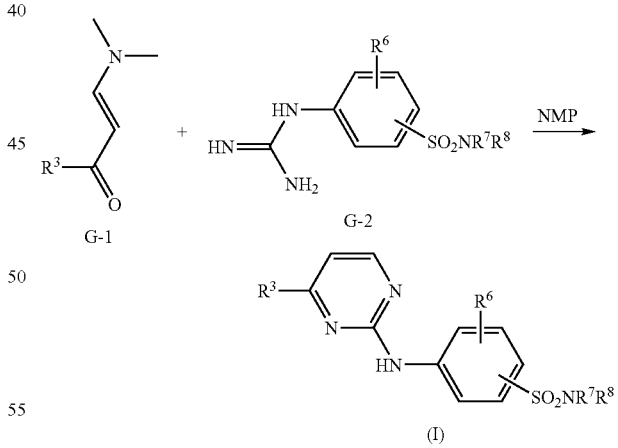

In the exemplary Scheme 1 showed above, the process produces a compound of formula I wherein $R^2$ is $NR^7R^8$, and $R^1$, $R^4$, $R^5$ are each hydrogen.

Preferably, the reaction is conducted in the presence of a base, such as potassium carbonate or potassium hydroxide.

The enaminone G-1 can be prepared by any method known in the art, such as the reaction of an acetyl derivative with an acetal, preferably N,N-dimethylformamide dimethyl acetal, or tert-butoxybis(dimethylamino)methane. See FIG. 1.

The guanidine G-2 can be prepared by reacting an amine of formula G-3 with cyanamide or 1-H-pyrazole-1-carboximidine. See also FIG. 1.

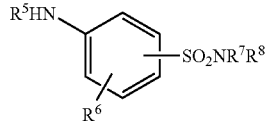

G-3

Alternatively, the guanidine G-2 can be prepared by reacting a halogenated sulfonamide of formula G-4 with guanidine. See FIG. 2.

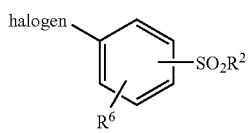

G-4

In another embodiment of Scheme 1, the $SO_2R^2$ group is added after the formation of the pyrimidine. This method includes the steps of: reacting an enaminone G-1 with a guanidine derivative of formula 3-1 and NMP to form a pyrimidine; reacting the pyrimidine with chlorosulfonic acid to form a sulfonyl chloride of formula 3-3; and reacting the sulfonyl chloride 3-3 with an amine having the formula $HNR^7R^8$ to form a compound of formula I. See FIG. 3.

In another embodiment, the present invention provides methods for preparing a compound of formula I by halogen displacement (Scheme 2). The Scheme 2 reactions can be conducted in a solvent, preferably dioxane. In a preferred embodiment of Scheme 2 reactions, $R^3$ is an optionally substituted phenyl or optionally substituted thienyl group.

In one embodiment, an amine G-3 is reacted with a halogenated pyrimidine of formula G-5. Preferably, the halogen of the halogenated pyrimidine is chlorine. Preferably, the reaction is conducted in the presence of p-toluenesulfonic acid.

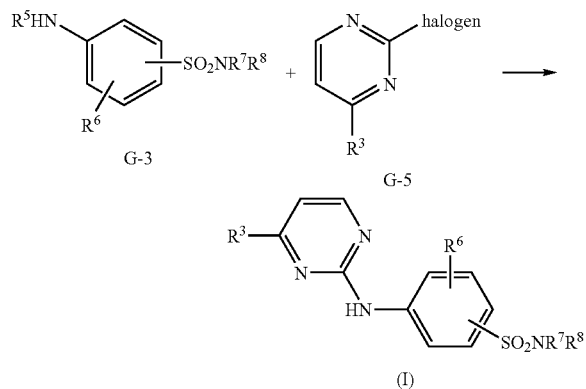

In another embodiment of Scheme 2, a halogenated sulfonamide of formula G-4 is reacted with a pyrimidine of formula G-6. Preferably, the halogen of the halogenated sulfonamide is bromine. Preferably, the reaction includes a step of adding sodium tert-butoxide (NaOtBu). Also, the reaction is preferably conducted in the presence of tris(dibenzylideneacetone)dipalladium(0) ($Pd_2dba_3$) and 2,2'-bis(diphenylphosphino)-1,1'-binaphthyl (BINAP).

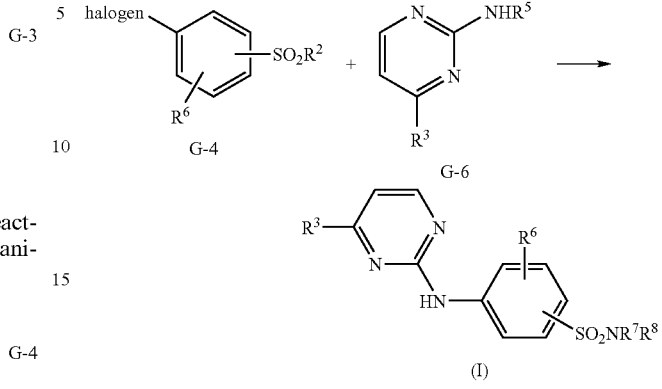

In the exemplary Scheme 2's showed above, the process produces a compound of formula I wherein $R^2$ is $NR^7R^8$, and $R^1$, $R^4$, $R^5$ are each hydrogen.

Starting materials used are either commercially available or readily prepared by one of ordinary skill in the art. Solvents, temperatures, pressures, and other reaction conditions may be modified be one of ordinary skill in the art. Where appropriate, the methods described herein may be carried out with starting materials, intermediates, and/or reagents bound to a solid support (e.g., see Thompson, L. A., Ellman, J. A., Chemical Reviews, 96, 555-600 (1996)).

In another embodiment, the present invention also provides pharmaceutical compositions comprising a compound of the present invention and a pharmaceutically acceptable carrier. Pharmaceutical compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

In another embodiment, the present invention provides a method of inhibiting kinase action, especially IKK, by providing one or more compounds or pharmaceutical compositions of the present invention. Providing includes, but is not limited to, administration by pharmaceutical acceptable methods and routes of administration known by one of skill in the art. Providing also means exposing to or contacting with. Compounds of the present invention are useful to inhibit kinase activity, particularly IKK. Inhibiting includes total inhibition as well as decreasing or reducing. Without being bound by theory, by blocking the association of IKKβ and IκBα, compounds of the present invention are believed to inhibit the ability of the IKK complex to phosphorylate IκB. As such, NF-κB is not released and does not enter the nucleus to activate transcription.

Various assays demonstrate that compounds of the present invention are useful as IKK inhibitors. For example, a binding assay demonstrates that compounds of the present invention affect the association of IKKβ and IκBα. The binding assay is performed by contacting compounds of the present invention with IKKβ enzyme and IκBα substrate and then detecting whether the compound inhibits association of IKKα and IκBα. Compounds of the present invention that inhibit the association of IKKβ and IκBα may inhibit the ability of IKK to phosphorylate IκB and as such may inhibit the release of NF-κB and the transcription of NF-κB controlled genes.

The present invention also provides a method of inhibiting kinase activity, especially IKK, in a mammal, especially a human, by administering a kinase-inhibiting amount, especially an IKK-inhibiting amount, of a compound or pharmaceutical composition of the present invention. Administering includes all pharmaceutical acceptable methods and routes of administration known by one of skill in the art.

Because IKK plays a key role in inflammation, cell growth, and tumorigenesis, compounds that inhibit IKK may be useful as anti-inflammation and anti-cancer agents. Accordingly, one embodiment provides a method of treating a kinase-dependent condition, such as an IKK dependent condition, comprising administering to a subject a kinase-inhibiting amount, such as an IKK-inhibiting amount, of a compound or pharmaceutical composition of the present invention. Kinase-dependent conditions, including IKK dependent conditions, include, but are not limited to autoimmune diseases such as rheumatoid arthritis, multiple sclerosis, and systemic lupus erythematosus, transplant rejection, graft versus host disease, hyperproliferative disorders such as tumors, psoriasis, pannus formation in rheumatoid arthritis, restenosis following angioplasty and atherosclerosis, osteoporosis and in diseases in which cells receive pro-inflammatory signals such as asthma, inflammatory bowel disease, and pancreatitis.

The pharmaceutical compositions comprising compounds of the present invention may inhibit kinase activity, particularly IKK. Kinase inhibition would in turn inhibit the downstream expression of genes responsible for kinase-dependent conditions such as inflammation and cancer. For example, inhibiting IKK inhibits the activation of NF-κB, which in turn reduces expression of NF-κB dependent genes. Because NF-κB dependent genes have been correlated with inflammation and cancer, pharmaceutical compositions comprising compounds that inhibit IKK may be useful to treat inflammation and cancer.

The present invention also provides methods of treating diseases associated with NF-κB activation by administering a pharmaceutical composition of the present invention. Treating includes, but is not limited to, complete treatment, where no symptoms are seen, as well as reducing symptoms and ameliorating symptoms. The phrase "treating," "treatment of," and the like includes the amelioration or cessation of a specified condition. Diseases associated with NF-κB activation include, but are not limited to inflammatory disorders; particularly rheumatoid arthritis, inflammatory bowel disease, and asthma; dermatosis, including psoriasis and atopic dermatitis; autoimmune diseases; tissue and organ rejection; Alzheimer's disease; stroke; epilepsy; Parkinson's disease, atherosclerosis; restenosis; cancer, including Hodgkins disease; and certain viral infections, including AIDS; osteoarthritis; osteoporosis; and Ataxia Telangiestasia.

In one embodiment, the present invention provides methods of treating cancer by administering a pharmaceutical composition of the present invention. Cancer includes an abnormal growth of cells, which tend to proliferate in an uncontrolled way and, in some cases, to metastasize (spread). Treating cancer encompasses, but is not limited to inhibiting or reducing tumor cell proliferation, tumor cell growth, and inhibiting tumorigenesis. Cancer includes, but is not limited to cancer of the colon, rectum, prostate, liver, lung, bronchus, pancreas, brain, head, neck, stomach, skin, kidney, cervix, blood, larynx, esophagus, testes, urinary bladder, ovary, or uterus.

In another embodiment, the present invention provides methods of treating an inflammatory or autoimmune condition by administering a pharmaceutical composition of the present invention. Treating inflammation encompasses, but is not limited to reducing inflammation and treating an inflammatory condition. Inflammatory and autoimmune conditions include, but are not limited to rheumatoid arthritis, rheumatoid spondylitis, osteoarthritis, gout, asthma, bronchitis, allergic rhinitis, chronic obstructive pulmonary disease, cystic fibrosis, inflammatory bowel disease, irritable bowel syndrome, mucous colitis, ulcerative colitis, diabrotic colitis, Crohn's disease, gastritis, esophagitis, hepatitis, pancreatitis, nephritis, psoriasis, eczema, dermatitis, hives, multiple sclerosis, Lou Gehrig's disease, sepsis, conjunctivitis, acute respiratory distress syndrome, purpura, nasal polyp, lupus erythematosus, conjunctivitis, vernal catarrh, chronic arthrorheumatism, systemic inflammatory response syndrome (SIRS), sepsis, polymyositis, dermatomyositis (DM), Polyaritis nodoa (PN), mixed connective tissue disease (MCTD), and Sjoegren's syndrome.

In another embodiment, the present invention provides methods of treating a cardiovascular, metabolic, or ischemic condition by administering a pharmaceutical composition of the present invention. Cardiovascular, metabolic, and ischemic conditions include, but are not limited to atherosclerosis, restenosis following angioplasty, left ventricular hypertrophy, insulin resistance, Type I diabetes, Type II diabetes, hyperglycemia, hyperinsulinemia, dyslipidemia, obesity, polycystic ovarian disease, hypertension, syndrome X, osteoporosis, erectile dysfunction, cachexia, myocardial infraction, ischemic diseases of heart kidney, liver, and brain, organ transplant rejection, graft versus host disease, endotoxin shock, and multiple organ failure.

In yet another embodiment, the present invention provides methods of treating an infectious disease, particularly a viral infection, by administering a pharmaceutical composition of the present invention. Viral infections include, but are not limited to those caused by human immunodeficiency virus (HIV), hepatitis B virus, hepatitis C virus, human papillomavirus, human T-cell leukemia virus, and Epstein-Barr virus.

In another embodiment, the present invention provides methods of treating a pre- or post-menopausal condition by administering a pharmaceutical composition of the present invention. In particular, a pharmaceutical composition of the present invention can be used to treat osteoporosis. Treating osteoporosis includes preventing osteoporosis as well as combating the existing condition.

The present invention also provides methods of inhibition and treatment further comprising administering an additional inhibitor of a protein kinase of the NF-κB pathway. Inhibitors of a protein kinase of the NF-κB pathway include, but are not limited to IKK inhibitors and GSK-3 inhibitors. IKK inhibitors include, but are not limited to heterocyclic carboxamides, substituted benzimidazoles, substituted indoles, β-carbolines such as PS-1145, SPC0023579, SPC839/AS602868 (AS2868), NVPIKK004, and NVPIKK005. GSK-3 inhibitors include, but are not limited to maleimides such as SB410111, SB495052, SB517955, SB216763, SB415286, diamino-1,2,4-triazole carboxylic acid derivatives and 2,5-dihydro-1H-pyrrole-2,5-dione derivatives, diaminothiazoles, bicyclic compounds, pyrazine derivatives, pyrimidine- or pyridine derivatives, and purine derivatives such as CT 98014, CT98023, CT99021, 2-amino-3-(alkyl)-pyrimidone derivatives, 1H-imidazol-4-amine derivatives, and 3-indolyl-4-phenyl-1H-pyrrole-2,5-dione derivatives. Haefner, B. (2002) "NF-κB: arresting a major culprit in cancer," *Drug Discovery Today*, 7, 658.

The pharmaceutical compositions of the present invention may comprise the compound of the present invention alone or in combination with other kinase-inhibiting compounds or chemotherapeutic agents. Chemotherapeutic agents include, but are not limited to exemestane, formestane, anastrozole, letrozole, fadrozole, taxane and derivatives such as paclitaxel or docetaxel, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, tamoxifen, raloxifen, Sugen SU-5416, Sugen SU-6668, and Herceptin.

The pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the compound of formula I and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable administration in any given case will depend on the nature and severity of the condition being treated. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, such as a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may include any of the aforementioned blends and granulates that were described with reference to tableting, however, they are not subjected to a final tableting step.

Methods of administration of a pharmaceutical composition encompassed by the invention are not specifically restricted, and can be administered in various preparations depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations are administered singly intramuscularly, intracutaneously, subcutaneously or intraperitoneally. Suppositories may be administered into the rectum.

The amount of the compound of formula I contained in a pharmaceutical composition according to the present invention is not specifically restricted, however, the dose should be sufficient to treat, ameliorate, or reduce the targeted symptoms. The dosage of a pharmaceutical composition according to the present invention will depend on the method of use, the age, sex, and condition of the patient.

Having described the invention, the invention is further illustrated by the following non-limiting examples.

EXAMPLES

Scheme 1: The Guanidine and Enaminone Reaction

Example 1

Preparation of 4-[4-(5-Chloro-thiophen-2-yl)-pyrimidin-2-ylamino]-benzenesulfonamide (Exemplary Compound 4) See FIG. 1

Step 1: 2-Acetyl-5-chlorothiophene (0.8 g, 5 mmol) is dissolved in dimethylformamide dimethylacetal (6 mL), and the solution is heated to reflux for 3 hrs. The solvent is evaporated to obtain the crude 1-(5-chloro-thiophen-2-yl)-3-dimethylamino-propenone.

Step 2: A mixture of sulfanilamide (0.86 g, 5 mmol) and 1-H-pyrazole-1-carboxamidine HCl (0.73 g, 5 mmol) in 3 mL nitrobenzene is heated to reflux for 2 hrs. The solution is decanted from the solid that is formed. N-butanol (8 mL), aqueous NaOH solution (0.73 mL 10N), and the crude 1-(5-chloro-thiophen-2-yl)-3-dimethylamino-propenone is added to the solid. The reaction is heated to reflux overnight. The reaction is allowed to cool, and the product is collected by filtration and rinsed with diethyl ether to obtain 8.3 mg of the title compound as a tan solid. LC/MS data (Condition A; molecular ion and retention time): m/z 367 (M+H); 2.85 min.

Exemplary compounds 5-34 can also be synthesized according to this method.

HPLC Conditions (Condition A): Hewlett Packard 1100 MSD with ChemStation Software; Xterra $C_{18}$ column, 30 mm×2.1 mm, 5μ particle size, at 50° C.; Solvent A: Water (0.02% formic acid buffer); Solvent B: Acetonitrile (0.02% formic acid buffer); Gradient: Time 0: 5% B; 0.3 min: 5% B; 3.0 min: 90% B; Hold 90% B 2 min; Flow rate: 1.0 mL/min; Detection: 254 nm DAD; API-ES Scanning Mode Negative 150-700; Fragmentor 70 mV.

Example 1b

Preparation of 4-[4-(5-Pyridin-2-ylethynyl-thiophen-2-yl)-pyrimidin-2-ylamino]-benzenesulfonamide (Exemplary Compound 35) See FIG. 1

Step 1: 4-[4-(5-Bromo-thiophen-2-yl)-pyrimidin-2-ylamino]-benzenesulfonamide is prepared by the procedure described in Example 1a. $^1$H NMR ($d_6$-DMSO, 300 MHz) δ 7.19 (s, 1H), 7.39 (d, J=3.9 Hz, 1H), 7.45 (d, J=5.4 Hz, 1H), 7.75 (s, 1H), 7.86 (s, 1H), 7.90-7.96 (m, 3H), 8.58 (d, J=5.4 Hz, 1H), 10.12 (s, 1H); LC/MS data (Condition A; molecular ion and retention time): m/z 411 and 413 (M+H); 2.59 min.

Step 2: A 10 mL glass microwave reaction vessel with stir bar contained palladium acetate (5 mg, 22 μmol), tri-o-tolylphosphine (13 mg, 44 μmol), and 4-[4-(5-bromo-thiophen-2-yl)-pyrimidin-2-ylamino]-benzenesulfonamide (80 mg, 200 μmol). Anhydrous dimethylformamide (DMF) (3.5 mL), 2-ethynylpyridine (46 mg, 450 μmol), and triethylamine (50 μL) is added to the reaction vessel. The reaction vessel is sealed and heated to 180° C. for 660 seconds in a microwave reactor (Emrys Microwave Reactor, personal Chemistry AB, Uppsala, Sweden). The reaction is filtered through celite, concentrated, redissolved in dimethylsulfoxide (DMSO), and purified by reverse phase (RP) HPLC to obtain 10 mg of the title compound. LC/MS data (Condition A; molecular ion and retention time): m/z 434 (M+H); 2.52 min.

Exemplary compounds 36-38 can also be synthesized according to this method.

Example 2

Figure 2:
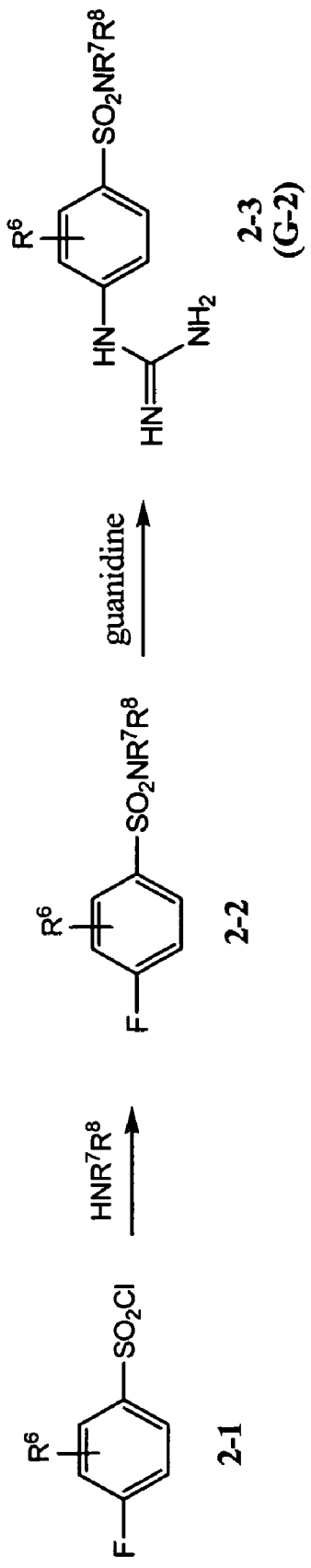

Preparation of N-[4-(Morpholin-4-ylsulfonyl)phenyl]-4-[4-(trifluoromethyl)phenyl]pyrimidin-2-amine (Exemplary Compound 39) See FIG. 2

Step 1: Preparation of 4-[(4-fluorophenyl)sulfonyl]morpholine

To a solution of 4-fluorobenzenesulfonyl chloride (3.97 g, 20 mmol) in methylene chloride (40 ml), at 0° C., under nitrogen, with stirring, is added morpholine (4.4 mL, 50 mmol). The mixture is stirred at 0° C. for 15 min. and then warmed to room temperature for 18 hrs. The resulting suspension is filtered, and the filtrate is stirred with 10% potassium carbonate for 2 hrs. The methylene chloride is evaporated, and the aqueous suspension is filtered, and the precipitate is washed with water, and then dried in vacuo to give 5.0 g of a white solid; mp 106-107° C.; MS (APCI) m/z 246.1 (M+H).

Step 2A: Preparation of N-[4-(morpholin-4-ylsulfonyl)phenyl]guanidine

A mixture of 4-[(4-fluorophenyl)sulfonyl]morpholine (0.25 g, 1 mmol), cesium carbonate (1.30 g, 4 mmol), and guanidine carbonate (1.08 g, 6 mmol) in 2 ml of 1-methyl-2-pyrrolidinone (NMP) is stirred at 85 to 90° C. for 24 hrs. It is then cooled to room temperature and diluted with ether. The resulting suspension is filtered, and the precipitate extracted with tetrahydrofuran (THF) to yield, after evaporation of solvent, 0.12 g of a yellow solid; mp 102-105° C.; MS (ESI) m/z 285.1 (M+H); HRMS: calcd for $C_{11}H_{16}N_4O_3S$, 284.0943; found (ESI_FT), 285.1011 (M+H).

Step 2B: Preparation of (2E)-3-(dimethylamino)-1-[4-(trifluoromethyl)phenyl]prop-2-en-1-one A solution of 4'-(trifluoromethyl)acetophenone (9.60 g, 50 mmol) in 25 ml of N,N-dimethylformamide dimethyl acetal (DMF-DMA) is stirred at 105 to 110° C. for 20 hrs. It is then cooled to room temperature, and diluted with hexanes. The resulting suspension is filtered, and the precipitate washed with hexanes to give 10.93 g of a yellow solid; mp 96.5-98° C.; MS (ESI) m/z 244.1 (M+H).

Step 3: Preparation of N-[4-(morpholin-4-ylsulfonyl)phenyl]-4-[4-(trifluoromethyl)phenyl]-pyrimidin-2-amine A mixture of N-[4-(morpholin-4-ylsulfonyl)phenyl]guanidine (85 mg, 0.3 mmol), (2E)-3-(dimethylamino)-1-[4-(trifluoromethyl)phenyl]prop-2-en-1-one (43 mg, 0.18 mmol), and potassium carbonate (83 mg, 0.6 mmol) in 1 ml of 1,3-dimethyl-3,4,5,6-tetrahydro-2(1H)-pyrimidinone (DMPU) is stirred at 105 to 110° C. for 18 hrs. It is then cooled to room temperature, and diluted with water (15 ml). The resulting suspension is filtered, and the precipitate is washed with dilute citric acid and water, and then dissolved in ethyl acetate. The organic solution is passed through a pad of silica gel, and the filtrate is evaporated. The residue is triturated with a mixture of methylene chloride and hexanes to give 63 mg of a yellow solid; mp 240-241° C.; MS (ESI) m/z 465.2 (M+H); HRMS: calcd for $C_{21}H_{19}F_3N_4O_3S$, 464.1130; found (ESI_FT), 465.11835.

Exemplary compounds 40-67 can also be synthesized according to this method.

Example 3

Figure 3:
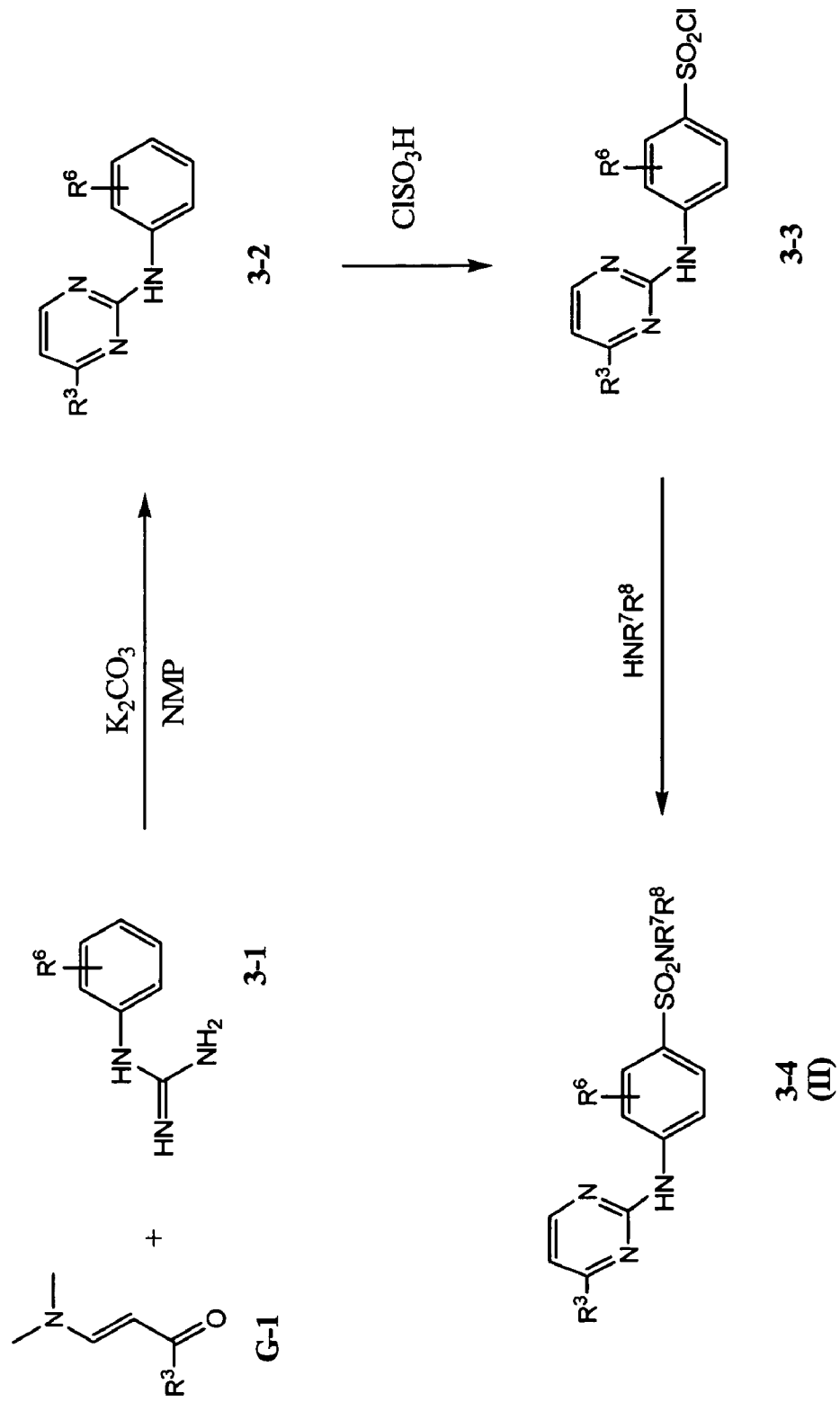

Preparation of N-(3-hydroxypropyl)4-({4-[4-(trifluoromethyl)phenyl]pyrimidin-2-yl}amino)-benzenesulfonamide (Exemplary Compound 68) See FIG. 3

Step 1: Preparation of N-phenyl-4-[4-(trifluoromethyl)phenyl]pyrimidin-2-amine A solution of (2E)-3-(dimethylamino)-1-[4-(trifluoromethyl)phenyl]prop-2-en-1-one (0.49 g, 2 mmol) and phenylguanidine carbonate salt (0.30 g, 2.2 mmol) in NMP (4 ml), is stirred at 120° C. for 2 days. It is then cooled to room temperature and diluted with water (40 ml). The resulting suspension is filtered, and the precipitate is washed with 50% ammonium chloride solution, water, and hexanes, and then dried in vacuo to give 0.56 g of an off-white solid; mp 162-163° C.; HRMS: calcd for $C_{17}H_{12}F_3N_3$, 315.0983; found (ESI_FTMS, [M+H]$^{1+}$), 316.1048.

Step 2: Preparation of 4-({4-[4-(trifluoromethyl)phenyl]pyrimidin-2-yl}amino)benzenesulfonyl chloride A solution of N-phenyl-4-[4-(trifluoromethyl)phenyl]pyrimidin-2-amine (0.16 g, 0.5 mmol) in 1.5 ml of chlorosulfonic acid is stirred at 65 to 70° C. for 1 hr. It is then cooled to room temperature, and added slowly to a stirred mixture of ice and water. The resulting suspension is filtered, and the precipitate is washed with water and then dried in vacuo to give 0.24 g of a yellow solid; mp 186-188° C.; HRMS: calcd for $C_{17}H_{11}ClF_3N_3O_2S$, 413.0213; found (ESI-FTMS, [M+H]$^{1+}$), 414.02984.

Step 3: Preparation of N-(3-hydroxypropyl)-4-({4-[4-(trifluoromethyl)phenyl]pyrimidin-2-yl}amino)benzenesulfonamide To a solution of 4-({4-[4-(trifluoromethyl)phenyl]pyrimidin-2-yl}amino)benzenesulfonyl chloride (0.10 g, 0.25 mmol) in 2 ml of ethyl acetate is added 3-amino-1-propanol (0.19 g, 2.5 mmol) with stirring, at 0° C. The mixture is stirred at room temperature for 1 hr and then quenched with water (10 ml). The ethyl acetate is evaporated, the resulting suspension is filtered, and the precipitate is washed with water, and hexanes, and then dried in vacuo to give 0.10 g of a white solid; mp 204-205° C.; HRMS: calcd for $C_{20}H_{19}F_3N_4O_3S$, 452.1130; found (ESI-FTMS, [M+H]$^{1+}$), 453.12161.

Exemplary compounds 67 can also be synthesized according to this method.

Example 4

Figure 4:
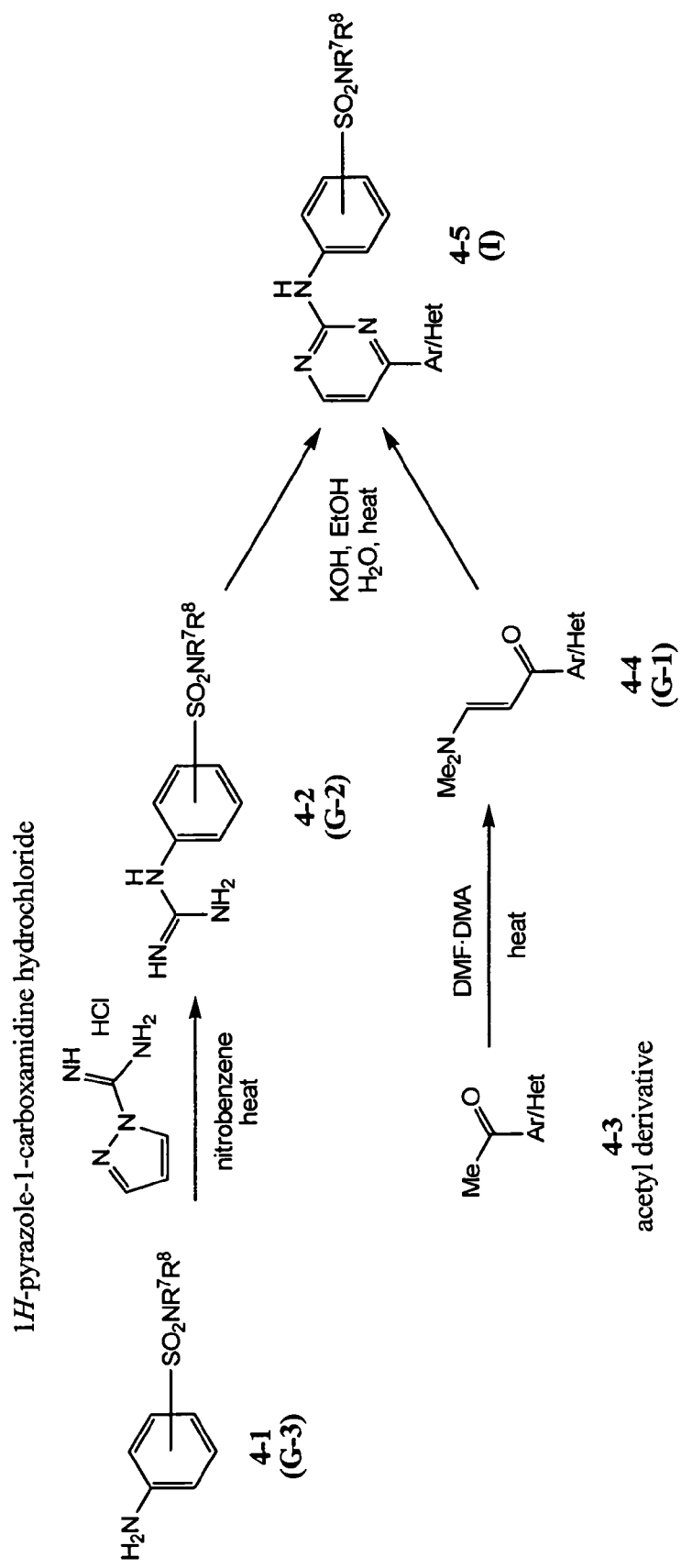
Figure 5:
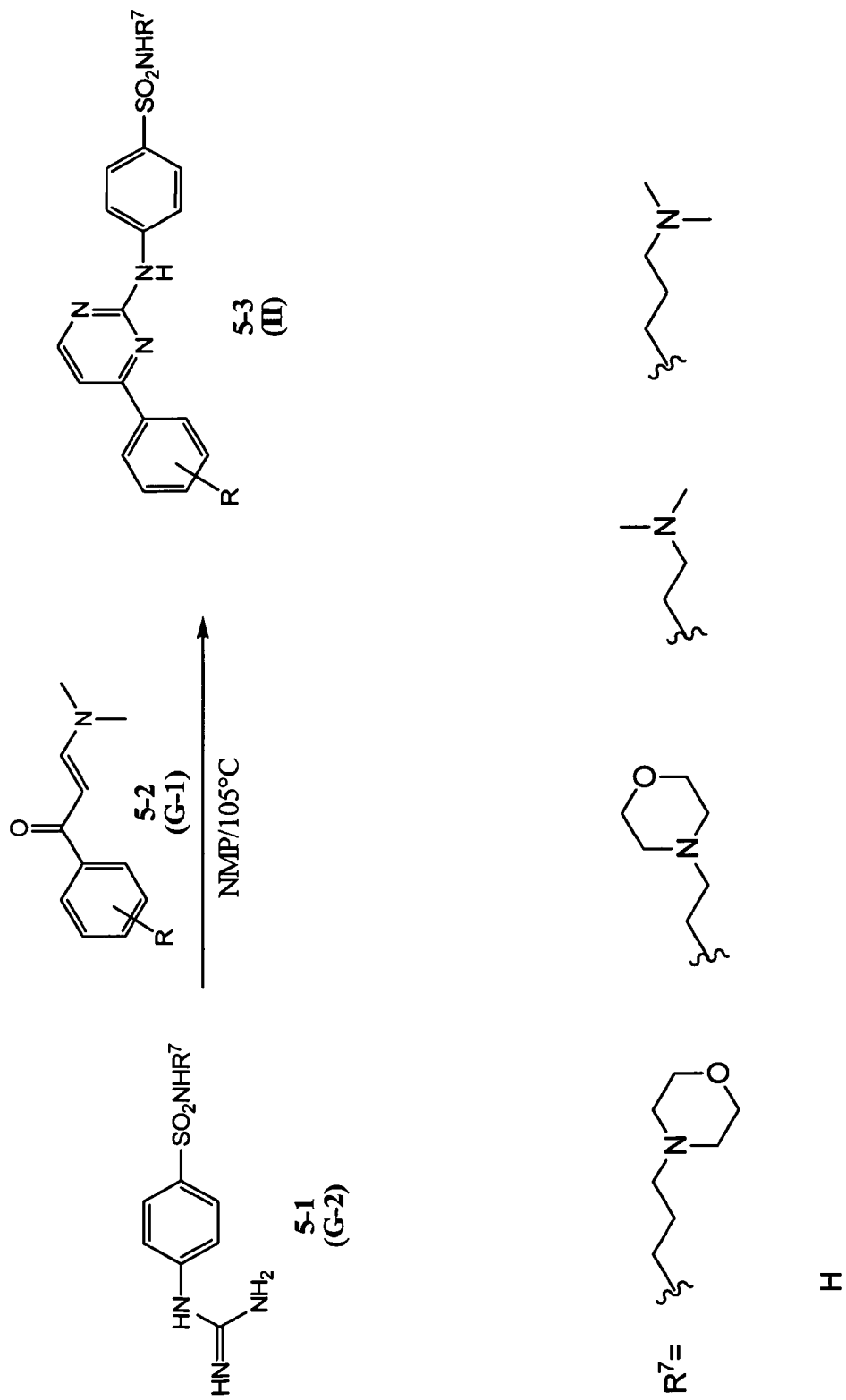

General Experimental for the Preparation of 2-anilino-4-aryl/heteroarylpyrimidine Primary Sulfonamides. See FIG. 4

Aniline target molecules of structure (I) may also be prepared using the procedure first outlined by Bredereck (Bredereck, H. et al. Ber., Dtsch. Chem. Ges. 1964, 97, 3397). Amines (G-3) can be converted to the corresponding aryl guanidines (G-2) using pyrazole-1-carboxamidine according to the procedure of Bernatowicz (Bernatowicz, M. S. et al. J. Org. Chem. 1992, 57, 2497). The guanidines can be combined with 3-dimethylamino-1-aryl/heteroaryl-propenones (G-1), prepared by heating methyl ketones (4-3) with DMF DMA, in the presence of a base such as KOH, NaOH, or Et$_3$N, or an acid such as HOAC in hot EtOH or MeOH to give the desired 2-aminopyrimidines (1).

Step 1: Preparation of 3-dimethylamino-1-aryl/heteroaryl-propenone (G-1)

A 0.1 M solution of a methyl ketone is heated at 130° C. for 12 h. After cooling to 23° C., all volatiles are evaporated. The remaining material is dissolved in a minimum of CH$_2$Cl$_2$ and passed through as short SPE SiO$_2$ gel cartridge eluting with additional CH$_2$Cl$_2$. The eluant is concentrated to a minimum volume, and an equal amount of hexanes is added. Cooling to 5° C. produces crystals of the title compound as a yellow or orange solid.

Step 2: Preparation of 2-anilino-4-aryl/heteroarylpyrimidine primary sulfonamides (I)

Aniline (1 equiv.) is combined with 1.5 equiv. of 1H-pyrazole-1-carboxamidine hydrochloride as a 0.1 M nitrobenzene solution and heated to 200° C. for 6 h. After cooling to 23° C., 1 equiv. of 3-dimethylamino-1-aryl/heteroaryl-propenone is added followed by 1.25 equiv. of KOH, EtOH (equal volume to that of nitrobenzene) and $H_2O$, (1/10th the volume of EtOH). This mixture is heated at 120° C. for 12 h, cooled to 23° C., and evaporated in a Speed-Vac. This crude material is dissolved in 0.5 ml DMSO: 1.5 ml MeCN, filtered through a 0.45 μm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions are analyzed by LC/MS. To isolate the title compound, the pure fractions are combined and the solvent is evaporated in a Speed-Vac.

Exemplary compounds 1, 4, 9, 10, 12, 13, 15, 16, 18-29, 31, 32, 34, 35, 37, 38, 69, and 70 can be synthesized according to this method.

HPLC Conditions: Instrument—Agilent 1100; Column: Keystone Aquasil C18 (as above); Mobile Phase A: 10 mM $NH_4OAC$ in 95% water/5% CAN; Mobile Phase B: 10 mM $NH_4OAC$ in 5% water/95% CAN; Flow Rate: 0.800 ml/min; Column Temperature: 40° C.; Injection Volume: 5 ul; UV: monitor 215, 230, 254, 280, and 300 nm; Purity is reported at 254 nm unless otherwise noted.

| Gradient Table: | |
|---|---|
| Time (min) | % B |
| 0.0 | 0 |
| 2.5 | 100 |
| 4.0 | 100 |
| 4.1 | 0 |
| 5.5 | 0 |

MS Conditions: Instrument: Agilent MSD; Ionization Mode: API-ES; Gas Temperature: 350 C; Drying Gas: 11.0 L/min.; Nebulizer Pressure: 55 psig; Polarity: 50% positive, 50% negative; VCap: 3000V (positive), 2500V (negative); Fragmentor: 80 (positive), 120 (negative); Mass Range: 100-1000 m/z; Threshold: 150; Step size: 0.15; Gain: 1; Peak width: 0.15 min.

Example 5

The enamino is added to a solution of the substituted guanidine in NMP, and the mixture is heated at 105° C. for 48 hours. The reaction is cooled to room temperature. Water is added, and the aqueous layer is extracted with EtOAc. The solvent is removed by evaporation, and the residue is purified by pre-plate with DCM/EtOAc/MeOH (8:8:1).

Exemplary compounds 45-66 and 89-92 can be synthesized according to this method.

Exemplary compounds 104, 107, 125, 129, 219, 294, 295, 296, 297 can also be synthesized according to this method.

Exemplary compounds 243-244 can also be synthesized according to this method.

Example 6

Figure 6A:
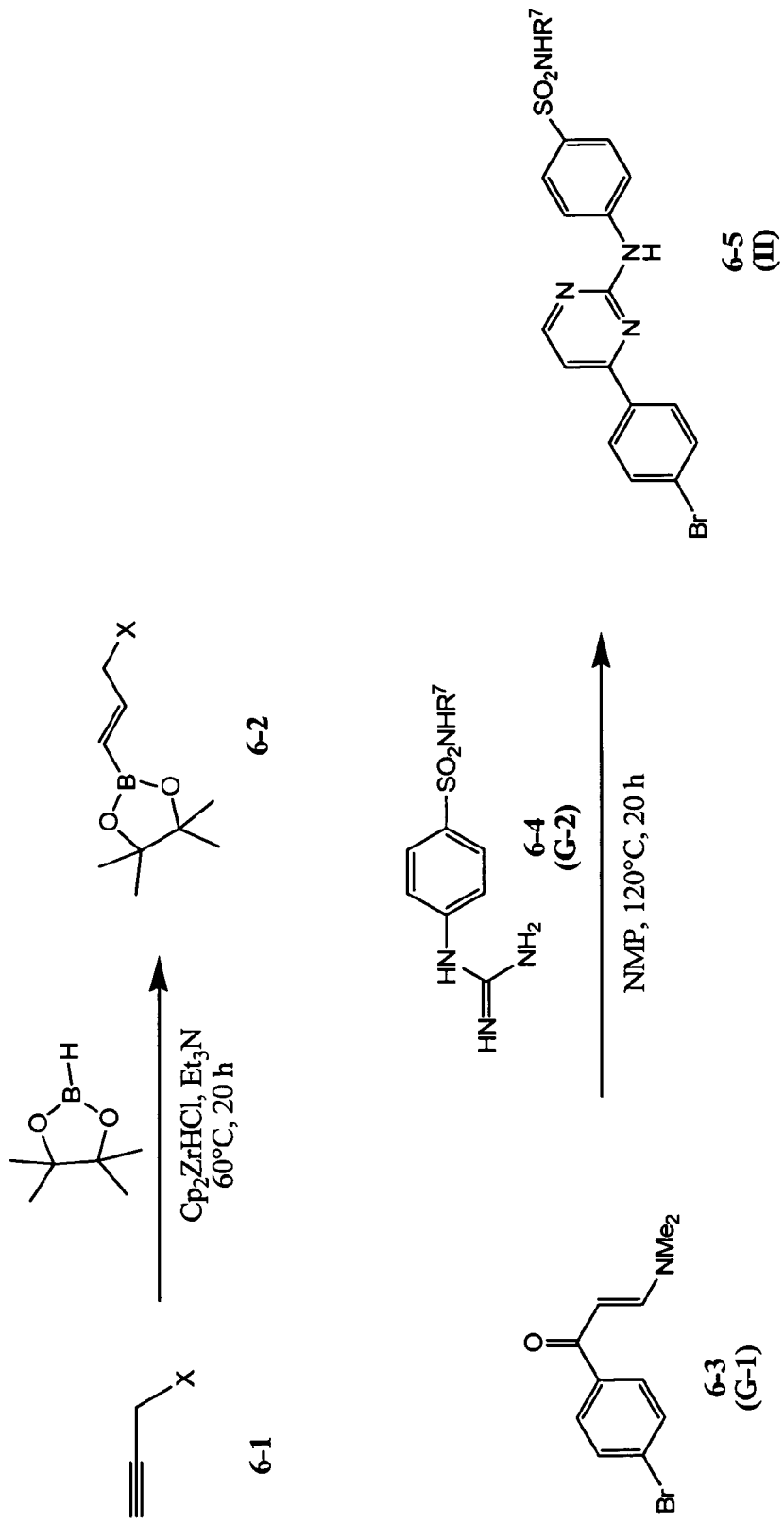
Figure 6B:
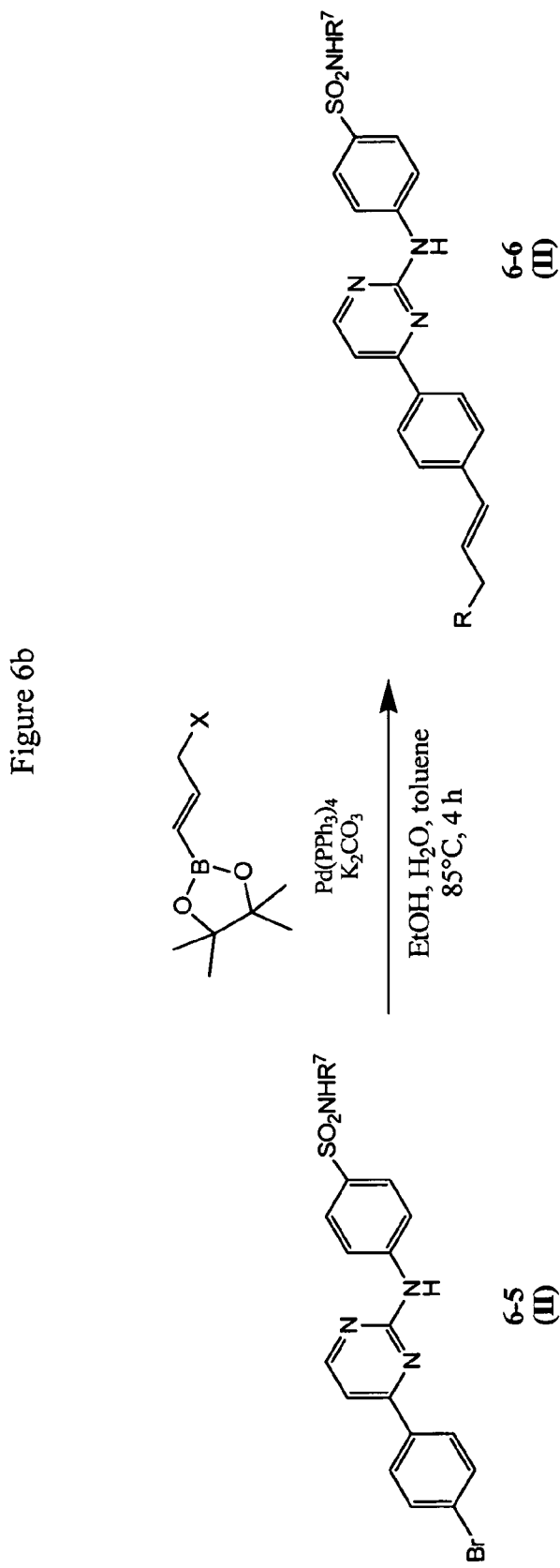
Figure 7:
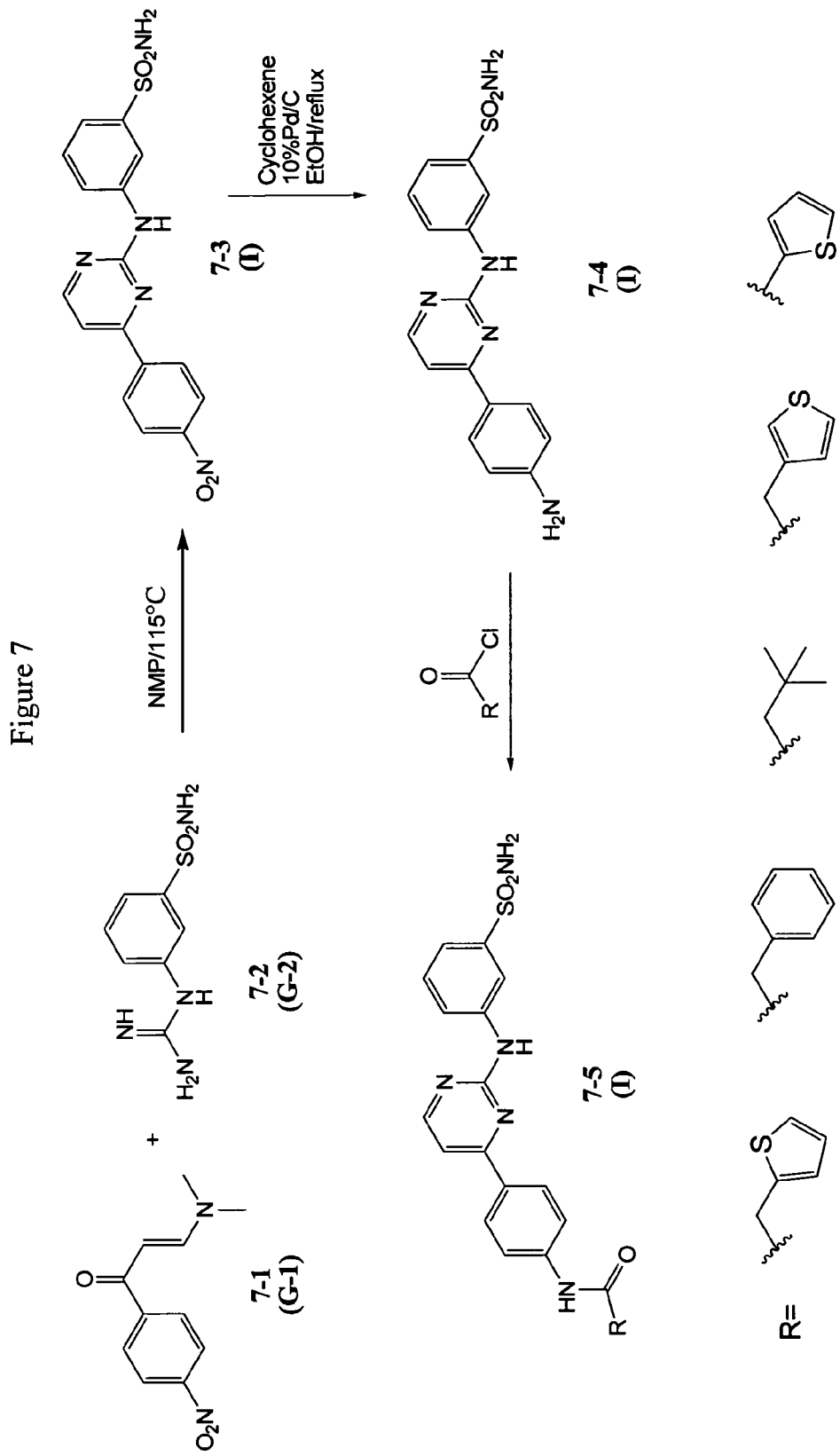
Figure 8:
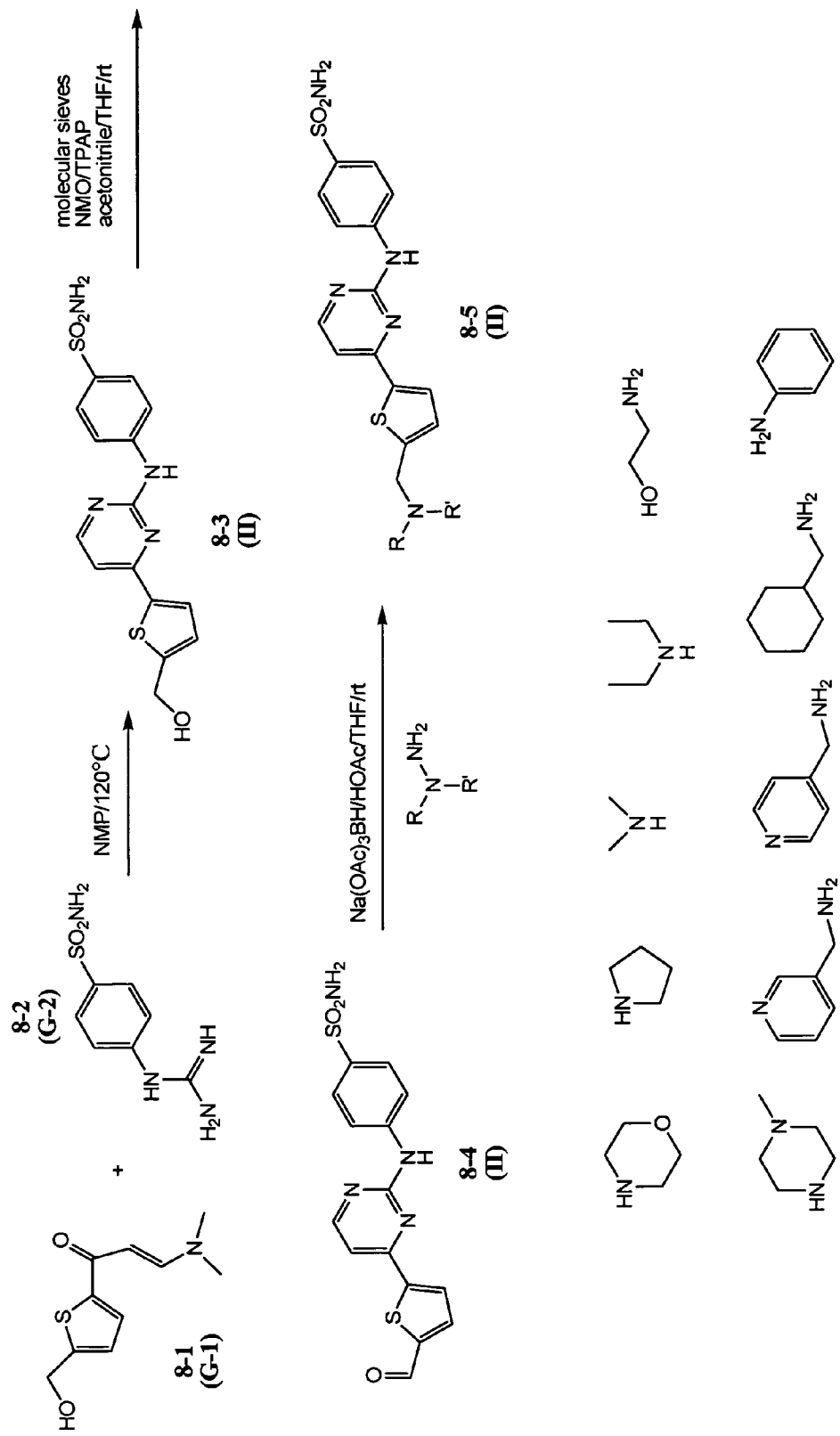

Preparation of 4-[(4-{4-[(1E)-3-hydroxyprop-1-en-1-yl]phenyl}pyrimidin-2-yl)amino]benzenesulfonamide (Exemplary Compound 272)
See FIGS. 6a and 6b

Step 1: Tert-Butyl(dimethyl){[(2E)-3-(4,4,5,5-tetramethyl-1,3,2-dioxaborolan-2-yl)prop-2-en-1-yl]oxy}silane A flask is charged with tert-butyl-dimethyl-prop-2-ynyloxy-silane (3.00 g, 17.6 mmol), 4,4,5,5-tetramethyl-1,2,3-dioxaborolane (2.80 ml, 2.50 g, 19.4 mmol), bis(cyclopentadienyl)zirconium (IV) chloride hydride (0.454 g, 1.76 mmol), and triethylamine (0.250 ml, 0.178 g, 1.76 mmol). The reaction mixture is stirred at 60° C. for 20 h. The reaction mixture is cooled to room temperature, diluted with hexane, and filtered through silica gel to yield 3.0 g of colorless oil. HRMS: calcd for C15H31BO3Si+H+, 299.22083; found (ESI-FTMS, [M+H]1+), 298.22459.

Step 2: 4-{[4-(4-bromophenyl)pyrimidin-2-yl]amino}benzenesulfonamide

A flask is charged with the 1-(4-bromo-phenyl)-3-dimethylamino-propenone (1.05 g, 4.10 mmol), 4-guanidino-benzenesulfonamide (1.33 g, 6.20 mmol), and NMP (30 ml). The reaction mixture is stirred at 120° C. for 20 h. The reaction mixture is cooled to room temperature, diluted with water, and filtered. The solid residue is washed with water and dried to yield 1.66 g of a white solid. MS (ESI) m/z 405.1; HRMS: calcd for C16H13BrN4O2S+H+, 405.00153; found (ESI-FTMS, [M+H]1+), 405.00158.

Step 3: 4-[(4-{4-[(1E)-3-hydroxyprop-1-en-1-yl]phenyl}pyrimidin-2-yl)amino]benzenesulfonamide A flask is charged with 4-{[4-(4-bromophenyl)pyrimidin-2-yl]amino}benzenesulfonamide (0.681 g, 1.68 mmol), tert-butyl(dimethyl){[(2E)-3-(4,4,5,5-tetramethyl-1,3,2-dioxaborolan-2-yl)prop-2-en-1-yl]oxy}silane (1.00 g, 3.35 mmol), (Ph3)4Pd (0.194 g, 0.168 mmol), potassium carbonate (0.695 g, 5.03 mmol), ethanol (3.0 ml), water (3.0 ml), and toluene (25 ml). The reaction mixture is stirred at 85° C. for 4 h. The reaction mixture is cooled to room temperature, and trifluoroacetic acid (1.0 ml) is added. The reaction mixture is then stirred for 16 h at room temperature. The reaction mixture is concentrated and purified on preparative HPLC to yield 0.196 g of a yellow solid. MS (ESI) m/z 383.2; HRMS: calcd for C19H18N4O3S+H+, 383.11724; found (ESI-FTMS, [M+H]1+), 383.11752.

Exemplary compounds 269, 270, 272, 280-285 and 298 can be synthesized according to this method.

Example 7

A vial is charged with the anilino-pyrimidine, N,N-diethyl aniline, and NMP. The mixture is cooled to 0° C., and acyl chloride is added. The reaction is warmed to room temperature and stirred for 4 hours. Water is added, and the precipitate is washed with ether, DCM.

Exemplary compounds 221-225 can be synthesized according to this method.

Example 8

The aldehyde is dissolved in THF and cooled to 0° C. The amine is added, followed by Na(OAc)3BH, and the reaction is stirred at 0° C. for 15 minutes. HOAc is added dropwise, and the reaction is warmed to room temperature for 3 hours. The reaction is quenched with water. The product is extracted with ethyl acetate, washed with sodium bicarbonate and brine, and purified with EtOAc/MeOH (10:1).

Exemplary compounds 132-134, 141, and 143-149 can be synthesized according to this method.

Scheme 2: Halogen Displacement

Example 9

General Experimental for the Preparation of 2-anilino-4-aryl/heteroarylpyrimidine Sulfonamide Secondary and Tertiary Sulfonamides. See FIG. 9

Figure 9:
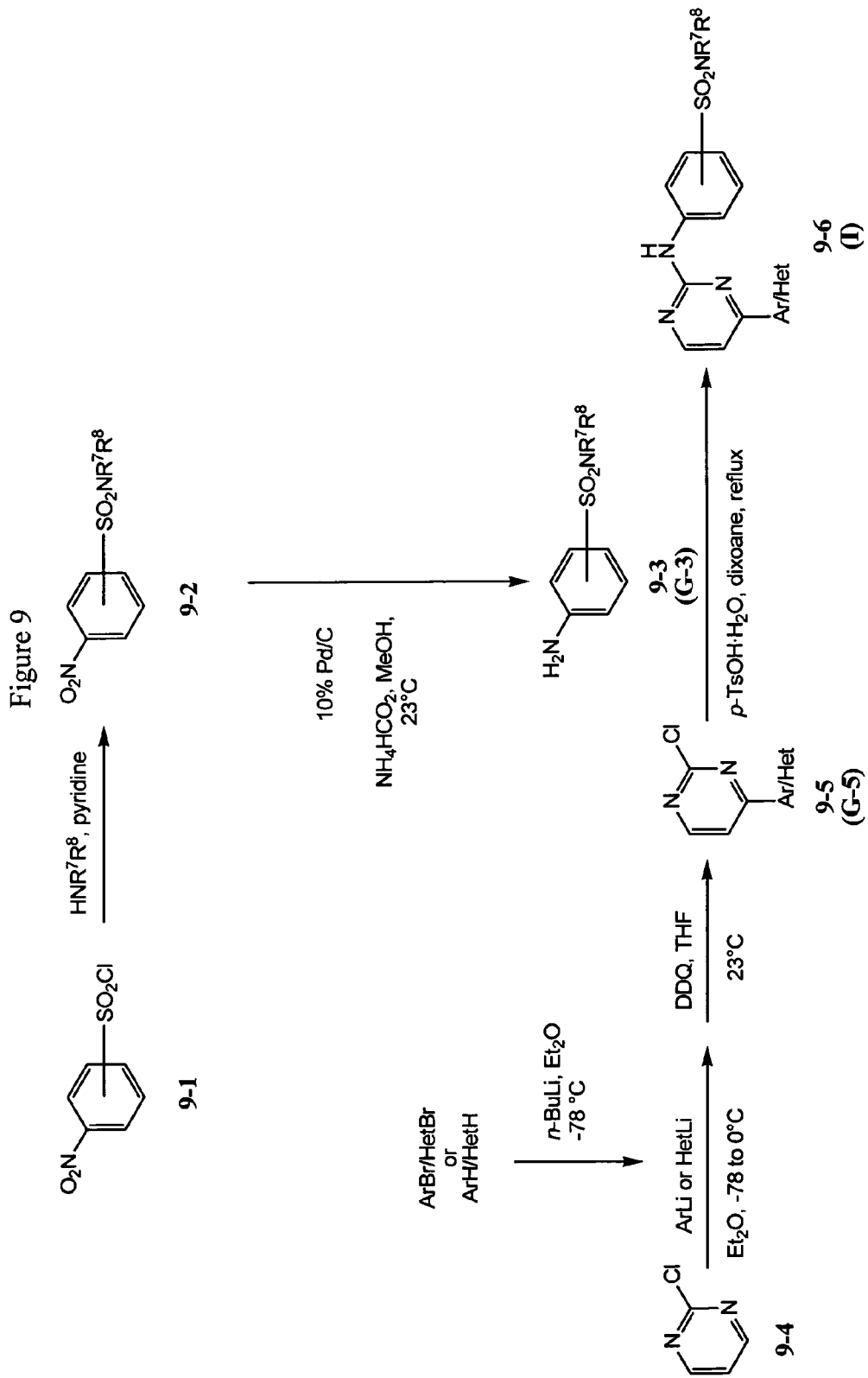
FIGS. 9-14 depict exemplary halogen displacement reactions.

Amino sulfonamides (G-3) can be purchased commercially or prepared by the process depicted in FIG. 9: nitrobenzenesulfonyl chlorides (9-1) can be converted to the corresponding sulfonamides (9-2) via reaction with $HNR^7R^8$ in an amine solvent such as pyridine or in a polar aprotic solvent such as $CH_2Cl_2$ or THF in the presence of a hindered amine base such as I—$Pr_2NEt$ or $Et_3N$ and DMAP. These nitrobenzenesulfonamides (9-2) can be reduced to the corresponding amines using conditions such as 10% Pd/C, $NH_4HCO_2$, MeOH, or $SnCl_2.H_2O$, EtOH, heat or Fe, HCl, EtOH, $H_2O$, heat.

Step 1: Preparation of Substituted-4-nitro-benzenesulfonamides (9-2)

1.25 eq of i-$Pr_2NEt$, 0.1 equiv. of DMAP, and 1.25 equiv. of amine is added to 1 equiv. of 4-nitrobenzenesulfonyl chloride as a 0.1 M solution in $CH_2Cl_2$. This mixture is stirred at 23° C. until judged complete by TLC. After quenching with sat. $NaHCO_3$ solution and separating the organic and aqueous layers, the organic layer is evaporated to yield nearly pure 4-nitrobenzenesulfonamides as off-white to colorless solids (Yield range: 56-100% yields).

Step 2: Preparation of 4-amino-benzenesulfonamide Secondary and Tertiary Sulfonamides (G-3)

0.1 wt. equiv. of 10% Pd/C and 5 equiv. of ammonium formate is added to 1 eq of a 4-nitrobenzenesulfonamide as a 0.1 M solution in MeOH. The mixture is stirred at 23° C. for 8 h. Filtration through celite and evaporation gives the title compound as an off-white solid or a colorless oil.

Step 3: Preparation of 2-chloro-4-aryl/heteroaryl-pyrimidine (G-5)

To a −30° C. solution of a Ar/HetLi (10.66 mmol, 1.08 eq, generated via deprotonation of Li for Br exchange) in 20 ml of $Et_2O$, is added portion wise a suspension of 2-chloropyrimidine (9.84 mmol, 1 equiv.) in 20 ml $Et_2O$ in 2 ml portions over 15 min. The resulting suspension is stirred for 30 min at −30° C. and at 0° C. for 60 min. The reaction is quenched with $H_2O$ (0.27 ml, 1.5 equiv.) in THF (3 ml), and DDQ (2.95 g, 10.66 mmol, 1 equiv.) in THF (15 ml) is then added. The resulting suspension is stirred at 23° C. for 15 min, and then cooled to 0° C. Hexanes (10 ml) are added followed by a 0° C. solution of NaOH (10 ml, 3N). The suspension is stirred for 5 min at 0° C. 100 ml of $H_2O$ is added, and the layers are separated. The organic layer is dried ($Na_2SO_4$) and concentrated in vacuo. Purification via $SiO_2$ gel column chromatography gives the title compound.

Step 4: Preparation of 2-anilino-4-aryl/heteroarylpyrimidine Sulfonamide Primary, Secondary, and Tertiary Sulfonamides (I)

Aniline target molecules of structure (I) can be prepared by reacting 2-chloropyrimidine (9-4) with aryl or heteroaryllithiums, prepared by reacting aryl bromides/heteroaryl bromides with a strong base such as n-BuLi, MeLi or PhLi or via deprotonation of aryls/heteroaryls with a strong base such as n-BuLi, MeLi, PhLi, LDA, or $LiN(TMS)_2$, followed by oxidation with DDQ to give 4-aryl/heteroaryl-2-chloropyrimidines (G-5) according to the procedures of Czarny and Harden. (Strekowski, L et al., *J Heterocyclic. Chem.* 1990, 27, 1393, and Harden D. B. et al., *J Org. Chem.* 1988, 53, 4137). A subsequent reaction with amino sulfonamides (G-3) in hot dioxane in the presence of p-TsOH.$H_2O$ gives the desired 2-aminopyrimidine sulfonamides (I) based on the procedure of Hattinger (Hattinger, G. et al., GB 2369359).

A 2-chloro-4-aryl/heteroaryl pyrimidine (0.26 mmol, 1 equiv.), aniline (0.26 mmol, 1 equiv.), and 1,4-dioxane (2 mL) solution is combined with a solution of p-TsOH (0.21 mmol, 0.8 eq) and 1,4-dioxane (1 ml). The resulting suspension is heated at 100° C. for 12-18 h. Reaction progress is monitored using an analytical HP Agilent 1100 LC/MS.

HPLC: Analytical Method and Parameters:

Instrument: HP Agilent 1100 LC/MS

UV Detector: Agilent 1100 Diode Array Detector

Mass Spectrometer Detector: Agilent MSD

Column: Waters Xterra MS C18 30 mm×2.1 mm i.d., 3.5 um

Flow Rate: 1.00 ml/min

Run Time: 5.00 min

Gradient Elution: 0 min 90% water, 10% acetonitrile; 3 min 10% water, 90% acetonitrile Column Temperature: 50° C.

UV Signals: 215 nm, 254 nm

MS Parameters: Mass Range 100-1000, Fragmentor 140, Gain EMV 1.0

After cooling to 23° C., all volatiles are removed in a Speed Vac. This crude material is dissolved in 0.5 ml DMSO: 1.5 ml MeCN, filtered through a 0.45 µm GMF, and purified on a Gilson HPLC, using a Phenomenex LUNA $C_{18}$ column: 60 mm×21.20 mm I.D., 5 um particle size: with ACN/water (containing 0.2% TFA or $Et_3N$) gradient elution. The appropriate fractions are analyzed by LC/MS. The title compound is isolated by combining pure fractions and evaporating the solvent in a Speed Vac.

Exemplary compounds 2, 3, 71-79, 86, and 87 can be synthesized according to this method.

HPLC Conditions: Instrument—Agilent 1100; Column: Keystone Aquasil C18 (as above); Mobile Phase A: 10 mM $NH_4OAC$ in 95% water/5% CAN; Mobile Phase B: 10 mM $NH_{40}AC$ in 5% water/95% CAN; Flow Rate: 0.800 ml/min; Column Temperature: 40° C.; Injection Volume: 5 ul; UV: monitor 215, 230, 254, 280, and 300 nm; Purity is reported at 254 nm unless otherwise noted.

| Gradient Table: | |
| --- | --- |
| Time (min) | % B |
| 0.0 | 0 |
| 2.5 | 100 |
| 4.0 | 100 |
| 4.1 | 0 |
| 5.6 | 0 |

MS Conditions: Instrument: Agilent MSD; Ionization Mode: API-ES; Gas Temperature: 350 C; Drying Gas: 11.0 L/min.; Nebulizer Pressure: 55 psig; Polarity: 50% positive, 50% negative; VCap: 3000 V (positive), 2500 V (negative); Fragmentor: 80 (positive), 120 (negative); Mass Range: 100-1000 m/z; Threshold: 150; Step size: 0.15; Gain: 1; Peak width: 0.15 min Example 10

General Experimental for the Preparation of 2-N(Me)-anilino-4-aryl/heteroarylpyrimidine Sulfonamides. See FIG. 10

Figure 10:
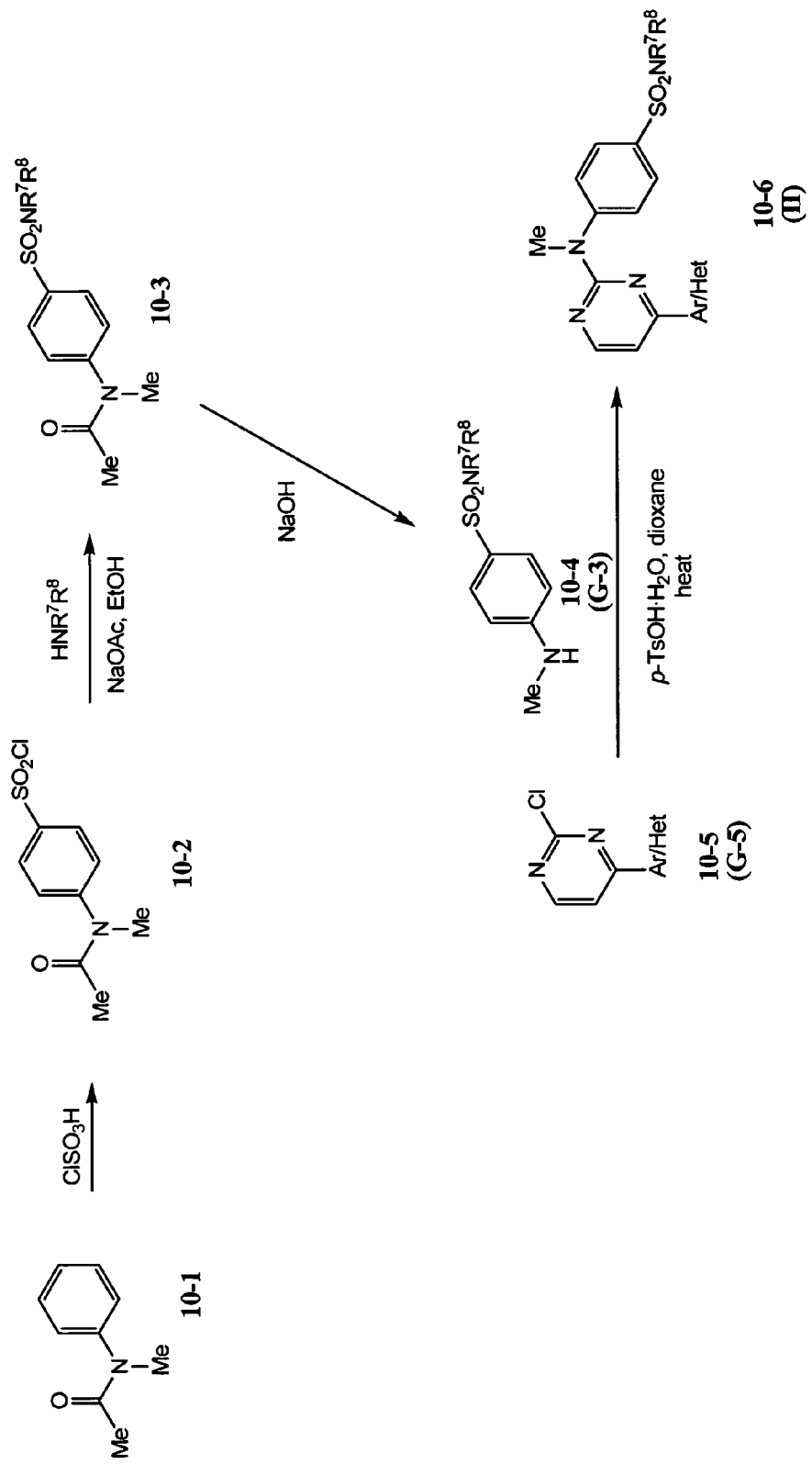

4-Methylaminobenzene sulfonamides (10-6) are prepared according to the process depicted in FIG. 10. N-methyl acetamide (10-1) can be converted to sulfonyl chloride (10-2) according to the procedure of Stojanovic (Stojanovic, O. K. et al. *Chem. Abstr.* 1973, 3902) using neat $ClSO_3H$. The sulfonyl chloride is converted to the corresponding sulfonamides (10-3) using amines, NaOAc in EtOH, and NaOH hydrolysis of the acetyl group to produce the desired 4-methylaminobenzene sulfonamides (10-4) according to the procedure of Oinuma (Oinuma, H. et al. *J. Med. Chem.* 1991, 34, 2260).

N-Methylaminosulfonamide analogs can be prepared according to the process depicted in FIG. 10. 4-aryl/heteroaryl-2-chloropyrimidines (10-5) are combined with 4-methylaminobenzene sulfonamides (10-4) in hot dioxane in the presence of p-TsOH.$H_2O$ to give the desired N-methylaminosulfonamide sulfonamides (10-6).

Step 1: 4-(Acetyl-methyl-amino)-benzenesulfonyl Chloride (10-2)

(Based on the procedure of O. K. Stojanovic et al. *Chem. Abstr.* 1973, 78, 3902s.) N-Methyl-N-phenyl-acetamide (10.0 g, 67 mmol) is heated with 50 ml of $ClSO_3H$ at 70° C. for 90 min. The mixture is poured into 200 ml of ice, and the resulting product is filtered and washed with 2×25 ml of $H_2O$ to the give the title compound as an off-white solid.

Step 2: N-Substituted-N-(4-sulfamoyl-phenyl)-acetamides (10-3)

(Based on the procedure of H. Oinuma et al. *J. Med Chem.* 1991, 34, 2260-7.) 1 equiv. of 4-(acetyl-methyl-amino)-benzenesulfonyl chloride is added to a 0.1 M EtOH slurry of 1.1 equiv. of amine and 2.7 equiv. of NaOAc at 0° C. The mixture is stirred at 23° C. for 6 h. Water is added, and the mixture is extracted with 3×25 ml of EtOAc. The combined organics are washed with 1×50 ml of $H_2O$ and 1×50 ml brine, dried over $MgSO_4$, filtered and evaporated to give the title compound as an off-white solid or oil.

Step 3: 4-Methylamino-benzenesulfonamides (10-4)

A N-substituted-N-(4-sulfamoyl-phenyl)-acetamide (1 equiv.) is combined with 1 N aqueous NaOH to make a 0.1 M solution in acetamide. The resulting mixture is refluxed for 12 h. After cooling to 23° C., the reaction mixture is adjusted to pH~7 with 1 N aqueous HCl, and extracted with 2×25 ml EtOAc. The combined organics are washed with 1×50 ml $H_2O$, 1×50 ml brine, dried over $MgSO_4$, filtered and evaporated to give the title compound as a colorless solid or oil.

Step 4: 2-N(Me)-anilino-4-aryl/heteroarylpyrimidine Sulfonamides (10-6)

The protocol described in Example 9, Step 4 is used except that 4-methylamino-benezenesulfonamides are used in place of primary amino-benzenesulfonamides.

Exemplary compounds 80-85 can be synthesized according to this method.

HPLC Conditions: Instrument—Agilent 1100; Column: Keystone Aquasil C18 (as above); Mobile Phase A: 10 mM $NH_4OAC$ in 95% water/5% CAN; Mobile Phase B: 10 mM $NH_4OAC$ in 5% water/95% CAN; Flow Rate: 0.800 ml/min; Column Temperature: 40° C.; Injection Volume: 5 ul; UV: monitor 215, 230, 254, 280, and 300 nm; Purity is reported at 254 nm unless otherwise noted.

| Gradient Table: | |
| --- | --- |
| Time (min) | % B |
| 0.0 | 0 |
| 2.5 | 100 |
| 4.0 | 100 |
| 4.1 | 0 |
| 5.7 | 0 |

MS Conditions: Instrument: Agilent MSD; Ionization Mode: API-ES; Gas Temperature: 350 C; Drying Gas: 11.0 L/min.; Nebulizer Pressure: 55 psig; Polarity: 50% positive, 50% negative; VCap: 3000V (positive), 2500V (negative); Fragmentor: 80 (positive), 120 (negative); Mass Range: 100-1000 m/z; Threshold: 150; Step size: 0.15; Gain: 1; Peak width: 0.15 min Example 11

Figure 11:
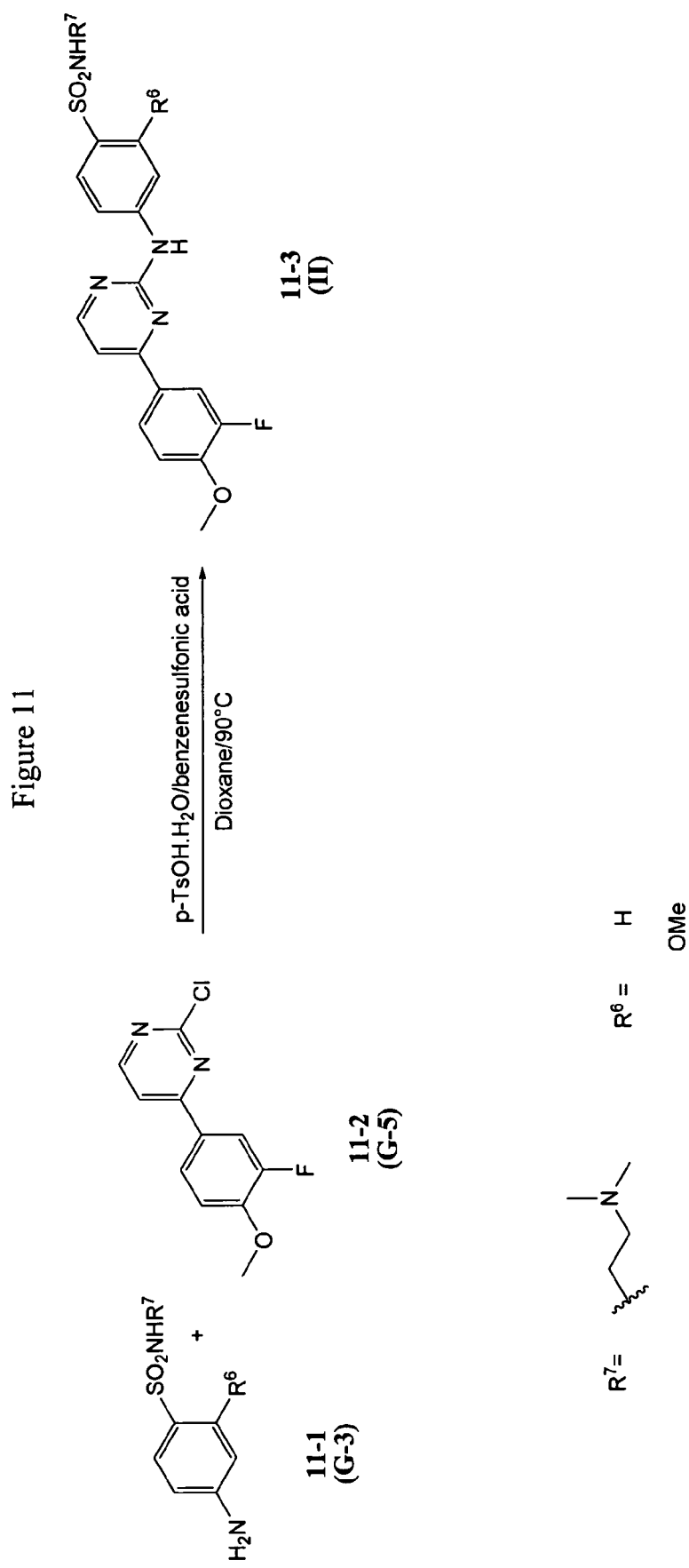
Figure 12:
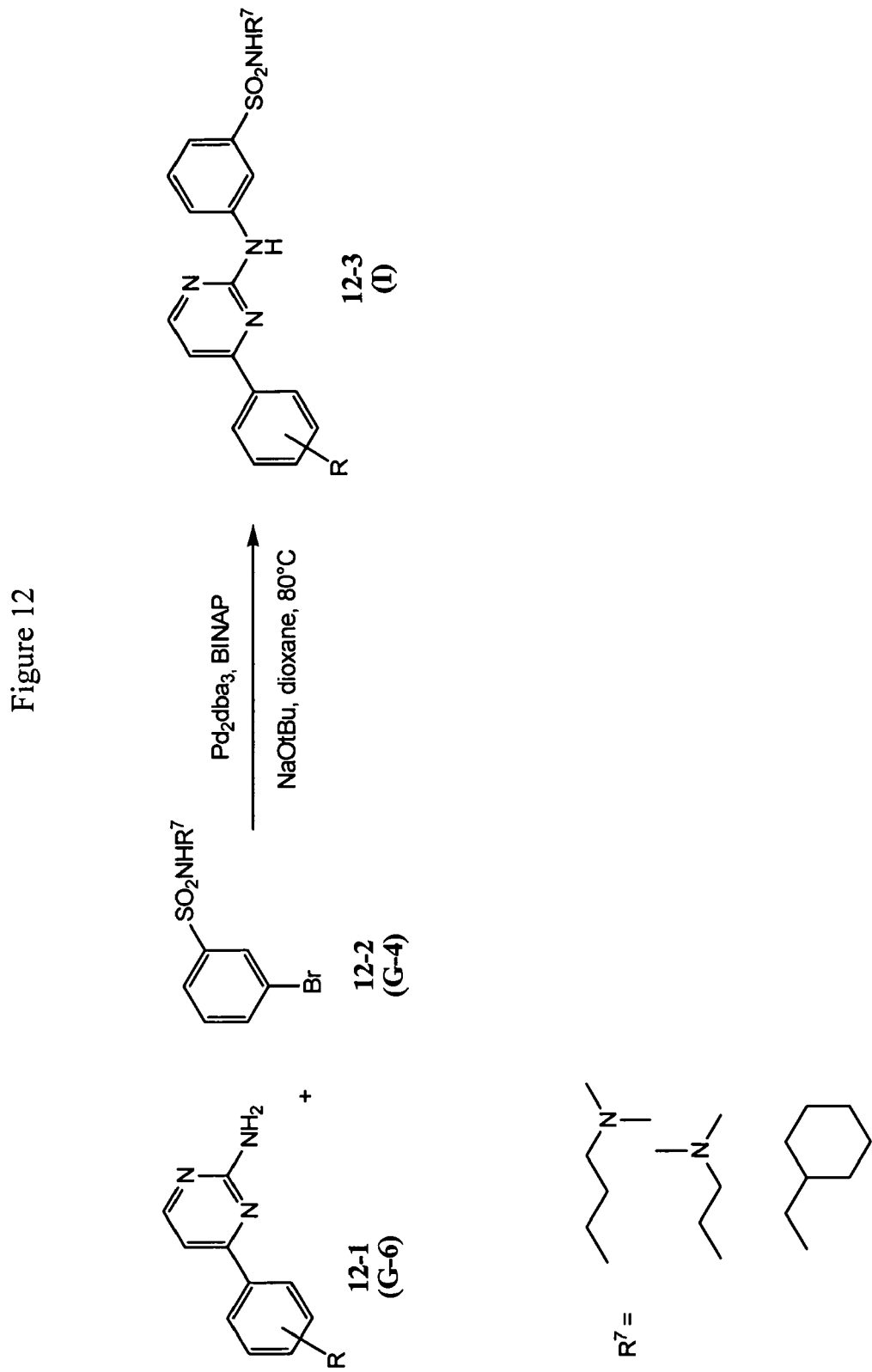
Figure 13:
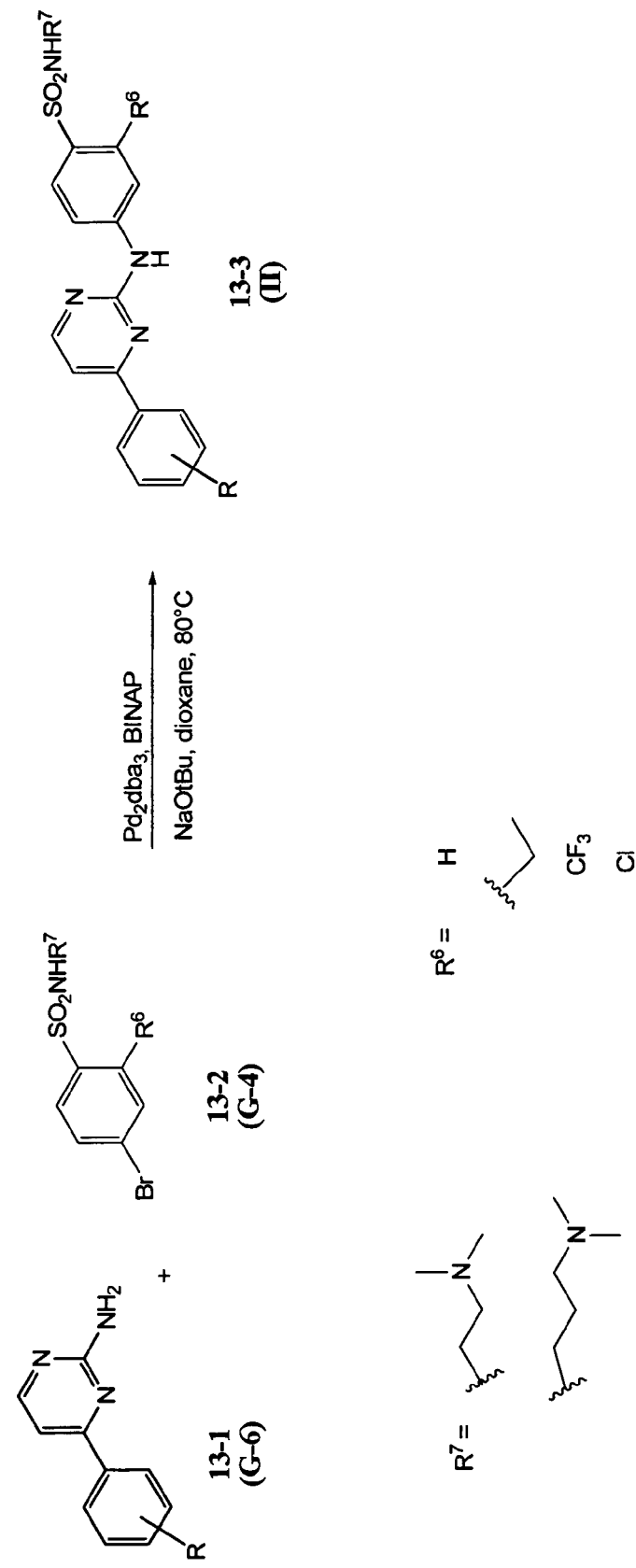
Figure 14:
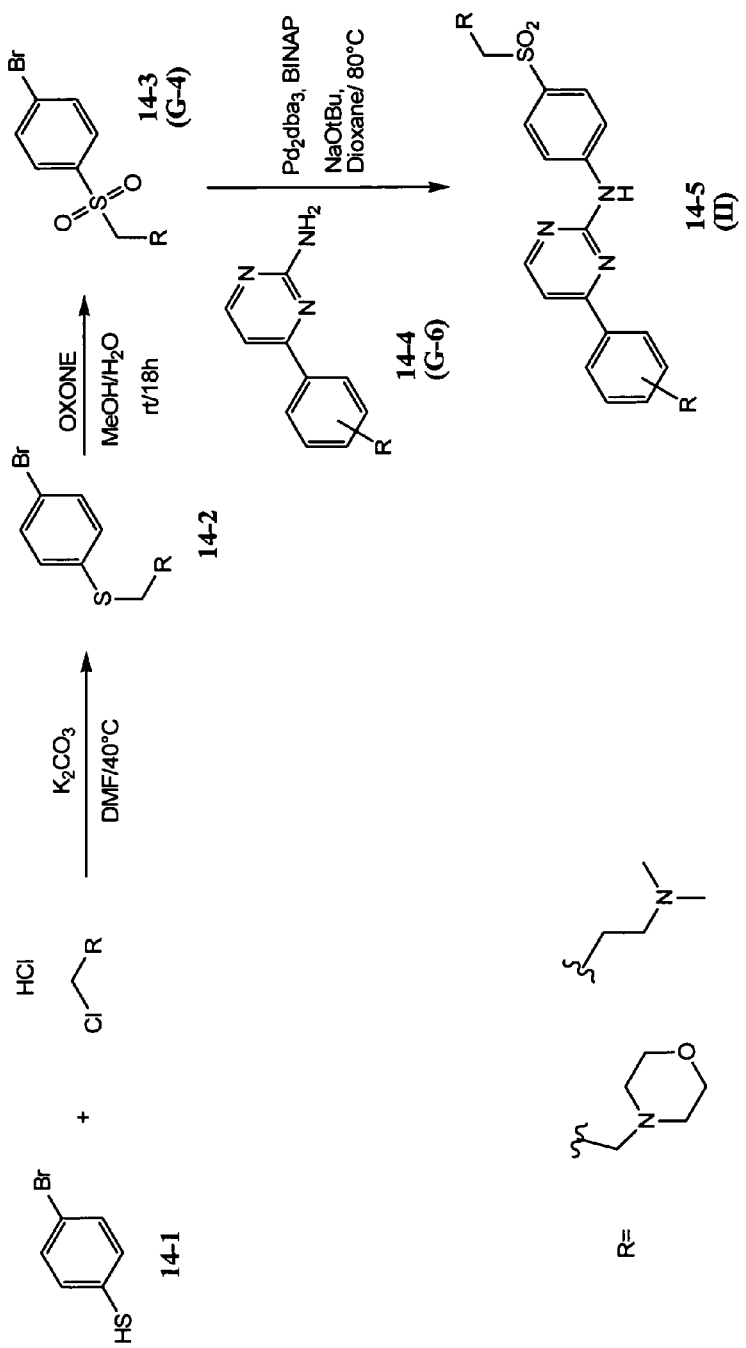

The starting materials are combined in a vial in dioxane and stirred at 90° C. overnight, then cooled to the room temperature. 50% $NaHCO_3$ is added, and the reaction is stirred for 10 minutes. The precipitate is filtered, then dissolved in THF, and purified by pre-plate with THF/MeOH (10:1). See FIG. 11.

Exemplary compound 184 can be synthesized according to this method.

Example 12

A halogenated (Br) sulfonamide (G-4) is reacted with a pyrimidine (G-6) by adding sodium tert-butoxide (NaOtBu) in the presence of tris(dibenzylideneacetone)dipalladium(0) ($Pd_2dba_3$) and 2,2'-bis(diphenylphosphino)-1,1'-binaphthyl (BINAP).

Exemplary compounds 115-118, 123, 127, and 128 can be synthesized according to this method.

Example 13

Sodium t-butoxide is added to a stirred suspension of anilino-pyrimidines, substituted sulfonamides, tris(dibenzylideneacetone)dipalladium(0), and 2,2'-bis(diphenylphosphino)-1,1'-binaphthyl in dioxane. The mixture is heated at 80° C. for 50 hours. The reaction is cooled to room temperature, and the mixture is filtered and washed with THF and MeOH. The solvent is removed by evaporation, and the residue is purified by pre-plate with EtOAc/MeOH (10:1).

Exemplary compounds 130, 131, 139, 161-164, 166-169, 171-174, and 299 can be synthesized according to this method.

Example 14

Sodium t-butoxide is added to a stirred suspension of anilino-pyrimidines, substituted sulfones, tris(dibenzylideneacetone)dipalladium(0), and 2,2'-bis(diphenylphosphino)-1,1'-binaphthyl in dioxane. The mixture is heated at 80° C. for 72 hours. The reaction is cooled to room temperature, and the mixture is filtered and washed with THF and MeOH. The solvent is removed by evaporation, and the residue is purified by pre-plate with EtOAc/MeOH (10:1.5).

Exemplary compounds 98-103 can be synthesized according to this method.

IKK Kinase Assay

Example 15

Molecular Cloning and Expression of Flag IKKβ

Human IKKβ cDNA is amplified by reverse transcriptase-polymerase chain reaction from human placental RNA (CLONTECH) using primers that incorporated the FLAG-epitope at the C terminus of IKKβ. FLAG-IKKβ is inserted into the baculovirus expression plasmid pFASTBAC (Life Technologies). Following the manufacturer's protocol for the BAC-TO-BAC (Life Technologies) Baculovirus Expression System, recombinant baculoviruses expressing the IKKP enzyme are made. Briefly, $9 \times 10^5$ SF9 cells per well of a 6-well plate are transfected with one µg of miniprep bacmid DNA using the CellFECTIN™ reagent. Virus is harvested 72 hours post transfection, and a viral titer is performed, after which a high titer viral stock ($2 \times 10^8$ pfu/ml) is amplified by three to four rounds of infection.

Example 16

Flag-IKKβ Protein Production and Purification

Using the high titer stock of baculovirus expressing the Flag-IKKβ, 200 mL of SF9 cells at a density of $1 \times 10^6$ cells/mL are infected at a multiplicity of infection (MOI) of approximately 5 at 27° C. in SF-900 II SFM medium. Cells are harvested 48-54 hours later by centrifugation at 500×g in a Sorvall centrifuge. The resulting pellets are frozen at <20° C. until purification.

For protein purification, the pellets are thawed on ice and resuspended in cell lysis buffer (50 mM HEPES, pH 7.5, 100 mM NaCl, 1% NP-40, 10% glycerol, 1 mM $Na_3VO_4$, 1 mM EDTA, 1 mM DTT, and protease inhibitor cocktail from Pharmingen). After Dounce homogenization, the cells are put in the cold room on a rotator for 30 minutes. The NaCl concentration is adjusted to 250 mM and the cell debris is removed by centrifugation at 18000×g. The resulting supernatant is loaded onto an anti-FLAG M2 agarose affinity column (Sigma) at 4° C. and the column is washed with 60 mL of wash buffer (50 mM HEPES, pH 7.5, 300 mM NaCl, 10% glycerol, 1 mM $Na_3VO_4$, 1 mM EDTA, and 1 mM PMSF). The FLAG-IKKβ is eluted using 200 µg/mL Flag peptide (Sigma) in elution buffer (50 mM HEPES, pH 7.5, 100 mM NaCl, 10% glycerol, 1 mM $Na_3VO_4$, 1 mM EDTA, 1 mM DTT, and protease inhibitor cocktail from Pharmingen) in 500 µL aliquots, which are tested for protein levels using SDS-PAGE followed by Coomassie Blue staining (BioRad). After testing for activity as described below, fractions with high IKK enzyme activity are combined, aliquotted, and stored at −80° C.

Example 17

IKK Kinase Assay

LANCE reactions are carried out based upon the suggestions of Wallac/Perkin Elmer. Purified Flag-IKKβ enzyme (2 nM final concentration) is typically used in the kinase reaction buffer described above supplemented with 0.0025% Brij solution (Sigma) to help stabilize the enzyme. Biotinylated substrate IκBα (1-54) is synthesized and purified (>95% pure) and is used at 500 nM final concentration. ATP is used at a final concentration of 2 µM. The total reaction volumes are 25 µL and the inhibitor compounds are preincubated with enzyme before substrate and ATP are added. Reactions are conducted for 30 minutes at room temperature in black, low binding plates (Dynex). 25 µL of 20 mM EDTA is added to terminate the reactions and then 100 µL of detection mixture [0.25 nM Europium labeled anti-phospho-IκBα (prepared by Wallac) and 0.25 µg/mL final concentration streptavidin-APC, Wallac] is added 30 minutes before reading the plates in a Wallac VICTOR plate reader. The energy transfer signal data is used to calculate percent inhibition and $IC_{50}$ values.

Example 18

Western Analysis of IκBα

Hela cells are plated at 6-well plate for 24 hours and treated with compounds for 30 min before the addition of TNFα (10 µg/ml). After one hour, Hela cells are harvested in MPER reagent (Pierce, Rockford, Ill.) containing 400 mM NaCl. Protein from all samples is quantified by the Bradford method. Cell lysates containing 30 µg of protein are electrophoresed on a 12% SDS-PAGE gel and transferred to a PVDF membrane using a Bio Rad liquid transfer apparatus. The PVDF membrane is incubated in TBST (TBS with 0.1% Tween-20) with 3% milk for 15 minutes before the addition of the first antibody, mouse anti-IκBα (Santa Cruz). After overnight incubation, the PVDF membrane is washed 3 times with TBST and incubated with secondary antibodies coupled with horseradish peroxidase (Transduction Labs) for one hour. The PVDF membrane is then washed 3 times with TBST and protein is detected using an enhanced chemiluminescence detection system (Pierce).

Exemplary compounds 4, 6-9, 11, 14, 16, 22, 25, 26, 29, 30, 32, 34, 39-52, 54-56, 57, 58-66, 68, 88-92, 95, 96, 98, 100-107, 109-113, 115-121, 125, 126, 129-136, 138-146, 150, 152, 153, 156-158, 160-164, 166, 168-170, 173, 174, 176-178, 180-186, 188-204, 208-210, 212, 215, 216, 219-225, 229, 230, 232-241, 245, 246, 250, 251, 253, 256-258, 260, 262-266, 268, 270, 272, 277, 283-285, 287, and 289 gave a positive result.

Exemplary compounds 10, 21, 27, 28, 31, 33, 35, 37, 53, 67, 97, 122, 123, 137, 147-149, 151, 154, 155, 159, 165, 167, 171, 172, 175, 187, 206, 207, 213, 214, 217, 218, 226, 227, 228, 243, 244, 247-249, 254, 269, 271, 276, and 280-282 gave a slightly positive result.

What is claimed is:

1. A compound selected from the group consisting of:
N-phenyl-4-[(4-thien-2-ylpyrimidin-2-yl)amino]benzenesulfonamide;
N-methyl-4-[(4-thien-2-ylpyrimidin-2-yl)amino]benzenesulfonamide;
4-[4-(5-Chloro-thiophen-2-yl)-pyrimidin-2-ylamino]-benzenesulfonamide;
4-({4-[4-fluoro-3-(trifluoromethyl)phenyl]pyrimidin-2-yl}amino)benzenesulfonamide;
4-{[4-(4-methoxyphenyl)pyrimidin-2-yl]amino}-N,N-dimethylbenzenesulfonamide;
or a pharmaceutically acceptable salt thereof.

2. A compound selected from the group consisting of:
4-{[4-(3,4-difluorophenyl)pyrimidin-2-yl]amino}benzenesulfonamide;
4-[(4-thien-2-ylpyrimidin-2-yl)amino]benzenesulfonamide;
4-{[4-(5-nitrothien-2-yl)pyrimidin-2-yl]amino}benzenesulfonamide;
4-{[4-(4-methylphenyl)pyrimidin-2-yl]amino}benzenesulfonamide;
4-{[4-(2-methylphenyl)pyrimidin-2-yl]amino}benzenesulfonamide;
or a pharmaceutically acceptable salt thereof.

3. A compound selected from the group consisting of:
4-{[4-(3-methylthien-2-yl)pyrimidin-2-yl]amino}benzenesulfonamide;
4-{[4-(4-methoxy-3-methylphenyl)pyrimidin-2-yl]amino}benzenesulfonamide;
4-{[4-(2-hydroxyphenyl)pyrimidin-2-yl]amino}benzenesulfonamide;
4-{[4-(3-fluorophenyl)pyrimidin-2-yl]amino}benzenesulfonamide;
4-{[4-(2-hydroxy-5-methylphenyl)pyrimidin-2-yl]amino}benzenesulfonamide;
or a pharmaceutically acceptable salt thereof.

4. A compound selected from the group consisting of:
4-{[4-(3-hydroxyphenyl)pyrimidin-2-yl]amino}benzenesulfonamide;
4-{[4-(3-chlorophenyl)pyrimidin-2-yl]amino}benzenesulfonamide;
4-{[4-(2-chlorophenyl)pyrimidin-2-yl]amino}benzenesulfonamide;
4-{[4-(2-fluorophenyl)pyrimidin-2-yl]amino}benzenesulfonamide;
4-[(4-phenylpyrimidin-2-yl)amino]benzenesulfonamide;
or a pharmaceutically acceptable salt thereof.

5. A compound selected from the group consisting of:
4-{[4-(2,4-dimethoxyphenyl)pyrimidin-2-yl]amino}benzenesulfonamide;
4-[(4-bicyclo[2.2.1]hept-5-en-2-ylpyrimidin-2-yl)amino]benzenesulfonamide;
4-({4-[4-(trifluoromethyl)phenyl]pyrimidin-2-yl}amino)benzenesulfonamide;
4-{[4-(4-chlorophenyl)pyrimidin-2-yl]amino}benzenesulfonamide;
4-{[4-(4-cyclohexylphenyl)pyrimidin-2-yl]amino}benzenesulfonamide;
or a pharmaceutically acceptable salt thereof.

6. A compound selected from the group consisting of:
4-{[4-(4-cyanophenyl)pyrimidin-2-yl]amino}benzenesulfonamide;
4-{[4-(4-methoxyphenyl)pyrimidin-2-yl]amino}benzenesulfonamide;
4-{[4-(4-morpholin-4-ylphenyl)pyrimidin-2-yl]amino}benzenesulfonamide;
4-{[4-(4-isobutylphenyl)pyrimidin-2-yl]amino}benzenesulfonamide;
4-{[4-(4-propylphenyl)pyrimidin-2-yl]amino}benzenesulfonamide;
or a pharmaceutically acceptable salt thereof.

7. A compound selected from the group consisting of:
4-{[4-(4-isopropylphenyl)pyrimidin-2-yl]amino}benzenesulfonamide;
4-{[4-(4-vinylphenyl)pyrimidin-2-yl]amino}benzenesulfonamide;
4-[4-(5-Pyridin-2-ylethynyl-thiophen-2-yl)-pyrimidin-2-ylamino]-benzenesulfonamide;
4-[(4-{5-[(4-aminophenyl)ethynyl]thien-2-yl}pyrimidin-2-yl)amino]benzenesulfonamide;
(2E)-3-[5-(2-{[4-(aminosulfonyl)phenyl]amino}pyrimidin-4-yl)thien-2-yl]-N,N-dimethylacrylamide;
or a pharmaceutically acceptable salt thereof.

8. A compound selected from the group consisting of:
2-(dimethylamino)ethyl (2E)-3-[5-(2-{[4-(aminosulfonyl)phenyl]amino}pyrimidin-4-yl)thien-2-yl]acrylate;
N-[4-(Morpholin-4-ylsulfonyl)phenyl]-4-[4-(trifluoromethyl)phenyl]pyrimidin-2-amine;
N-(3-morpholin-4-ylpropyl)-4-({4-[4-(trifluoromethyl)phenyl]pyrimidin-2-yl}amino)benzenesulfonamide;
4-{[4-(4-methoxyphenyl)pyrimidin-2-yl]amino}-N-(3-morpholin-4-ylpropyl)benzenesulfonamide;
4-{[4-(4-methylphenyl)pyrimidin-2-yl]amino}-N-(3-morpholin-4-ylpropyl)benzenesulfonamide;
or a pharmaceutically acceptable salt thereof.

9. A compound selected from the group consisting of:
2-{4-[(4-{[4-(4-methoxyphenyl)pyrimidin-2-yl]amino}phenyl)sulfonyl]piperazin-1-yl}ethanol;
4-({4-[4-(methylsulfonyl)phenyl]pyrimidin-2-yl}amino)-N-(3-morpholin-4-ylpropyl)benzenesulfonamide;
4-{[4-(1,3-benzodioxol-5-yl)pyrimidin-2-yl]amino}-N-(3-morpholin-4-ylpropyl)benzenesulfonamide;
N-(3-morpholin-4-ylpropyl)-4-({4-[4-(trifluoromethoxy)phenyl]pyrimidin-2-yl}amino)benzenesulfonamide;
4-{[4-(3,4-dimethoxyphenyl)pyrimidin-2-yl]amino}-N-(3-morpholin-4-ylpropyl)benzenesulfonamide;
or a pharmaceutically acceptable salt thereof.

10. A compound selected from the group consisting of:
4-{[4-(3-fluoro-4-methoxyphenyl)pyrimidin-2-yl]amino}-N-(3-morpholin-4-ylpropyl)benzenesulfonamide;
4-{[4-(3,4-dimethoxyphenyl)pyrimidin-2-yl]amino}-N-(2-morpholin-4-ylethyl)benzenesulfonamide;
N-(2-morpholin-4-ylethyl)-4-({4-[4-(trifluoromethoxy)phenyl]pyrimidin-2-yl}amino)benzenesulfonamide;
4-({4-[4-(methylsulfonyl)phenyl]pyrimidin-2-yl}amino)-N-(2-morpholin-4-ylethyl)benzenesulfonamide;
4-{[4-(3-fluoro-4-methoxyphenyl)pyrimidin-2-yl]amino}-N-(2-morpholin-4-ylethyl)benzenesulfonamide;
or a pharmaceutically acceptable salt thereof.

11. A compound selected from the group consisting of:
4-{[4-(4-fluorophenyl)pyrimidin-2-yl]amino}-N-(2-morpholin-4-ylethyl)benzenesulfonamide;

4-{[4-(4-bromophenyl)pyrimidin-2-yl]amino}-N-(2-morpholin-4-ylethyl)benzenesulfonamide;
4-{[4-(4-methoxyphenyl)pyrimidin-2-yl]amino}-N-(2-morpholin-4-ylethyl)benzenesulfonamide;
4-{[4-(1,3-benzodioxol-5-yl)pyrimidin-2-yl]amino}-N-(2-morpholin-4-ylethyl)benzenesulfonamide;
4-{[4-(4-hydroxyphenyl)pyrimidin-2-yl]amino}-N-(2-morpholin-4-ylethyl)benzenesulfonamide;

or a pharmaceutically acceptable salt thereof.

12. A compound selected from the group consisting of:
4-{[4-(4-chlorophenyl)pyrimidin-2-yl]amino}-N-(2-morpholin-4-ylethyl)benzenesulfonamide;
4-{[4-(4-chlorophenyl)pyrimidin-2-yl]amino}-N-[3-(dimethylamino)propyl]benzenesulfonamide;
N-[3-(dimethylamino)propyl]-4-({4-[4-(methylsulfonyl)phenyl]pyrimidin-2-yl}amino)benzenesulfonamide;
N-[2-(dimethylamino)ethyl]-4-{[4-(4-methoxyphenyl)pyrimidin-2-yl]amino}benzenesulfonamide;
N-[2-(dimethylamino)ethyl]-4-{[4-(3-fluoro-4-methoxyphenyl)pyrimidin-2-yl]amino}benzenesulfonamide;

or a pharmaceutically acceptable salt thereof.

13. A compound selected from the group consisting of:
N-[2-(dimethylamino)ethyl]-4-({4-[4-(methylsulfonyl)phenyl]pyrimidin-2-yl}amino)benzenesulfonamide;
4-{[4-(4-chlorophenyl)pyrimidin-2-yl]amino}-N-[2-(dimethylamino)ethyl]benzenesulfonamide;
N-[3-(dimethylamino)propyl]-4-{[4-(4-hydroxyphenyl)pyrimidin-2-yl]amino}benzenesulfonamide;
N-[2-(dimethylamino)ethyl]-4-{[4-(4-hydroxyphenyl)pyrimidin-2-yl]amino}benzenesulfonamide;
N-morpholin-4-yl-4-({4-[4-(trifluoromethyl)phenyl]pyrimidin-2-yl}amino)benzenesulfonamide;

or a pharmaceutically acceptable salt thereof.

14. A compound selected from the group consisting of:
N-(3-hydroxypropyl)-4-({4-[4-(trifluoromethyl)phenyl]pyrimidin-2-yl}amino)-benzenesulfonamide;
3-{[4-(3-methylpyrazin-2-yl)pyrimidin-2-yl]amino}benzenesulfonamide; 3-({4-[4-(methylsulfonyl)phenyl]pyrimidin-2-yl}amino)benzenesulfonamide;
N-isobutyl-4-[(4-thien-3-ylpyrimidin-2-yl)amino]benzenesulfonamide;
4-{[4-(1-methyl-1H-pyrrol-2-yl)pyrimidin-2-yl]amino}-N-phenylbenzenesulfonamide;

or a pharmaceutically acceptable salt thereof.

15. A compound selected from the group consisting of:
N-methyl-4-{[4-(1-methyl-1H-pyrrol-2-yl)pyrimidin-2-yl]amino}benzenesulfonamide;
N-isobutyl-4-{[4-(1-methyl-1H-pyrrol-2-yl)pyrimidin-2-yl]amino}benzenesulfonamide;
4-{[4-(5-bromothien-2-yl)pyrimidin-2-yl]amino}-N-methylbenzenesulfonamide;
N-[4-(dimethylamino)phenyl]-4-{[4-(1-naphthyl)pyrimidin-2-yl]amino}benzenesulfonamide;
N-(4-{[2-(methoxymethyl)pyrrolidin-1-yl]sulfonyl}phenyl)-4-(1-naphthyl)pyrimidin-2-amine;

or a pharmaceutically acceptable salt thereof.

16. A compound selected from the group consisting of:
N-methyl-4-{[4-(3-methylthien-2-yl)pyrimidin-2-yl]amino}benzenesulfonamide;
N-isobutyl-4-{[4-(3-methylthien-2-yl)pyrimidin-2-yl]amino}benzenesulfonamide;
N-(4-{[(2S)-2-(methoxymethyl)pyrrolidin-1-yl]sulfonyl}phenyl)-N-methyl-4-(2-thienyl)pyrimidin-2-amine;
4-{methyl[4-(5-methyl-2-thienyl)pyrimidin-2-yl]amino}benzenesulfonamide;
4-[[4-(5-bromo-2-thienyl)pyrimidin-2-yl](methyl)amino]benzenesulfonamide;

or a pharmaceutically acceptable salt thereof.

17. A compound selected from the group consisting of:
N-methyl-4-{methyl[4-(5-methyl-2-thienyl)pyrimidin-2-yl]amino}benzenesulfonamide;
N-methyl-4-{methyl[4-(2-thienyl)pyrimidin-2-yl]amino}benzenesulfonamide; 4-[[4-(5-bromo-2-thienyl)pyrimidin-2-yl](methyl)amino]-N-methylbenzenesulfonamide;
N-methyl-3-{[4-(2-naphthyl)pyrimidin-2-yl]amino}benzenesulfonamide;
N-isobutyl-3-{[4-(2-naphthyl)pyrimidin-2-yl]amino}benzenesulfonamide;

or a pharmaceutically acceptable salt thereof.

18. A compound selected from the group consisting of:
4-{[4-(5-bromo-2-thienyl)pyrimidin-2-yl]amino}benzenesulfonamide;
ethyl 4-{2-[(4-{[(3-morpholin-4-ylpropyl)amino]sulfonyl}phenyl)amino]pyrimidin-4-yl}benzoate;
4-{[4-(5-methylthien-2-yl)pyrimidin-2-yl]amino}-N-(3-morpholin-4-ylpropyl)benzenesulfonamide;
4-{[4-(4-ethoxyphenyl)pyrimidin-2-yl]amino}-N-(3-morpholin-4-ylpropyl)benzenesulfonamide;
4-({4-[4-(dimethylamino)phenyl]pyrimidin-2-yl}amino)-N-(3-morpholin-4-ylpropyl)benzenesulfonamide;

or a pharmaceutically acceptable salt thereof.

19. A compound selected from the group consisting of:
5-(2-{[4-(aminosulfonyl)phenyl]amino}pyrimidin-4-yl)-2-methoxybenzenesulfonamide;
4-{2-[(4-{[(3-morpholin-4-ylpropyl)amino]sulfonyl}phenyl)amino]pyrimidin-4-yl}benzoic acid;
N-[2-(dimethylamino)ethyl]-5-(2-{[4-({[2-(dimethylamino)ethyl]amino}sulfonyl)phenyl]amino}pyrimidin-4-yl)-2-methoxybenzenesulfonamide;
2-methoxy-N-methyl-5-[2-({4-[(methylamino)sulfonyl]phenyl}amino)pyrimidin-4-yl]benzenesulfonamide;
N-(2-hydroxyethyl)-5-{2-[(4-{[(2-hydroxyethyl)amino]sulfonyl}phenyl)amino]pyrimidin-4-yl}-2-methoxy-benzenesulfonamide;

or a pharmaceutically acceptable salt thereof.

20. A compound selected from the group consisting of:
4-(4-methoxyphenyl)-N-{4-[(2-piperidin-1-ylethyl)sulfonyl]phenyl}pyrimidin-2-amine;
4-(4-methoxyphenyl)-N-{4-[(2-morpholin-4-ylethyl)sulfonyl]phenyl}pyrimidin-2-amine;
4-(3-fluoro-4-methoxyphenyl)-N-{4-[(2-morpholin-4-ylethyl)sulfonyl]phenyl}pyrimidin-2-amine;
N-(4-{[3-(dimethylamino)propyl]sulfonyl}phenyl)-4-(4-methoxyphenyl)pyrimidin-2-amine;
N-(4-{[3-(dimethylamino)propyl]sulfonyl}phenyl)-4-(3-fluoro-4-methoxyphenyl)pyrimidin-2-amine;

or a pharmaceutically acceptable salt thereof.

21. A compound selected from the group consisting of:
4-(3-fluoro-4-methoxyphenyl)-N-{4-[(2-piperidin-1-ylethyl)sulfonyl]phenyl}pyrimidin-2-amine;
4-{[4-(4-hydroxyphenyl)pyrimidin-2-yl]amino}benzenesulfonamide;
4-{[4-(5-bromo-2-thienyl)pyrimidin-2-yl]amino}-N-[2-[(dimethylamino)ethyl]benzenesulfonamide;
4-{[4-(4,4-dimethyl-2-oxo-1,4-dihydro-2H-3,1-benzoxazin-6-yl)pyrimidin-2-yl]amino}benzenesulfonamide;
4-{[4-(3,5-difluoro-4-methoxyphenyl)pyrimidin-2-yl]amino}benzenesulfonamide;

or a pharmaceutically acceptable salt thereof.

22. A compound selected from the group consisting of:
4-{[4-(2-oxo-2H-chromen-3-yl)pyrimidin-2-yl]
amino}benzenesulfonamide;
4-{[4-(3-methyl-2-oxo-2,3-dihydro-1,3-benzoxazol-6-yl)
pyrimidin-2-yl]amino}benzenesulfonamide;
4-{[4-(2-oxo-2,3-dihydro-1,3-benzoxazol-6-yl)pyrimidin-2-yl]amino}benzenesulfonamide;
N-[2-(dimethylamino)ethyl]-4-({4-[4-(trifluoromethyl)
phenyl]pyrimidin-2-yl}amino)benzenesulfonamide;
N-[3-(dimethylamino)propyl]-4-({4-[4-(trifluoromethyl)
phenyl]pyrimidin-2-yl}amino)benzenesulfonamide;
or a pharmaceutically acceptable salt thereof.

23. A compound selected from the group consisting of:
N-[3-(1H-imidazol-1-yl)propyl]-4-({4-[4-(trifluoromethyl)phenyl]pyrimidin-2-yl}amino)benzenesulfonamide;
N-4H-1,2,4-triazol-4-yl-4-({4-[4-(trifluoromethyl)phenyl]pyrimidin-2-yl}amino)benzenesulfonamide;
N-[3-(dimethylamino)propyl]-3-{[4-(3-fluoro-4-methoxyphenyl)pyrimidin-2-yl]amino}benzenesulfonamide;
N-[3-(dimethylamino)propyl]-3-{[4-(4-methoxyphenyl)pyrimidin-2-yl]amino}benzenesulfonamide;
N-[2-(dimethylamino)ethyl]-3-{[4-(3-fluoro-4-methoxyphenyl)pyrimidin-2-yl]amino}benzenesulfonamide;
or a pharmaceutically acceptable salt thereof.

24. A compound selected from the group consisting of:
N-[2-(dimethylamino)ethyl]-3-{[4-(4-methoxyphenyl)pyrimidin-2-yl]amino}benzenesulfonamide;
N-(2-morpholin-4-ylethyl)-4-({4-[4-(trifluoromethyl)phenyl]pyrimidin-2-yl}amino)benzenesulfonamide;
N-[2-hydroxy-1-(hydroxymethyl)ethyl]-4-({4-[4-(trifluoromethyl)phenyl]pyrimidin-2-yl}amino)benzenesulfonamide;
N-(2-hydroxyethyl)-4-({4-[4-(trifluoromethyl)phenyl]pyrimidin-2-yl}amino)benzenesulfonamide;
ethyl N-{[4-({4-[4-(trifluoromethyl)phenyl]pyrimidin-2-yl}amino)phenyl]sulfonyl}glycinate;
or a pharmaceutically acceptable salt thereof.

25. A compound selected from the group consisting of:
N-[3-(dimethylamino)propyl]-3-{[4-(4-hydroxyphenyl)pyrimidin-2-yl]amino}benzenesulfonamide;
N-{[4-({4-[4-(trifluoromethyl)phenyl]pyrimidin-2-yl]amino)phenyl}sulfonyl}glycine;
3-{[4-(3-fluoro-4-methoxyphenyl)pyrimidin-2-yl]amino}benzenesulfonamide;
N-[3-(dimethylamino)propyl]-4-{[4-(3-fluoro-4-methoxyphenyl)pyrimidin-2-yl]amino}benzenesulfonamide;
3-{[4-(3-fluoro-4-methoxyphenyl)pyrimidin-2-yl]amino}-N-(3-phenylpropyl)benzenesulfonamide;
or a pharmaceutically acceptable salt thereof.

26. A compound selected from the group consisting of:
N-(cyclohexylmethyl)-3-{[4-(3-fluoro-4-methoxyphenyl)pyrimidin-2-yl]amino}benzenesulfonamide;
3-{[4-(3-fluoro-4-hydroxyphenyl)pyrimidin-2-yl]amino}benzenesulfonamide;
N-[2-(dimethylamino)ethyl]-4-{[4-(3-fluoro-4-hydroxyphenyl)pyrimidin-2-yl]amino}benzenesulfonamide;
N-[3-(dimethylamino)propyl]-4-{[4-(3-fluoro-4-hydroxyphenyl)pyrimidin-2-yl]amino}benzenesulfonamide;
4-({4-[5-(hydroxymethyl)-2-thienyl]pyrimidin-2-yl}amino)benzenesulfonamide;
or a pharmaceutically acceptable salt thereof.

27. A compound selected from the group consisting of:
4-{[4-(5-formyl-2-thienyl)pyrimidin-2-yl]amino}benzenesulfonamide;
4-({4-[5-(morpholin-4-ylmethyl)-2-thienyl]pyrimidin-2-yl}amino)benzenesulfonamide;
N-[(5-methylpyrazin-2-yl)methyl]-4-({4-[4-(trifluoromethyl)phenyl]pyrimidin-2-yl}amino)benzenesulfonamide;
N-(pyridin-2-ylmethyl)-4-({4-[4-(trifluoromethyl)phenyl]pyrimidin-2-yl}amino)benzenesulfonamide;
N-(pyridin-3-ylmethyl)-4-({4-[4-(trifluoromethyl)phenyl]pyrimidin-2-yl}amino)benzenesulfonamide;
or a pharmaceutically acceptable salt thereof.

28. A compound selected from the group consisting of:
N-(pyridin-4-ylmethyl)-4-({4-[4-(trifluoromethyl)phenyl]pyrimidin-2-yl}amino)benzenesulfonamide;
4-{[4-(3-fluoro-4-methoxyphenyl)pyrimidin-2-yl]amino}-N-(3-hydroxypropyl)benzenesulfonamide;
4-(4-methoxyphenyl)-N-{4-[(1-methyl-1H-imidazol-2-yl)sulfonyl]phenyl}pyrimidin-2-amine;
4-({4-[5-(pyrrolidin-1-ylmethyl)-2-thienyl]pyrimidin-2-yl}amino)benzenesulfonamide;
4-[(4-{5-[(dimethylamino)methyl]-2-thienyl}pyrimidin-2-yl)amino]benzenesulfonamide;
or a pharmaceutically acceptable salt thereof.

29. A compound selected from the group consisting of:
4-[(4-{5-[(diethylamino)methyl]-2-thienyl}pyrimidin-2-yl)amino}benzenesulfonamide;
4-{[4-(5-{[(2-hydroxyethyl)amino]methyl}-2-thienyl)pyrimidin-2-yl]amino}benzenesulfonamide;
4-[(4-{5-[(4-methylpiperazin-1-yl)methyl]-2-thienyl}pyrimidin-2-yl)amino}benzenesulfonamide;
4-{[4-(5-{[(pyridin-3-ylmethyl)amino]methyl}-2-thienyl)pyrimidin-2-yl]amino}benzenesulfonamide;
4-{[4-(5-{[(pyridin-4-ylmethyl)amino]methyl}-2-thienyl)pyrimidin-2-yl]amino}benzenesulfonamide;
or a pharmaceutically acceptable salt thereof.

30. A compound selected from the group consisting of:
4-{[4-(5-{[(cyclohexylmethyl)amino]methyl}-2-thienyl)pyrimidin-2-yl]amino}benzenesulfonamide;
4-({4-[5-(anilinomethyl)-2-thienyl]pyrimidin-2-yl}amino)benzenesulfonamide;
4-[2-({4-[(1-methyl-1H-imidazol-2-yl)sulfonyl]phenyl}amino)pyrimidin-4-yl]phenol;
N-[4-(2-{[4-(aminosulfonyl)phenyl]amino}pyrimidin-4-yl)phenyl]-3-cyclopentylpropanamide;
N-[4-(2-{[4-(aminosulfonyl)phenyl]amino}pyrimidin-4-yl)phenyl]-2-phenylacetamide or a pharmaceutically acceptable salt thereof.

31. A compound selected from the group consisting of:
N-[4-(2-{[4-(aminosulfonyl)phenyl]amino}pyrimidin-4-yl)phenyl]-2-(2-thienyl)acetamide;
N-[4-(2-{[4-(aminosulfonyl)phenyl]amino}pyrimidin-4-yl)phenyl]nicotinamide;
N-[4-(2-{[4-(aminosulfonyl)phenyl]amino}pyrimidin-4-yl)phenyl]-2-(ethylthio)nicotinamide;
N-[4-(2-{[4-(aminosulfonyl)phenyl]amino}pyrimidin-4-yl)phenyl]hexanamide;
N-[4-(2-{[4-(aminosulfonyl)phenyl]amino}pyrimidin-4-yl)phenyl]cyclopropanecarboxamide;
or a pharmaceutically acceptable salt thereof.

32. A compound selected from the group consisting of:
N-[4-(2-{[4-(aminosulfonyl)phenyl]amino}pyrimidin-4-yl)phenyl]cyclopentanecarboxamide;
4-(2-{[4-(1H-imidazol-2-ylsulfonyl)phenyl]amino}pyrimidin-4-yl)phenol;
2-chloro-5-{[4-(3-fluoro-4-methoxyphenyl)pyrimidin-2-yl]amino}benzenesulfonamide;
N-[2-(dimethylamino)ethyl]-2-ethyl-4-{[4-(3-fluoro-4-methoxyphenyl)pyrimidin-2-yl]amino}benzenesulfonamide;

N-[2-(dimethylamino)ethyl]-2-ethyl-4-{[4-(4-methoxyphenyl)pyrimidin-2-yl]amino}benzenesulfonamide;
or a pharmaceutically acceptable salt thereof.

33. A compound selected from the group consisting of:
N-[3-(dimethylamino)propyl]-2-ethyl-4-{[4-(3-fluoro-4-methoxyphenyl)pyrimidin-2-yl]amino}benzenesulfonamide;
N-[3-(dimethylamino)propyl]-2-ethyl-4-{[4-(4-methoxyphenyl)pyrimidin-2-yl]amino}benzenesulfonamide;
2-chloro-5-{[4-(4,4-dimethyl-2-oxo-1,4-dihydro-2H-3,1-benzoxazin-6-yl)pyrimidin-2-yl]amino}benzenesulfonamide;
N-[3-(dimethylamino)propyl]-4-{[4-(3-fluoro-4-methoxyphenyl)pyrimidin-2-yl]amino}-2-(trifluoromethyl)benzenesulfonamide;
N-[2-(dimethylamino)ethyl]-4-{[4-(3-fluoro-4-methoxyphenyl)pyrimidin-2-yl]amino}-2-(trifluoromethyl)benzenesulfonamide;
or a pharmaceutically acceptable salt thereof.

34. A compound selected from the group consisting of:
N-[3-(dimethylamino)propyl]-4-{[4-(4-methoxyphenyl)pyrimidin-2-yl]amino}-2-(trifluoromethyl)benzenesulfonamide;
N-[2-(dimethylamino)ethyl]-4-{[4-(4-methoxyphenyl)pyrimidin-2-yl]amino}-2-(trifluoromethyl)benzenesulfonamide;
4-(3-fluoro-4-methoxyphenyl)-N-{4-[(1-methyl-1H-imidazol-2-yl)sulfonyl]phenyl}pyrimidin-2-amine;
2-chloro-N-[2-(dimethylamino)ethyl]-4-{[4-(3-fluoro-4-methoxyphenyl)pyrimidin-2-yl]amino}benzenesulfonamide;
2-chloro-N-[2-(dimethylamino)ethyl]-4-{[4-(4-methoxyphenyl)pyrimidin-2-yl]amino}benzenesulfonamide;
or a pharmaceutically acceptable salt thereof.

35. A compound selected from the group consisting of:
2-chloro-N-[3-(dimethylamino)propyl]-4-{[4-(3-fluoro-4-methoxyphenyl)pyrimidin-2-yl]amino}benzenesulfonamide;
2-chloro-N-[3-(dimethylamino)propyl]-4-{[4-(4-methoxyphenyl)pyrimidin-2-yl]amino}benzenesulfonamide;
3-{[4-(4,4-dimethyl-2-oxo-1,4-dihydro-2H-3,1-benzoxazin-6-yl)pyrimidin-2-yl]amino}benzenesulfonamide;
5-{[4-(3-fluoro-4-methoxyphenyl)pyrimidin-2-yl]amino}-2-methylbenzenesulfonamide;
N-{4-[(1-methyl-1H-imidazol-2-yl)sulfonyl]phenyl}-4-[5-(pyrrolidin-1-ylmethyl)-2-thienyl]pyrimidin-2-amine;
or a pharmaceutically acceptable salt thereof.

36. A compound selected from the group consisting of:
N-{4-[(1-methyl-1H-imidazol-2-yl)sulfonyl]phenyl}-4-{5-[(4-methylpiperazin-1-yl)methyl]-2-thienyl}pyrimidin-2-amine;
4-[4-(benzyloxy)phenyl]-N-{4-[(1-methyl-1H-imidazol-2-yl)sulfonyl]phenyl}pyrimidin-2-amine;
N-{4-[(4-methylpiperazin-1-yl)sulfonyl]phenyl}-4-(4-nitrophenyl)pyrimidin-2-amine;
4-(4-aminophenyl)-N-{4-[(4-methylpiperazin-1-yl)sulfonyl]phenyl}pyrimidin-2-amine
N-[3-(dimethylamino)propyl]-4-{[4-(4-nitrophenyl)pyrimidin-2-yl]amino}benzenesulfonamide
or a pharmaceutically acceptable salt thereof.

37. A compound selected from the group consisting of:
4-{[4-(4-aminophenyl)pyrimidin-2-yl]amino}-N-[3-(dimethylamino)propyl]benzenesulfonamide;
N-[2-(dimethylamino)ethyl]-4-{[4-(3-fluoro-4-methoxyphenyl)pyrimidin-2-yl]amino}-2-methoxybenzenesulfonamide;
N-[4-(2-{[4-({[3-(dimethylamino)propyl]amino}sulfonyl)phenyl]amino}pyrimidin-4-yl)phenyl]-2-(2-thienyl)acetamide;
N-[2-(dimethylamino)ethyl]-4-{[4-(4-nitrophenyl)pyrimidin-2-yl]amino}benzenesulfonamide;
phenyl [4-(2-{[4-({[3-(dimethylamino)propyl]amino}sulfonyl)phenyl]amino}pyrimidin-4-yl)phenyl]carbamate;
or a pharmaceutically acceptable salt thereof.

38. A compound selected from the group consisting of:
N-{4-[2-({4-[(4-methylpiperazin-1-yl)sulfonyl]phenyl}amino)pyrimidin-4-yl]phenyl}-2-(2-thienyl)acetamide;
4-{[4-(4-aminophenyl)pyrimidin-2-yl]amino}-N-[2-(dimethylamino)ethyl]benzenesulfonamide;
N-[4-(2-{[4-({[2-(dimethylamino)ethyl]amino}sulfonyl)phenyl]amino}pyrimidin-4-yl)phenyl]-2-(2-thienyl)acetamide;
N-[2-(dimethylamino)ethyl]-4-{[4-(3-thienyl)pyrimidin-2-yl]amino}benzenesulfonamide;
N-[3-(dimethylamino)propyl]-4-{[4-(3-thienyl)pyrimidin-2-yl]amino}benzenesulfonamide;
or a pharmaceutically acceptable salt thereof.

39. A compound selected from the group consisting of:
N-(2-hydroxyethyl)-4-{[4-(3-thienyl)pyrimidin-2-yl]amino}benzenesulfonamide;
N-[4-(2-{[4-({[3-(dimethylamino)propyl]amino}sulfonyl)phenyl]amino}pyrimidin-4-yl)phenyl]-3-methylbutanamide;
N-[4-(2-{[4-({[3-(dimethylamino)propyl]amino}sulfonyl)phenyl]amino}pyrimidin-4-yl)phenyl]-2-phenylacetamide;
N-[4-(2-{[4-({[3-(dimethylamino)propyl]amino}sulfonyl)phenyl]amino}pyrimidin-4-yl)phenyl]-2-(4-methoxyphenyl)acetamide;
N-[4-(2-{[4-({[3-(dimethylamino)propyl]amino}sulfonyl)phenyl]amino}pyrimidin-4-yl)phenyl]-3-(2-thienyl)propanamide;
or a pharmaceutically acceptable salt thereof.

40. A compound selected from the group consisting of:
N-[4-(2-{[4-({[3-(dimethylamino)propyl]amino}sulfonyl)phenyl]amino}pyrimidin-4-yl)phenyl]-3,3-dimethylbutanamide;
N-[4-(2-{[4-({[3-(dimethylamino)propyl]amino}sulfonyl)phenyl]amino}pyrimidin-4-yl)phenyl]thiophene-2-carboxamide;
N-[4-(2-{[4-({[3-(dimethylamino)propyl]amino}sulfonyl)phenyl]amino}pyrimidin-4-yl)phenyl]-4-(2-thienyl)butanamide;
3,3-dimethyl-N-{4-[2-({4-[(4-methylpiperazin-1-yl)sulfonyl]phenyl}amino)pyrimidin-4-yl]phenyl}butanamide;
N-[4-(2-{[4-({[3-(dimethylamino)propyl]amino}sulfonyl)phenyl]amino}pyrimidin-4-yl)phenyl]-2-(3-thienyl)acetamide;
or a pharmaceutically acceptable salt thereof.

41. A compound selected from the group consisting of:
N-[4-(2-{[4-({[2-(dimethylamino)ethyl]amino}sulfonyl)phenyl]amino}pyrimidin-4-yl)phenyl]-3,3-dimethylbutanamide;
N-[4-(2-{[4-({[2-(dimethylamino)ethyl]amino}sulfonyl)phenyl]amino}pyrimidin-4-yl)phenyl]-2-phenylacetamide;
N-[2-(dimethylamino)ethyl]-N-({4-[(4-{[(3,3-dimethylbutanoyl)amino]phenyl}pyrimidin-2-yl)amino]phenyl}sulfonyl)-3,3-dimethylbutanamide;

N-[4-(2-{[4-({[2-(dimethylamino)ethyl]amino}sulfonyl)phenyl]amino}pyrimidin-4-yl)phenyl]thiophene-2-carboxamide;

N-[3-(dimethylamino)propyl]-4-[(4-{4-[(phenylsulfonyl)amino]phenyl}pyrimidin-2-yl)amino]benzenesulfonamide;

or a pharmaceutically acceptable salt thereof.

42. A compound selected from the group consisting of:

N-[4-(2-{[4-({[2-(d ethylamino)ethyl]amino}sulfonyl)phenyl]amino}pyrimidin-4-yl)phenyl]-2-(4-methoxyphenyl)acetamide;

N-[4-(2-{[4-({[2-(d ethylamino)ethyl]amino}sulfonyl)phenyl]amino}pyrimidin-4-yl)phenyl]-2-(3-thienyl)acetamide;

N-[4-(2-{[4-({[2-(d ethylamino)ethyl]amino}sulfonyl)phenyl]amino}pyrimidin-4-yl)phenyl]-4-(2-thienyl)butanamide;

N-{4-[2-({4-[(4-methylpiperazin-1-yl)sulfonyl]phenyl}amino) pyrimidin-4-yl]phenyl}thiophene-2-carboxamide;

N-{4-[2-({4-[(4-methylpiperazin-1-yl)sulfonyl]phenyl}amino) pyrimidin-4-yl]phenyl}-2-(3-thienyl)acetamide;

or a pharmaceutically acceptable salt thereof.

43. A compound selected from the group consisting of:

N-{4-[2-({4-[(4-methylpiperazin-1-yl)sulfonyl]phenyl}amino) pyrimidin-4-yl]phenyl}-2-phenylacetamide;

N-[2-(dimethylamino)ethyl]-4-(2-thienyl)-N-[(4-{[4-(4-{[4-(2-thienyl)butanoyl]amino}phenyl)pyrimidin-2-yl]amino}phenyl)sulfonyl]butanamide;

N-[2-(dimethylamino)ethyl]-2-phenyl-N-({4-[(4-{4-[(phenylacetyl)amino]phenyl}pyrimidin-2-yl)amino]phenyl}sulfonyl)acetamide;

N-[4-(2-{[4-({[2-(dimethylamino)ethyl]amino}sulfonyl)phenyl]amino}pyrimidin-4-yl)phenyl]-3-methylbutanamide;

N-[2-(dimethylamino)ethyl]-3-methyl-N-({4-[(4-{4-[(3-methylbutanoyl)amino]phenyl}pyrimidin-2-yl)amino]phenyl}sulfonyl)butanamide;

or a pharmaceutically acceptable salt thereof.

44. A compound selected from the group consisting of:

N-[2-(dimethylamino)ethyl]-3-(2-thienyl)-N-[(4-{[4-(4-{[3-(2-thienyl)propanoyl]amino}phenyl)pyrimidin-2-yl]amino}phenyl)sulfonyl]propanamide;

N-[4-(2-{[4-(aminosulfonyl)phenyl]amino}pyrimidin-4-yl)phenyl]-3-oxobutanamide;

N-[2-(dimethylamino)ethyl]-4-[(4-{4-[(phenylsulfonyl)amino]phenyl}pyrimidin-2-yl)amino]benzenesulfonamide;

N-[4-(2-{[3-(aminosulfonyl)phenyl]amino}pyrimidin-4-yl)phenyl]-2-(2-thienyl)acetamide;

N-[4-(2-{[3-(aminosulfonyl)phenyl]amino}pyrimidin-4-yl)phenyl]-2-phenylacetamide;

or a pharmaceutically acceptable salt thereof.

45. A compound selected from the group consisting of:

N-[4-(2-{[3-(aminosulfonyl)phenyl]amino}pyrimidin-4-yl)phenyl]-3,3-dimethylbutanamide;

N-[4-(2-{[3-(aminosulfonyl)phenyl]amino}pyrimidin-4-yl)phenyl]-2-(3-thienyl)acetamide;

N-[4-(2-{[3-(aminosulfonyl)phenyl]amino}pyrimidin-4-yl)phenyl]thiophene-2-carboxamide;

4-[4-(benzylamino)phenyl]-N-{4-[(4-methylpiperazin-1-yl)sulfonyl]phenyl}pyrimidin-2-amine;

4-{4-[(4-chloro-2-fluorobenzyl)amino]phenyl}-N-{4-[(4-methylpiperazin-1-yl)sulfonyl]phenyl}pyrimidin-2-amine;

or a pharmaceutically acceptable salt thereof.

46. A compound selected from the group consisting of:

4-{4-[(2,2-dimethylpropyl)amino]phenyl}-N-{4-[(4-methylpiperazin-1-yl)sulfonyl]phenyl}pyrimidin-2-amine;

N-[5-(2-{[4-(aminosulfonyl)phenyl]amino}pyrimidin-4-yl)-2-thienyl]-3,3-dimethylbutanamide;

4-({4-[4-(benzylamino)phenyl]pyrimidin-2-yl}amino)-N-[3-(dimethylamino)propyl]benzenesulfonamide;

N-(4-{[2-(dimethylamino)ethyl]sulfonyl}phenyl)-4-(4-nitrophenyl)pyrimidin-2-amine;

N-[2-(dimethylamino)ethyl]-4-[(4-{4-[(2,2-dimethylpropyl)amino]phenyl}pyrimidin-2-yl)amino]benzenesulfonamide;

or a pharmaceutically acceptable salt thereof.

47. A compound selected from the group consisting of:

N-(2-hydroxyethyl)-4-{[4-(4-nitrophenyl)pyrimidin-2-yl]amino}benzenesulfonamide;

N-[2-(dimethylamino)ethyl]-4-[(4-{4-[(3,3-dimethylbutyl)amino]phenyl}pyrimidin-2-yl)amino]benzenesulfonamide;

N-[3-(dimethylamino)propyl]-4-[(4-{4-[(2,2-dimethylpropyl)amino]phenyl}pyrimidin-2-yl)amino]benzenesulfonamide;

N-[3-(d ethylamino)propyl]-4-[(4-{4-[(3,3-dimethylbutyl)amino]phenyl}pyrimidin-2-yl)amino]benzenesulfonamide;

2-amino-5-{[4-(3-fluoro-4-methoxyphenyl)pyrimidin-2-yl]amino}benzenesulfonamide;

or a pharmaceutically acceptable salt thereof.

48. A compound selected from the group consisting of:

4-{[4-(4-aminophenyl)pyrimidin-2-yl]amino}-N-(2-hydroxyethyl)benzenesulfonamide;

N-(4-{2-[(4-{[(2-hydroxyethyl)amino]sulfonyl}phenyl)amino]pyrimidin-4-yl}phenyl)-3,3-dimethylbutanamide;

N-(4-{2-[(4-{[(2-hydroxyethyl)amino]sulfonyl}phenyl)amino]pyrimidin-4-yl}phenyl)-2-(2-thienyl)acetamide;

2-(4-chlorophenyl)-N-(4-{2-[(4-{[(2-hydroxyethyl)amino]sulfonyl}phenyl)amino]pyrimidin-4-yl}phenyl)acetamide;

4-[(4-{4-[(4-phenylpyrimidin-2-yl)amino]phenyl}pyrimidin-2-yl)amino]benzenesulfonamide;

or a pharmaceutically acceptable salt thereof.

49. A compound selected from the group consisting of:

4-{[4-(4-{[4-(5-methyl-2-thienyl)pyrimidin-2-yl]amino}phenyl)pyrimidin-2-yl]amino}benzenesulfonamide;

4-{[4-(3-oxo-3H-spiro[1-benzofuran-2,1'-cyclopropan]-5-yl)pyrimidin-2-yl]amino}benzenesulfonamide;

4-(4-aminophenyl)-N-(4-{[2-(dimethylamino)ethyl]sulfonyl}phenyl)pyrimidin-2-amine;

N-{4-[(4-methylpiperazin-1-yl)sulfonyl]phenyl}-4-{4-[(2-phenylethyl)amino]phenyl}pyrimidin-2-amine;

4-{4-[(2,2-dimethylbutyl)amino]phenyl}-N-{4-[(4-methylpiperazin-1-yl)sulfonyl]phenyl}pyrimidin-2-amine;

or a pharmaceutically acceptable salt thereof.

50. A compound selected from the group consisting of:

N-(4-{2-[(4-{[2-(dimethylamino)ethyl]sulfonyl}phenyl)amino]pyrimidin-4-yl}phenyl)-2-phenylacetamide;

N-(4-{2-[(4-{[2-(dimethylamino)ethyl]sulfonyl}phenyl)amino]pyrimidin-4-yl}phenyl)-2-(2-thienyl)acetamide;

N-(4-{2-[(4-{[2-(dimethylamino)ethyl]sulfonyl}phenyl)amino]pyrimidin-4-yl}phenyl)-3,3-dimethylbutanamide;

N-(4-{2-[(4-{[2-(dimethylamino)ethyl]sulfonyl}phenyl)
amino]pyrimidin-4-yl}phenyl)-2-(4-methoxyphenyl)
acetamide;
N-(4-{2-[(4-{[2-(dimethylamino)ethyl]sulfonyl}phenyl)
amino]pyrimidin-4-yl}phenyl)-3-methylbutanamide;
or a pharmaceutically acceptable salt thereof.

51. A compound selected from the group consisting of:
N-[4-(2-{[4-(aminosulfonyl)phenyl]amino}pyrimidin-4-
yl)phenyl]-2-pyrrolidin-1-ylacetamide;
N-(2,2-diethoxyethyl)-4-{[4-(2,3-dihydro-1-benzofuran-
5-yl)pyrimidin-2-yl]amino}benzenesulfonamide;
4-{[4-(4-nitrophenyl)pyrimidin-2-yl]amino}-N-(2-pyrro-
lidin-1-ylethyl)benzenesulfonamide;
4-{[4-(2,3-dihydro-1-benzofuran-5-yl)pyrimidin-2-yl]
amino}-N-(2-oxoethyl)benzenesulfonamide;
4-{[4-(4-{[(benzylamino)carbonothioyl]amino}phenyl)
pyrimidin-2-yl]amino}-N-[2-(dimethylamino)ethyl]
benzenesulfonamide;
or a pharmaceutically acceptable salt thereof.

52. A compound selected from the group consisting of:
4-(2-{[4-({[3-(dimethylamino)propyl]amino}sulfonyl)
phenyl]amino}pyrimidin-4-yl)phenyl acetate;
4-{[4-(4-aminophenyl)pyrimidin-2-yl]amino}-N-(2-pyr-
rolidin-1-ylethyl)benzenesulfonamide;
4-{[4-(3-fluoro-4-methoxyphenyl)pyrimidin-2-yl]
amino}-N-(2-pyrrolidin-1-ylethyl)benzenesulfona-
mide;
4-{[4-(4-bromophenyl)pyrimidin-2-yl]
amino}benzenesulfonamide;
4-{[4-(4-bromophenyl)pyrimidin-2-yl]amino}-N-[3-
(dimethylamino)propyl]benzenesulfonamide;
or a pharmaceutically acceptable salt thereof.

53. A compound selected from the group consisting of:
3,3-dimethyl-N-(4-{2-[(4-{[(2-pyrrolidin-1-ylethyl)
amino]sulfonyl}phenyl)amino]pyrimidin-4-yl}phenyl)
butanamide;
2-phenyl-N-(4-{2-[(4-{[(2-pyrrolidin-1-ylethyl)amino]
sulfonyl}phenyl)amino]pyrimidin-4-yl}phenyl)aceta-
mide;
4-(2-{[4-({acetyl[3-(dimethylamino)propyl]
amino}sulfonyl)phenyl]amino}pyrimidin-4-yl)phenyl
acetate;
N-(4-{2-[(4-{[(2-pyrrolidin-1-ylethyl)amino]
sulfonyl}phenyl)amino]pyrimidin-4-yl}phenyl)
thiophene-2-carboxamide;
4-[(4-{4-[(aminocarbonothioyl)amino]phenyl}pyrimidin-
2-yl)amino]-N-[3-(dimethylamino)propyl]benzene-
sulfonamide;
or a pharmaceutically acceptable salt thereof.

54. A compound selected from the group consisting of:
N-[3-(dimethylamino)propyl]-4-[(4-{4-[(4-methyl-1,3-
thiazol-2-yl)amino]phenyl}pyrimidin-2-yl)amino]ben-
zenesulfonamide;
4-[(4-{4-[(1E)-3-(dimethylamino)prop-1-en-1-yl]
phenyl}pyrimidin-2-yl)amino]benzenesulfonamide;
N-[3-(dimethylamino)propyl]-4-[(4-{4-[(1E)-3-hydrox-
yprop-1-en-1-yl]phenyl}pyrimidin-2-yl)amino]benze-
nesulfonamide;
4-({4-[4-(2,5-dimethyl-1H-pyrrol-1-yl)phenyl]pyrimi-
din-2-yl}amino)benzenesulfonamide;
4-[(4-{4-[(1E)-3-hydroxyprop-1-en-1-yl]
phenyl}pyrimidin-2-yl)amino]benzenesulfonamide;
or a pharmaceutically acceptable salt thereof.

55. A compound selected from the group consisting of:
4-{[4-(4-tert-butoxyphenyl)pyrimidin-2-yl]amino}-N-[2-
(dimethylamino)ethyl]benzenesulfonamide;
N-[2-(dimethylamino)ethyl]-4-{[4-(4-formylphenyl)pyri-
midin-2-yl]amino}benzenesulfonamide;
N-[2-(dimethylamino)ethyl]-4-{[4-(4-fluorophenyl)pyri-
midin-2-yl]amino}benzenesulfonamide;
N-(3,3-diethoxypropyl)-4-{[4-(2,3-dihydro-1-benzofu-
ran-5-yl)pyrimidin-2-yl]amino}benzenesulfonamide;
4-{[4-(2,3-dihydro-1-benzofuran-5-yl)pyrimidin-2-yl]
amino}-N-(3-oxopropyl)benzenesulfonamide;
or a pharmaceutically acceptable salt thereof.

56. A compound selected from the group consisting of:
N-[2-(dimethylamino)ethyl]-4-({4-[4-(1,3-oxazol-5-yl)
phenyl]pyrimidin-2-yl}amino)benzenesulfonamide;
4-(2-{[4-({[2-(dimethylamino)ethyl]amino}sulfonyl)
phenyl]amino}pyrimidin-4-yl)benzamide;
N-[3-(dimethylamino)propyl]-4-[(4-{4-[(1E)-3-(1H-imi-
dazol-1-yl) prop-1-en-1-yl]phenyl}pyrimidin-2-yl)
amino]benzenesulfonamide;
N-[3-(dimethylamino)propyl]-4-{[4-(4-{(1E)-3-[methyl
(2-thienyl)amino]prop-1-en-1-yl]phenyl)pyrimidin-2-
yl]amino}benzenesulfonamide;
4-{[4-(4-{(1E)-3-[(2-hydroxyethyl)amino]prop-1-en-1-
yl]phenyl)pyrimidin-2-yl]amino}benzenesulfonamide;
or a pharmaceutically acceptable salt thereof.

57. A compound selected from the group consisting of:
4-{[4-(4-{(1E)-3-[(3-hydroxypropyl)amino]prop-1-en-1-
yl]phenyl)pyrimidin-2-yl]amino}benzenesulfonamide;
N-[3-(dimethylamino)propyl]-4-[(4-{4-[(1E)-3-morpho-
lin-4-ylprop-1-en-1-yl]phenyl}pyrimidin-2-yl)amino]
benzenesulfonamide;
4-[(4-{4-[(1E)-3-(dimethylamino)prop-1-en-1-yl]
phenyl}pyrimidin-2-yl)amino]-N-[3-(dimethylamino)
propyl]benzenesulfonamide;
N-[3-(dimethylamino)propyl]-4-{[4-(4-formylphenyl)py-
rimidin-2-yl]amino}benzenesulfonamide;
4-{[4-(2,3-dihydro-1-benzofuran-5-yl)pyrimidin-2-yl]
amino}-N-[3-(dimethylamino)propyl]benzenesulfona-
mide;
or a pharmaceutically acceptable salt thereof.

58. A compound selected from the group consisting of:
N-[3-(dimethylamino)propyl]-4-{[4-(4-fluorophenyl)py-
rimidin-2-yl]amino}benzenesulfonamide;
4-{[4-(2,3-dihydro-1-benzofuran-5-yl)pyrimidin-2-yl]
amino}-N-[3-(4-methylpiperazin-1-yl)propyl]benze-
nesulfonamide;
4-{[4-(4-piperidin-1-ylphenyl)pyrimidin-2-yl]
amino}benzenesulfonamide;
4-({4-[4-(4-methylpiperazin-1-yl)phenyl]pyrimidin-2-
yl}amino)benzenesulfonamide;
N-[3-(dimethylamino)propyl]-4-({4-[4-(hydroxymethyl)
phenyl]pyrimidin-2-yl}amino)benzenesulfonamide;
or a pharmaceutically acceptable salt thereof.

59. A compound selected from the group consisting of:
4-{[4-(1-benzothien-2-yl)pyrimidin-2-yl]amino}-N-[2-
(dimethylamino)ethyl]benzenesulfonamide;
4-{[4-(5,6-dihydro-4H-pyrrolo[1,2-b]pyrazol-2-yl)pyri-
midin-2-yl]amino}benzenesulfonamide;
N-[3-(dimethylamino)propyl-4-[(4-{4-[(1E)-3-methox-
yprop-1-en-1-yl]phenyl}pyrimidin-2-yl)amino]benze-
nesulfonamide.

* * * * *